(12) United States Patent
Chang et al.

(10) Patent No.: US 9,371,321 B2
(45) Date of Patent: Jun. 21, 2016

(54) AZAINDOLE DERIVATIVES

(71) Applicant: Takeda Pharmaceutical Company Limited, Osaka (JP)

(72) Inventors: Edcon Chang, San Diego, CA (US); Christopher Smith, San Diego, CA (US); Xiaolun Wang, San Diego, CA (US); Michael B. Wallace, San Diego, CA (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 14/592,801

(22) Filed: Jan. 8, 2015

(65) Prior Publication Data

US 2015/0191465 A1    Jul. 9, 2015

Related U.S. Application Data

(60) Provisional application No. 61/925,598, filed on Jan. 9, 2014.

(51) Int. Cl.
| | | |
|---|---|---|
| *C07D 403/14* | (2006.01) | |
| *A61K 31/506* | (2006.01) | |
| *C07D 471/04* | (2006.01) | |
| *A61K 31/5513* | (2006.01) | |
| *C07D 519/00* | (2006.01) | |

(52) U.S. Cl.
CPC ............ *C07D 471/04* (2013.01); *A61K 31/506* (2013.01); *A61K 31/5513* (2013.01); *C07D 403/14* (2013.01); *C07D 519/00* (2013.01)

(58) Field of Classification Search
CPC ............................ C07D 403/14; A61K 31/506
USPC ................... 540/575; 544/295, 324; 514/218, 514/252.18, 275
See application file for complete search history.

(56) References Cited

U.S. PATENT DOCUMENTS

| | | | |
|---|---|---|---|
| 6,518,277 B1 | 2/2003 | Dick et al. | |
| 6,667,300 B2 | 12/2003 | Dick et al. | |
| 6,806,272 B2 | 10/2004 | Bauer et al. | |
| 6,861,422 B2 | 3/2005 | Baum et al. | |
| 7,238,807 B2 | 7/2007 | Duran et al. | |
| 7,241,889 B2 | 7/2007 | Grauert et al. | |
| 7,371,753 B2 | 5/2008 | Stadtmueller | |
| 8,835,420 B2* | 9/2014 | Chang et al. ............. | 514/210.21 |
| 2004/0029885 A1 | 2/2004 | Bauer et al. | |
| 2004/0176380 A1 | 9/2004 | Hoffmann et al. | |
| 2004/0186292 A1 | 9/2004 | Wang et al. | |
| 2006/0014751 A1 | 1/2006 | Grauert et al. | |
| 2006/0035903 A1 | 2/2006 | Mohr et al. | |
| 2006/0046990 A1 | 3/2006 | Stadtmueller et al. | |
| 2006/0122393 A1 | 6/2006 | Duran et al. | |
| 2007/0259910 A1 | 11/2007 | Halley et al. | |
| 2008/0177066 A1 | 7/2008 | Linz et al. | |
| 2014/0018344 A1* | 1/2014 | Chang et al. ............. | 514/210.21 |
| 2014/0343033 A1 | 11/2014 | Chang et al. | |

FOREIGN PATENT DOCUMENTS

| | | |
|---|---|---|
| WO | WO99/40091 A1 | 8/1999 |
| WO | WO/01/81346 | 11/2001 |
| WO | WO/03/035075 | 5/2003 |
| WO | WO/04/000210 | 12/2003 |
| WO | WO/2004/042002 | 12/2004 |
| WO | WO/2005/026158 | 3/2005 |
| WO | WO/2005/026175 | 3/2005 |
| WO | WO/2005/063767 | 7/2005 |
| WO | WO/2006/001894 | 1/2006 |
| WO | WO2006/005915 | 1/2006 |
| WO | WO/2006/018182 | 2/2006 |
| WO | WO/2006/018185 | 2/2006 |
| WO | WO/2007/014838 | 2/2007 |
| WO | WO2008/023180 | 2/2008 |
| WO | WO/2008/157179 | 12/2008 |
| WO | WO/2009/023718 | 2/2009 |
| WO | WO/2010/036380 | 4/2010 |
| WO | WO/2010/129467 | 11/2010 |
| WO | WO/2010/151735 | 12/2010 |
| WO | WO/2010/151740 | 12/2010 |
| WO | WO/2011/008487 | 1/2011 |
| WO | WO/2015/106012 | 7/2015 |

OTHER PUBLICATIONS

Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*

(Continued)

Primary Examiner — Deepak Rao

(57) ABSTRACT

Disclosed are compounds of Formula 1,

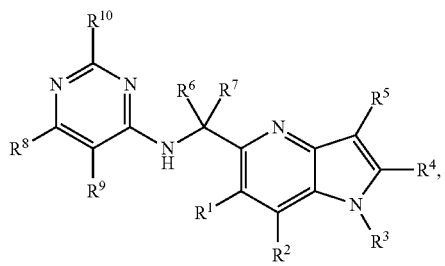

and pharmaceutically acceptable salts thereof, wherein $R^1$, $R^2$, $R^3$, $R^4$, $R^5$, $R^6$, $R^7$, $R^8$, $R^9$, and $R^{10}$ are defined in the specification. This disclosure also relates to materials and methods for preparing compounds of Formula 1, to pharmaceutical compositions which contain them, and to their use for treating immunological disorders, cardiovascular disease, cancer, and other diseases, disorders or conditions associated with PI3Kδ.

37 Claims, No Drawings

(56) References Cited

OTHER PUBLICATIONS

Fry, Review: Phosphoinositide 3-kinase signalling in breast cancer: how biga role might it play?, Breast Cancer Res. (2001), 3, pp. 304-312.*
L.C. Cantley, Science 296:1655-57 (2002).
Jimenez, et al., J. Biol. Chem., 277(44):41556-62 (2002).
C. Brock, et al., J. Cell. Biol., 160(1):89-99 (2003).
B. Vanhaesebroeck, et al., Trends Biochem. Sci. 30:194-204 (2005).
C. Rommel et al., Nature Rev. Immunology, 7:191-201 (2007).
A. Ghigo et al., BioEssays 32:185-196 (2010).
M. Camps et al., Nature Med. 11:936-43 (2005).
G. S. Firestein, N. Engl. J. Med. 354:80-82 (2006).
S. Hayer et al., FASEB J 23:4288-98 (2009) (RA).
D. F. Barber et al., Nature Med. 11:933-35 (2005) (SLE).
A. Fougerat et al., Circulation 117:1310-17. 2008.
T. M. Randis et al., Eur. J. Immunol. 38:1215-24 (2008) (RA).
Lee et al., FASEB J. 20:455-65 (2006).
H. S. Farghaly et al., Mol. Pharmacol. 73:1530-37 (2008).
K. Ali et al., Nature 431:1007-11 (2004).
J. Doukas et al., J. Pharmacol. Exp. Ther. 328:758-65 (2009).
J. Doukas et al., Proc. Nat'l Acad. Sci. USA 103:19866-71 (2006).
Y. Samuels et al., Science 304:554 (2004).
Y. Samuels & K. Ericson, Curr. Opin. Oncol. 18(1):77-82 (2006).
S. Kang et al., Proc. Nat'l Acad. Sci. USA 102(3):802-7 (2005).
A. Bader et al., Proc. Nat'l Acad. Sci. USA 103(5):1475-79 (2006).
P. Sujobert et al., Blood 106(3):1063-66 (2005).
C. Billottet et al., Oncogene 25(50):6648-59 (2006).
F. Hickey & T. Cotter, J. Biol. Chem. 281(5):2441-50 (2006).
C. Benistant et al., Oncogene, 19(44):5083-90 (2000).
M. Mizoguchi et al., Brain Pathology 14(4):372-77 (2004).
C. Knobbe et al, Neuropathology Appl. Neurobiolgy 31(5):486-90 (2005).

* cited by examiner

AZAINDOLE DERIVATIVES

FIELD OF THE INVENTION

This invention relates to substituted 4-azaindole derivatives and related compounds, which are inhibitors of PI3Kδ, to pharmaceutical compositions which contain them, and to the use of the inhibitors to treat diseases, disorders or conditions associated with PI3Kδ, including immunological disorders, cancer, and cardiovascular disease.

BACKGROUND OF THE INVENTION

The phosphoinositide 3-kinases (PI3Ks) are lipid and protein kinases involved in intracellular signal transduction. They act primarily through phosphorylation of phosphoinositides at the D3 position of the inositol ring, and are typically grouped into three classes (I, II, and III) based on their structure, function, and substrate specificity. The class I PI3Ks, denoted PI3Kα, PI3Kβ, PI3Kγ, and PI3Kδ, catalyze the phosphorylation of phosphatidylinositol-4,5-bisphosphate to phosphatidylinositol-3,4,5-trisphosphate, which functions as a second messenger whose binding to proteins containing pleckstrin homology domains, such as AKT, PDK1, Btk, GTPase activating proteins, and guanine nucleotide exchange factors, triggers a cascade of cellular processes involved with cell growth, survival, proliferation, apoptosis, adhesion, and migration, among others. See L. C. Cantley, *Science* 296:1655-57 (2002). Class I PI3K isoforms exist as heterodimers composed of a catalytic subunit, p110, and an associated regulatory subunit that controls their expression, activation, and subcellular localization. PI3Kα, PI3Kβ, and PI3Kδ associate with a regulatory subunit, p85, and are activated by growth factors and cytokines through a tyrosine kinase-dependent mechanism; PI3Kγ associates with two regulatory subunits, p101 and p84, and is activated by G-protein-coupled receptors. See C. Jimenez, et al., *J. Biol. Chem.*, 277(44):41556-62 (2002) and C. Brock, et al., *J. Cell. Biol.*, 160(1):89-99 (2003).

Although PI3Kα and PI3Kβ are expressed in many tissue types, PI3Kγ and PI3Kδ are predominantly expressed in leukocytes and are therefore thought to be attractive targets for treating inflammatory disorders and other diseases related to the immune system. See B. Vanhaesebroeck, et al., *Trends Biochem. Sci.* 30:194-204 (2005), C. Rommel et al., *Nature Rev. Immunology*, 7:191-201 (2007), and A. Ghigo et al., *BioEssays* 32:185-196 (2010). Recent preclinical studies support this view. For example, treatments with selective PI3Kγ inhibitors suppress the progression of joint inflammation and damage in mouse models of rheumatoid arthritis (RA), and reduce glomerulonephritis and extend survival in the MRL-lpr mouse model of systemic lupus erythematosus (SLE). See M. Camps et al., *Nature Med.* 11:936-43 (2005), G. S. Firestein, *N. Engl. J. Med.* 354:80-82 (2006), and S. Hayer et al., *FASEB J* 23:4288-98 (2009) (RA); see also D. F. Barber et al., *Nature Med.* 11:933-35 (2005) (SLE). A selective PI3Kγ inhibitor has also been shown to reduce formation and size of lesions in mouse models of early- and advanced-stage atherosclerosis, and to stabilize plaque formation thereby minimizing risks of plaque rupture and subsequent thrombosis and myocardial infarction. See A. Fougerat et al., *Circulation* 117:1310-17. 2008. Treatments with PI3Kδ-selective inhibitors significantly reduce inflammation and associated bone and cartilage erosion following injection of wild type mice with an arthritogenic serum, attenuate allergic airway inflammation and hyper-responsiveness in a mouse model of asthma, and protect mice against anaphylactic allergic responses. See T. M. Randis et al., *Eur. J. Immunol.* 38:1215-24 (2008) (RA); K. S. Lee et al., *FASEB J.* 20:455-65 (2006) and H. S. Farghaly et al., *Mol. Pharmacol.* 73:1530-37 (2008) (asthma); K. Ali et al., *Nature* 431:1007-11 (2004) (anaphylaxis). Administration of a PI3Kγ and PI3Kδ dual selective inhibitor has been shown to be efficacious in murine models of allergic asthma and chronic obstructive pulmonary disease (COPD) and is cardioprotective in murine and porcine models of myocardial infarction (MI). See J. Doukas et al., *J. Pharmacol. Exp. Ther.* 328:758-65 (2009) (asthma and COPD); J. Doukas et al., *Proc. Nat'l Acad. Sci. USA* 103: 19866-71 (2006) (MI).

Studies also suggest targeting one or more of the four class I PI3K isoforms may yield useful treatments for cancer. The gene encoding p110α is mutated frequently in common cancers, including breast, brain, prostate, colon, gastric, lung, and endometrial cancers. See Y. Samuels et al., *Science* 304: 554 (2004) and Y. Samuels & K. Ericson, *Curr. Opin. Oncol.* 18(1):77-82 (2006). One of three amino acid substitutions in the helical or kinase domains of the enzyme are responsible for 80 percent of these mutations, which lead to significant up-regulation of kinase activity and result in oncogenic transformation in cell culture and in animal models. See S. Kang et al., *Proc. Nat'l Acad. Sci. USA* 102(3):802-7 (2005) and A. Bader et al., *Proc. Nat'l Acad. Sci. USA* 103(5):1475-79 (2006). No such mutations have been identified in the other PI3K isoforms, though there is evidence they can contribute to the development and progression of malignancies. PI3Kδ is consistently over expressed in acute myeloblastic leukemia and inhibitors of PI3Kδ can prevent the growth of leukemic cells. See P. Sujobert et al., *Blood* 106(3):1063-66 (2005); C. Billottet et al., *Oncogene* 25(50):6648-59 (2006). PI3Kγ expression is elevated in chronic myeloid leukemia. See F. Hickey & T. Cotter, *J. Biol. Chem.* 281(5):2441-50 (2006). Alterations in expression of PI3Kβ, PI3Kγ, and PI3Kδ have also been observed in cancers of the brain, colon and bladder. See C. Benistant et al., *Oncogene,* 19(44):5083-90 (2000), M. Mizoguchi et al., *Brain Pathology* 14(4):372-77 (2004), and C. Knobbe et al, *Neuropathology Appl. Neurobiolgy* 31(5): 486-90 (2005). Moreover, all of these isoforms have been shown to be oncogenic in cell culture. See S. Kang et al. (2006).

International patent application PCT/US13/49612, which was filed on Jul. 8, 2013 and published as WO 2014/011568 on Jan. 16, 2014, describes and claims various 4-azaindole derivatives. Although potent inhibitors of PI3Kδ, the compounds in PCT/US13/49612 exhibit comparatively low aqueous solubility, which may make them unsuitable for certain therapeutic applications.

Inhibitors of PI3K are also described in U.S. Pat. No. 6,518,277, U.S. Pat. No. 6,667,300, WO 01/81346, WO 03/035075, WO 2006/005915, WO2008/023180, WO2010/ 036380, WO2010/151735, WO2010/151740, and WO2011/ 008487.

SUMMARY OF THE INVENTION

This invention provides substituted 4-azaindole derivatives and related compounds, and pharmaceutically acceptable salts thereof. This invention also provides pharmaceutical compositions that contain the substituted 4-azaindoles and provides for their use to treat diseases, disorders or conditions associated with PI3Kδ inhibition, including immunological disorders, cancer, and cardiovascular disease.

One aspect of the invention provides a compound of Formula 1:

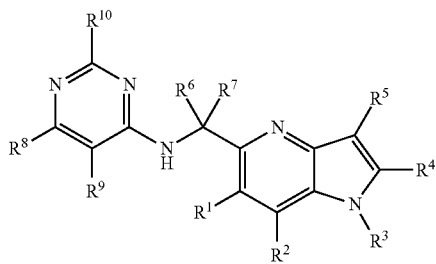

or a pharmaceutically acceptable salt thereof, wherein:

$R^1$ is selected from:
- (a) $C_{3-8}$ cycloalkyl, which is substituted with —$NHR^{13}$ and is optionally substituted with one or two additional substituents independently selected from halo, oxo, —CN, $R^{11}$, and $R^{12}$;
- (b) $C_{3-8}$ cycloalkenyl, which is substituted with —$NHR^{13}$ and is optionally substituted with one or two additional substituents independently selected from halo, oxo, —CN, $R^{11}$, and $R^{12}$;
- (c) $C_{2-6}$ heterocyclyl, which is bonded directly to an azaindole moiety shown in Formula 1 through a carbon atom, has at least one heteroatom that is unsubstituted nitrogen, and is optionally substituted with one to three substituents independently selected from halo, oxo, —CN, $R^{11}$, and $R^{12}$;
- (d) $C_{2-6}$ heterocyclyl, which is bonded directly to the azaindole moiety through a nitrogen heteroatom, is substituted with —$NHR^{13}$ or has at least one additional heteroatom that is unsubstituted nitrogen, and is optionally substituted with one to three substituents independently selected from halo, oxo, —CN, $R^{11}$, and $R^{12}$; and
- (e) $C_{2-6}$ heterocyclyl-$N(R^{13})$— in which the heterocyclyl moiety has at least one heteroatom that is unsubstituted nitrogen, and is optionally substituted with one to three substituents independently selected from halo, oxo, —CN, $R^{11}$, and $R^{12}$;

$R^2$, $R^4$, and $R^5$ are each independently selected from hydrogen, halo, —OH, —CN, $C_{1-3}$ alkyl, and $C_{1-3}$ haloalkyl;

$R^3$ is selected from hydrogen, $C_{1-3}$ alkyl, and $C_{1-3}$ haloalkyl;

$R^6$ and $R^7$ are each independently selected from hydrogen, $C_{1-3}$ alkyl, and $C_{1-3}$ haloalkyl;

$R^8$ is selected from hydrogen, $C_{1-3}$ alkyl, and —$NH_2$;

$R^9$ is selected from hydrogen, halo, —CN, $C_{1-3}$ haloalkyl, —$OR^{16}$, —$C(O)R^{16}$, —$C(O)OR^{16}$, —$C(O)N(R^{16})R^{17}$, —$C(O)N(R^{16})OR^{17}$, —$C(O)N(R^{16})S(O)_2R^{18}$, —$SR^{16}$, —$S(O)R^{18}$, —$S(O)_2R^{18}$, and —$S(O)_2N(R^{16})R^{17}$;

$R^{10}$ is selected from halo, —OH, $C_{1-3}$ alkyl, —$NHR^{16}$, and —$NHC(O)R^{16}$;

each $R^{11}$ is independently selected from —$OR^{13}$, —$N(R^{13})R^{14}$, —$NR^{13}C(O)R^{14}$, —$NHC(O)NR^{13}R^{14}$, —$NR^{13}C(O)NHR^{14}$, —$C(O)R^{13}$, —$C(O)OR^{13}$, —$C(O)N(R^{13})R^{14}$, —$C(O)N(R^{13})OR^{14}$, —$C(O)N(R^{13})S(O)_2R^{12}$, —$N(R^{13})S(O)_2R^{12}$, —$SR^{13}$, —$S(O)R^{12}$, —$S(O)_2R^{12}$, and —$S(O)_2N(R^{13})R^{14}$;

each $R^{12}$ is independently selected from $C_{1-6}$ alkyl, $C_{2-6}$ alkenyl, $C_{2-6}$ alkynyl, $C_{3-8}$ cycloalkyl-$(CH_2)_m$—, $C_{6-14}$ aryl-$(CH_2)_m$—, $C_{2-6}$ heterocyclyl-$(CH_2)_m$—, and $C_{1-9}$ heteroaryl-$(CH_2)_m$—, each optionally substituted with from one to five substituents independently selected from halo, oxo, —CN, $C_{1-6}$ alkyl, $C_{1-6}$ haloalkyl, and $R^{15}$;

each $R^{13}$ and $R^{14}$ is independently selected from
- (a) hydrogen; and
- (b) $C_{1-6}$ alkyl, $C_{2-6}$ alkenyl, $C_{2-6}$ alkynyl, $C_{3-6}$ cycloalkyl-$(CH_2)_m$—, $C_{6-14}$ aryl-$(CH_2)_m$—, $C_{2-6}$ heterocyclyl-$(CH_2)_m$—, and $C_{1-9}$ heteroaryl-$(CH_2)_m$—, each optionally substituted with from one to five substituents independently selected from halo, oxo, —CN, $C_{1-6}$ alkyl, $C_{1-6}$ haloalkyl, and $R^{15}$;

each $R^{15}$ is independently selected from —$OR^{16}$, —$N(R^{16})R^{17}$, —$NR^{16}C(O)R^{17}$, —$NHC(O)NR^{16}R^{17}$, —$NR^{16}C(O)NHR^{17}$, —$C(O)R^{16}$, —$C(O)OR^{16}$, —$C(O)N(R^{16})R^{17}$, —$C(O)N(R^{16})OR^{17}$, —$C(O)N(R^{16})S(O)_2R^{18}$, —$NR^{16}S(O)_2R^{18}$, —$SR^{16}$, —$S(O)R^{18}$, —$S(O)_2R^{18}$, and —$S(O)_2N(R^{16})R^{17}$;

each $R^{16}$ and $R^{17}$ is independently selected from hydrogen, $C_{1-6}$ alkyl, and $C_{3-6}$ cycloalkyl;

each $R^{18}$ is independently selected from $C_{1-6}$ alkyl and $C_{3-6}$ cycloalkyl;

each m is independently selected from 0, 1, 2, 3, and 4;

wherein each of the aforementioned heteroaryl moieties independently has 1 to 4 heteroatoms independently selected from N, O, and S, and each of the aforementioned heterocyclyl moieties independently has 1 to 4 heteroatoms independently selected from N, O, and S.

Another aspect of the invention provides a compound of Formula 1 as defined above, which is selected from the compounds described in the examples, their pharmaceutically acceptable salts, and stereoisomers of any of the compounds in the examples and their pharmaceutically acceptable salts.

A further aspect of the invention provides a pharmaceutical composition which includes a compound of Formula 1 or a pharmaceutically acceptable salt thereof as defined above, and a pharmaceutically acceptable excipient.

An additional aspect of the invention provides a compound of Formula 1 or a pharmaceutically acceptable salt thereof as defined above for use as a medicament.

Another aspect of the invention provides a compound of Formula 1 or a pharmaceutically acceptable salt thereof as defined above for use in the manufacture of a medicament for the treatment of a condition associated with PI3Kδ.

A further aspect of the invention provides a method of treating a disease, disorder or condition associated with PI3Kδ in a subject, the method comprising administering to the subject an effective amount of a compound of Formula 1 or a pharmaceutically acceptable salt thereof as defined above.

An additional aspect of the invention provides a method of treating a disease, disorder or condition in a subject, the method comprising administering to the subject an effective amount of a compound of Formula 1 or a pharmaceutically acceptable salt thereof as defined above, wherein the disease, disorder or condition is selected from immunological disorders, cancer, and cardiovascular disease.

Another aspect of the invention provides a method of treating a disease, disorder or condition in a subject, the method comprising administering to the subject an effective amount of a compound of Formula 1 or a pharmaceutically acceptable salt thereof as defined above, wherein the disease, disorder or condition is selected from allergic rhinitis, asthma (including exacerbation of asthma), atopic dermatitis, rheumatoid arthritis, multiple sclerosis, systemic lupus erythematosus, psoriasis, immune thrombocytopenic purpura, inflammatory bowel disease, behcet's disease, graft-versus-host disease (GVHD), chronic obstructive pulmonary disease (including exacerbation of COPD), atherosclerosis, myocardial infarction, and thrombosis.

Another aspect of the invention provides a method of treating a disease, disorder or condition in a subject, the method comprising administering to the subject an effective amount of a compound of Formula 1 or a pharmaceutically acceptable salt thereof as defined above, wherein the disease or condition is selected from brain cancer, lung cancer, squamous cell cancer, bladder cancer, gastric cancer, pancreatic cancer, breast cancer, cancer of the head, neck cancer, renal cancer, kidney cancer, ovarian cancer, prostate cancer, colorectal cancer, prostate cancer, colon cancer, epidermoid cancer, esophageal cancer, testicular cancer, gynecological cancer, and thyroid cancer.

A further aspect of the invention provides a combination of an effective amount of a compound of Formula 1 or a pharmaceutically acceptable salt thereof as defined above, and at least one additional pharmacologically active agent.

DETAILED DESCRIPTION OF THE INVENTION

Unless otherwise indicated, this disclosure uses definitions provided below.

"Substituted," when used in connection with a chemical substituent or moiety (e.g., a $C_{1-6}$ alkyl group), means that one or more hydrogen atoms of the substituent or moiety have been replaced with one or more non-hydrogen atoms or groups, provided that valence requirements are met and that a chemically stable compound results from the substitution.

"About" or "approximately," when used in connection with a measurable numerical variable, refers to the indicated value of the variable and to all values of the variable that are within the experimental error of the indicated value or within ±10 percent of the indicated value, whichever is greater.

"Alkyl" refers to straight chain and branched saturated hydrocarbon groups, generally having a specified number of carbon atoms (e.g., $C_{1-3}$ alkyl refers to an alkyl group having 1 to 3 (i.e., 1, 2 or 3) carbon atoms, $C_{1-6}$ alkyl refers to an alkyl group having 1 to 6 carbon atoms, and so on). Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkenyl" refers to straight chain and branched hydrocarbon groups having one or more carbon-carbon double bonds, and generally having a specified number of carbon atoms. Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms. Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Halo," "halogen" and "halogeno" may be used interchangeably and refer to fluoro, chloro, bromo, and iodo.

"Haloalkyl," "haloalkenyl," and "haloalkynyl," refer, respectively, to alkyl, alkenyl, and alkynyl groups substituted with one or more halogen atoms, where alkyl, alkenyl, and alkynyl are defined above, and generally having a specified number of carbon atoms. Examples of haloalkyl groups include fluoromethyl, difluoromethyl, trifluoromethyl, chloromethyl, dichloromethyl, trichloromethyl, and the like.

"Cycloalkyl" refers to saturated monocyclic and bicyclic hydrocarbon groups, generally having a specified number of carbon atoms that comprise the ring or rings (e.g., $C_{3-8}$ cycloalkyl refers to a cycloalkyl group having 3 to 8 carbon atoms as ring members). Bicyclic hydrocarbon groups may include isolated rings (two rings sharing no carbon atoms), spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached through any ring atom unless such attachment would violate valence requirements.

Examples of monocyclic cycloalkyl groups include cyclopropyl, cyclobutyl, cyclopentyl, cyclohexyl, and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl, bicyclo[4.1.1]octanyl, bicyclo[3.3.1]nonanyl, bicyclo[4.2.1]nonanyl, bicyclo[3.3.2]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like. Examples of spiro cycloalkyl groups include spiro[3.3]heptanyl, spiro[2.4]heptanyl, spiro[3.4]octanyl, spiro[2.5]octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, cyclopentanecyclohexane, bi(cyclohexane), etc.

"Cycloalkylidene" refers to divalent monocyclic cycloalkyl groups, where cycloalkyl is defined above, which are attached through a single carbon atom of the group, and generally having a specified number of carbon atoms that comprise the ring (e.g., $C_{3-6}$ cycloalkylidene refers to a cycloalkylidene group having 3 to 6 carbon atoms as ring members). Examples include cyclopropylidene, cyclobutylidene, cyclopentylidene, and cyclohexylidene.

"Cycloalkenyl" refers to partially unsaturated monocyclic and bicyclic hydrocarbon groups, generally having a specified number of carbon atoms that comprise the ring or rings. As with cycloalkyl groups, the bicyclic cycloalkenyl groups may include isolated, spiro, fused, or bridged rings. Similarly, the cycloalkenyl group may be attached through any ring atom unless such attachment would violate valence requirements. Examples of cycloalkenyl groups include the partially unsaturated analogs of the cycloalkyl groups described above, such as cyclobutenyl (i.e., cyclobuten-1-yl and cyclobuten-3-yl), cyclopentenyl, cyclohexenyl, bicyclo[2.2.1]hept-2-enyl, and the like.

"Aryl" refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-14}$ aryl refers to an aryl group having 6 to 14 carbon atoms as ring members). The group may be attached through any ring atom unless such attachment would violate valence requirements. Examples of aryl groups include phenyl, biphenyl, cyclobutabenzenyl, indenyl, naphthalenyl, benzocycloheptanyl, biphenylenyl, fluorenyl, groups derived from cycloheptatriene cation, and the like.

"Arylene" refers to divalent aryl groups, where aryl is defined above. Examples of arylene groups include phenylene (i.e., benzene-1,2-diyl).

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen, oxygen, and sulfur. Both the monocyclic and bicyclic groups generally have a specified number of carbon atoms in their ring or rings (e.g., $C_{2-6}$ heterocyclyl refers to a heterocyclyl group having 2 to 6 carbon atoms and 1 to 4 heteroatoms as ring members). As with bicyclic cycloalkyl groups, bicyclic heterocyclyl groups may include isolated rings, spiro rings, fused rings, and bridged rings. The heterocyclyl group may be attached through any ring atom unless such attachment would violate valence requirements or result in a chemically unstable compound. Examples of monocyclic heterocyclyl groups include oxiranyl, thiiranyl, aziridinyl (e.g., aziridin-1-yl and aziridin-2-yl), oxetanyl, thietanyl, azetidinyl, tetrahydrofuranyl, tetrahydrothiopheneyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 3,6-dihydro-2H-pyranyl, 2H-pyranyl, 1,2-dihydropyridine, 1,2,3,4-tetrahydropyridinyl, and 1,2,5,6-tetrahydropyridinyl.

"Heterocycle-diyl" refers to heterocyclyl groups which are attached through two ring atoms of the group, where heterocyclyl is defined above. They generally have a specified number of carbon atoms in their ring or rings (e.g., $C_{2-6}$ heterocycle-diyl refers to a heterocycle-diyl group having 2 to 6 carbon atoms and 1 to 4 heteroatoms as ring members). Examples of heterocycle-diyl groups include the multivalent analogs of the heterocycle groups described above, such as morpholine-3,4-diyl, pyrrolidine-1,2-diyl, 1-pyrrolidinyl-2-ylidene, 1-pyridinyl-2-ylidene, 1-(4H)-pyrazolyl-5-ylidene, 1-(3H)-imidazolyl-2-ylidene, 3-oxazolyl-2-ylidene, 1-piperidinyl-2-ylidene, 1-piperazinyl-6-ylidene, and the like.

"Heteroaromatic" and "heteroaryl" may be used interchangeably and refer to unsaturated monocyclic aromatic groups and to polycyclic groups having at least one aromatic ring, each of the groups having ring atoms composed of carbon atoms and 1 to 4 heteroatoms independently selected from nitrogen, oxygen, and sulfur. Both the monocyclic and polycyclic groups generally have a specified number of carbon atoms as ring members (e.g., $C_{1-9}$ heteroaryl refers to a heteroaryl group having 1 to 9 carbon atoms and 1 to 4 heteroatoms as ring members) and may include any bicyclic group in which any of the above-listed monocyclic heterocycles are fused to a benzene ring. The heteroaryl group may be attached through any ring atom (or ring atoms for fused rings) unless such attachment would violate valence requirements or result in a chemically unstable compound. Examples of heteroaryl groups include monocyclic groups such as pyrrolyl (e.g., pyrrol-1-yl, pyrrol-2-yl, and pyrrol-3-yl), furanyl, thiopheneyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzothiopheneyl, benzo[c]thiopheneyl, indolyl, 3H-indolyl, isoindolyl, 1H-isoindolyl, indolinyl, isoindolinyl, benzimidazolyl, indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, and pyrimido[4,5-d]pyrimidinyl.

"Heteroarylene" refers to heteroaryl groups which are attached through two ring atoms of the group, where heteroaryl is defined above. They generally have a specified number of carbon atoms in their ring or rings (e.g., $C_{3-5}$ heteroarylene refers to a heteroarylene group having 3 to 5 carbon atoms and 1 to 4 heteroatoms as ring members). Examples of heteroarylene groups include the multivalent analogs of the heteroaryl groups described above, such as pyridin-2,3-diyl, pyridin-3,4-diyl, 1H-imidazol-4,5-diyl, 1H-pyrazol-4,5-diyl, 1H-pyrazol-3,4-diyl, 1H-triazol-4,5-diyl, and the like.

"Oxo" refers to a double bonded oxygen (=O).

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate), and arylsulfonates (e.g., tosylate, brosylate, closylate, and nosylate). Others include carbonates, halide ions, carboxylate anions, phenolate ions, and alkoxides. Some stronger bases, such as $NH_2^-$ and $OH^-$ can be made better leaving groups by treatment with an acid. Common electrofugal leaving groups include the proton, $CO_2$, and metals.

"Opposite enantiomer" refers to a molecule that is a non-superimposable mirror image of a reference molecule, which may be obtained by inverting all of the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Stereoisomer" and "stereoisomers" of a compound with given stereochemical configuration refer to the opposite enantiomer of the compound and to any diastereoisomers, including geometrical isomers (Z/E) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomer" refers to any one of the possible stereochemical configurations of the compound.

"Substantially pure stereoisomer" and variants thereof refer to a sample containing a compound having a specific stereochemical configuration and which comprises at least about 95% of the sample.

"Pure stereoisomer" and variants thereof refer to a sample containing a compound having a specific stereochemical configuration and which comprises at least about 99.5% of the sample.

"Subject" refers to a mammal, including a human.

"Pharmaceutically acceptable" substances refer to those substances which are suitable for administration to subjects.

"Treating" refers to reversing, alleviating, inhibiting the progress of, or preventing a disease, disorder or condition to which such term applies, or to reversing, alleviating, inhibiting the progress of, or preventing one or more symptoms of such disease, disorder or condition.

"Treatment" refers to the act of "treating," as defined immediately above.

"Drug," "drug substance," "active pharmaceutical ingredient," and the like, refer to a compound (e.g., compounds of Formula 1, including subgeneric compounds and compounds specifically named in the specification) that may be used for treating a subject in need of treatment.

"Effective amount" of a drug, "therapeutically effective amount" of a drug, and the like, refer to the quantity of the drug that may be used for treating a subject and may depend on the weight and age of the subject and the route of administration, among other things.

"Excipient" refers to any diluent or vehicle for a drug.

"Pharmaceutical composition" refers to the combination of one or more drug substances and one or more excipients.

"Drug product," "pharmaceutical dosage form," "dosage form," "final dosage form" and the like, refer to a pharmaceutical composition suitable for treating a subject in need of treatment and generally may be in the form of tablets, capsules, sachets containing powder or granules, liquid solutions or suspensions, patches, films, and the like.

"Condition associated with PI3Kδ" and similar phrases relate to a disease, disorder or condition in a subject for which inhibition of PI3Kδ may provide a therapeutic or prophylactic benefit.

The following abbreviations are used throughout the specification: Ac (acetyl); ACN (acetonitrile); AIBN (azo-bis-isobutyronitrile); API (active pharmaceutical ingredient); aq (aqueous); Boc (tert-butoxycarbonyl); Cbz (carbobenzyloxy); dba (dibenzylideneacetone); DCC (1,3-dicyclohexylcarbodiimide); DCE (1,1-dichloroethane); DCM (dichloromethane); DIPEA (N,N-diisopropylethylamine, Hünig's Base); DEAD (diethyl azodicarboxylate or diethyl (E)-diazene-1,2-dicarboxylate); DMA (N,N-dimethylacetamide); DMAP (4-dimethylaminopyridine); DMARD (disease modifying antirheumatic drug); DME (1,2-dimethoxyethane); DMF (N,N-dimethylformamide); DMPU (1,3-dimethyl-3,4,5,6-tetrahydro-2(1H)-pyrimidinone; DMSO (dimethylsulfoxide); dppf (1,1'-bis(diphenylphosphino)ferrocene); DTT (dithiothreitol); EDA (ethoxylated dodecyl alcohol, Brij® 35); EDC (N-(3-dimethylaminopropyl)-N'-ethylcarbodiimide); EDTA (ethylenediaminetetraacetic acid); ee (enantiomeric excess); eq (equivalents); Et (ethyl); Et$_3$N (triethylamine); EtOAc (ethyl acetate); EtOH (ethanol); HATU (2-(3H-[1,2,3]triazolo[4,5-b]pyridin-3-yl)-1,1,3,3-tetramethyluronium hexafluorophosphate(V)); HEPES (4-(2-hydroxyethyl)piperazine-1-ethanesulfonic acid); HOAc (acetic acid); HOBt (1H-benzo[d][1,2,3]triazol-1-ol); IC$_{50}$ (concentration at 50% inhibition); IPA (isopropanol); IPAc (isopropyl acetate); IPE (isopropylether); KOt-Bu (potassium tertiary butoxide); LDA (lithium diisopropylamide); LiHMDS (lithium bis(trimethylsilyl)amide); mCPBA (m-chloroperoxybenzoic acid); Me (methyl); MeOH (methanol); MTBE (methyl tert-butyl ether); mp (melting point); NaOt-Bu (sodium tertiary butoxide); NMM (N-methylmorpholine); NMP (N-methyl-2-pyrrolidone); PE (petroleum ether); Ph (phenyl); pIC$_{50}$ (−log$_{10}$(IC$_{50}$), where IC$_{50}$ is given in molar (M) units); Pr (propyl); i-Pr (isopropyl); PTFE (polytetrafluoroethylene); RT (room temperature, approximately 20° C. to 25° C.); TCEP (tris(2-carboxyethyl)phosphine); TFA (trifluoroacetic acid); TFAA (2,2,2-trifluoroacetic anhydride); THF (tetrahydrofuran); TMS (trimethylsilyl); and Tris buffer (2-amino-2-hydroxymethyl-propane-1,3-diol buffer).

As described, below, this disclosure concerns compounds of Formula 1 and their pharmaceutically acceptable salts. This disclosure also concerns materials and methods for preparing compounds of Formula 1, pharmaceutical compositions which contain them, and the use of compounds of Formula 1 and their pharmaceutically acceptable salts (optionally in combination with other pharmacologically active agents) for treating immunological disorders, cancer, cardiovascular disorders, and conditions associated with PI3Kδ and optionally other PI3K isoforms.

In addition to the specific compounds in the examples, compounds of Formula 1 include those in which: (a) $R^1$ is $C_{3-8}$ cycloalkyl, which is substituted with —NHR$^{13}$ and is optionally substituted with one or two additional substituents independently selected from halo, oxo, —CN, $R^{11}$, and $R^{12}$; (b) $R^2$, $R^4$, and $R^5$ are each independently selected from hydrogen and halo; (c) at least one of $R^6$ and $R^7$ is hydrogen; (d) at least one of $R^6$ and $R^7$ is $C_{1-3}$ alkyl; or any combination of structural features (a) through (d).

In addition, or as an alternative, to one or more of embodiments (b) through (d) in the preceding paragraph, compounds of Formula 1 include those in which: (e) $R^1$ is $C_{3-8}$ cycloalkyl, which is substituted with —NHR$^{13}$ alone.

In addition, or as an alternative, to one or more of embodiments (b) through (d) in the preceding paragraph, compounds of Formula 1 include those in which: (f) $R^1$ is $C_{3-8}$ cycloalkyl, which is substituted with —NH$_2$ alone.

In addition, or as an alternative, to one or more of embodiments (b) through (d) in the preceding paragraph, compounds of Formula 1 include those in which: (g) $R^1$ is $C_{3-6}$ cycloalkyl, which is substituted with —NH$_2$ alone.

In addition, or as an alternative, to one or more of embodiments (b) through (d) in the preceding paragraph, compounds of Formula 1 include those in which: (h) $R^1$ is $C_{3-8}$ cycloalkenyl, which is substituted with —NHR$^{13}$ and is optionally substituted with one or two additional substituents independently selected from halo, oxo, —CN, $R^{11}$, and $R^{12}$.

In addition, or as an alternative, to one or more of embodiments (b) through (d) in the preceding paragraph, compounds of Formula 1 include those in which: (i) $R^1$ is $C_{3-8}$ cycloalkenyl, which is substituted with —NHR$^{13}$ alone.

In addition, or as an alternative, to one or more of embodiments (b) through (d) in the preceding paragraph, compounds of Formula 1 include those in which: (j) $R^1$ is $C_{3-8}$ cycloalkenyl, which is substituted with —NH$_2$ alone.

In addition, or as an alternative, to one or more of embodiments (b) through (d) in the preceding paragraph, compounds of Formula 1 include those in which: (k) $R^1$ is $C_{3-6}$ cycloalkenyl, which is substituted with —NH$_2$ alone.

In addition, or as an alternative, to one or more of embodiments (b) through (d) in the preceding paragraph, compounds of Formula 1 include those in which: (l) $R^1$ is $C_{2-6}$ heterocyclyl, which is bonded directly to the azaindole moiety through a carbon atom, has at least one heteroatom that is unsubstituted nitrogen, and is optionally substituted with one to three substituents independently selected from halo, oxo, —CN, $R^{11}$, and $R^{12}$.

In addition, or as an alternative, to one or more of embodiments (b) through (d) in the preceding paragraph, compounds of Formula 1 include those in which: (m) $R^1$ is $C_{3-6}$ heterocyclyl, which is bonded directly to the azaindole moiety through a carbon atom, has one unsubstituted nitrogen heteroatom and no other heteroatoms, and is optionally substituted with one to three substituents independently selected from halo, oxo, —CN, $R^{11}$, and $R^{12}$.

In addition, or as an alternative, to one or more of embodiments (b) through (d) in the preceding paragraph, compounds of Formula 1 include those in which: (n) $R^1$ is $C_{3-6}$ heterocyclyl, which is bonded directly to the azaindole moiety through a carbon atom, has one unsubstituted nitrogen heteroatom and no other heteroatoms, and is optionally substituted with $R^{18}$.

In addition, or as an alternative, to one or more of embodiments (b) through (d) in the preceding paragraph, compounds of Formula 1 include those in which: (o) $R^1$ is $C_{3-6}$ heterocyclyl, which is bonded directly to the azaindole moiety through a carbon atom, has one unsubstituted nitrogen heteroatom and no other heteroatoms, and is unsubstituted.

In addition, or as an alternative, to one or more of embodiments (b) through (d) in the preceding paragraph, compounds of Formula 1 include those in which: (p) $R^1$ is $C_{2-6}$ heterocyclyl, which is bonded directly to the azaindole moiety through a nitrogen heteroatom, is substituted with —$NHR^{13}$ or has at least one additional heteroatom that is unsubstituted nitrogen, and is optionally substituted with one to three substituents independently selected from halo, oxo, —CN, $R^{11}$, and $R^{12}$.

In addition, or as an alternative, to one or more of embodiments (b) through (d) in the preceding paragraph, compounds of Formula 1 include those in which: (q) $R^1$ is $C_{2-6}$ heterocyclyl, which is bonded directly to the azaindole moiety through a nitrogen heteroatom, is substituted with —$NHR^{16}$ or has at least one additional heteroatom that is unsubstituted nitrogen, and is optionally substituted with one to three substituents independently selected from halo, oxo, —CN, $R^{11}$, and $R^{12}$.

In addition, or as an alternative, to one or more of embodiments (b) through (d) in the preceding paragraph, compounds of Formula 1 include those in which: (r) $R^1$ is $C_{2-6}$ heterocyclyl, which is bonded directly to the azaindole moiety through a nitrogen heteroatom, is substituted with —$NHR^{16}$ or has at least one additional heteroatom that is unsubstituted nitrogen, and is optionally substituted with $R^{18}$.

In addition, or as an alternative, to one or more of embodiments (b) through (d) in the preceding paragraph, compounds of Formula 1 include those in which: (s) $R^1$ is $C_{2-6}$ heterocyclyl, which is bonded directly to the azaindole moiety through a nitrogen heteroatom, is substituted with —$NH_2$ or has one additional nitrogen heteroatom which is unsubstituted and no other heteroatoms, and is optionally substituted with $R^{18}$.

In addition, or as an alternative, to one or more of embodiments (b) through (d) in the preceding paragraph, compounds of Formula 1 include those in which: (t) $R^1$ is $C_{2-6}$ heterocyclyl-N($R^{13}$)— in which the heterocyclyl moiety has at least one heteroatom that is unsubstituted nitrogen, and is optionally substituted with one to three substituents independently selected from halo, oxo, —CN, $R^{11}$, and $R^{12}$.

In addition, or as an alternative, to one or more of embodiments (b) through (d) in the preceding paragraph, compounds of Formula 1 include those in which: (u) $R^1$ is $C_{3-6}$ heterocyclyl-N($R^{13}$)— in which the heterocyclyl moiety has one unsubstituted nitrogen heteroatom and no other heteroatoms, and is optionally substituted with one to three substituents independently selected from halo, oxo, —CN, $R^{11}$, and $R^{12}$.

In addition, or as an alternative, to one or more of embodiments (b) through (d) in the preceding paragraph, compounds of Formula 1 include those in which: (v) $R^1$ is $C_{3-6}$ heterocyclyl-N($R^{13}$)— in which the heterocyclyl moiety has one unsubstituted nitrogen heteroatom and no other heteroatoms, and is optionally substituted with $R^{18}$.

In addition, or as an alternative, to one or more of embodiments (b) through (d) in the preceding paragraph, compounds of Formula 1 include those in which: (w) $R^1$ is $C_{2-6}$ heterocyclyl-N($R^{13}$)— in which the heterocyclyl moiety has one unsubstituted nitrogen heteroatom and no other heteroatoms, and is unsubstituted.

In addition, or as an alternative, to one or more of embodiments (b) through (d) in the preceding paragraph, compounds of Formula 1 include those in which: (x) each of the heterocyclyl moieties for $R^1$ has 1 or 2 heteroatoms and each of the heteroatoms is nitrogen.

In addition, or as an alternative, to one or more of embodiments (b) through (d) in the preceding paragraph, compounds of Formula 1 include those in which: (y) $R^1$ is selected from aminocyclohexyl, aminocyclohexenyl, azetidinyl, pyrrolidinyl, piperidinyl, piperazinyl, diazepanyl, diazabicyclo[2.2.1]heptanyl, azetidinylamino, and piperidinylamino, each optionally substituted as indicated above.

In addition, or as an alternative, to one or more of embodiments (b) through (d) in the preceding paragraph, compounds of Formula 1 include those in which: (z) $R^1$ is selected from 4-aminocyclohexyl, 4-aminocyclohex-1-en-1-yl, pyrrolidin-3-yl, piperidin-4-yl, pyrrolidin-1-yl, piperidin-1-yl, piperazin-1-yl, 1,4-diazepan-1-yl, 2,5-diazabicyclo[2.2.1]heptan-2-yl, azetidin-3-ylamino, and piperidin-4-ylamino, each optionally substituted as indicated above.

In addition, or as an alternative, to one or more of embodiments (b) through (d) in the preceding paragraph, compounds of Formula 1 include those in which: (a') $R^1$ is selected from 4-aminocyclohexyl, 4-aminocyclohex-1-en-1-yl, (R)-pyrrolidin-3-yl, (S)-pyrrolidin-3-yl, piperidin-4-yl, (R)-3-aminopyrrolidin-1-yl, (S)-3-aminopyrrolidin-1-yl, (R)-3-(methylamino)pyrrolidin-1-yl, (S)-3-(methylamino)pyrrolidin-1-yl, (R)-3-aminopiperidin-1-yl, (S)-3-aminopiperidin-1-yl, piperazin-1-yl, (R)-3-methylpiperazin-1-yl, (S)-3-methylpiperazin-1-yl, 1,4-diazepan-1-yl, (1S,4S)-2,5-diazabicyclo[2.2.1]heptan-2-yl, azetidin-3-yl(methyl)amino, and piperidin-4-ylamino.

In addition, or as an alternative, to one or more of embodiments (a), (h), (l) through (n), (p) through (v), and (x) through (z) in the preceding paragraphs, compounds of Formula 1 include those in which: (b') $R^1$ is optionally substituted with one substituent independently selected from halo, hydroxy, oxo, —CN, $C_{1-3}$ alkyl, and $C_{1-3}$ haloalkyl.

In addition, or as an alternative, to one or more of embodiments (a), (h), (l) through (n), (p) through (v), and (x) through (z) in the preceding paragraphs, compounds of Formula 1 include those in which: (c') $R^1$ is optionally substituted with from one to three substituents independently selected from fluoro, hydroxy, oxo, —CN, methyl, and difluoromethyl.

In addition, or as an alternative, to one or more of embodiments (a), (h), (l) through (n), (p) through (v), and (x) through (z) in the preceding paragraphs, compounds of Formula 1 include those in which: (d') $R^1$ has no optional substituents.

In addition, or as an alternative, to one or more of embodiments (a) through (d') in the preceding paragraphs, compounds of Formula 1 include those in which: (e') $R^2$, $R^4$, and $R^5$ are each independently selected from hydrogen and halo and at most one of $R^2$, $R^4$, and $R^5$ is halo.

In addition, or as an alternative, to one or more of embodiments (a) through (d') in the preceding paragraphs, compounds of Formula 1 include those in which: (f') $R^2$, $R^4$, and $R^5$ are each independently selected from hydrogen and fluoro.

In addition, or as an alternative, to one or more of embodiments (a) through (d') in the preceding paragraphs, compounds of Formula 1 include those in which: (g') $R^3$ is $C_{1-3}$ alkyl or $C_{1-3}$ haloalkyl.

In addition, or as an alternative, to one or more of embodiments (a) through (g') in the preceding paragraphs, compounds of Formula 1 include those in which: (h') $R^3$ is methyl.

In addition, or as an alternative, to one or more of embodiments (a) through (h') in the preceding paragraphs, compounds of Formula 1 include those in which: (i') one of $R^6$ and $R^7$ is hydrogen and one of $R^6$ and $R^7$ is $C_{1-3}$ alkyl.

In addition, or as an alternative, to one or more of embodiments (a) through (h') in the preceding paragraphs, compounds of Formula 1 include those in which: (j') one of $R^6$ and $R^7$ is hydrogen and one of $R^6$ and $R^7$ is methyl or ethyl.

In addition, or as an alternative, to one or more of embodiments (a) through (h') in the preceding paragraphs, compounds of Formula 1 include those in which: (k') one of $R^6$ and $R^7$ is hydrogen and one of $R^6$ and $R^7$ is methyl.

In addition, or as an alternative, to one or more of embodiments (a) through (k') in the preceding paragraphs, compounds of Formula 1 include those in which: (l') $R^8$ is —$NH_2$ or methyl, and $R^9$ is selected from halo, —CN, and $C_{1-3}$ haloalkyl.

In addition, or as an alternative, to one or more of embodiments (a) through (k') in the preceding paragraphs, compounds of Formula 1 include those in which: (m') $R^8$ is —$NH_2$ or methyl, and $R^9$ is —CN.

In addition, or as an alternative, to one or more of embodiments (a) through (m') in the preceding paragraphs, compounds of Formula 1 include those in which: (n') $R^{10}$ is —$NH_2$.

In addition, or as an alternative, to one or more of embodiments (a) through (n') in the preceding paragraphs, compounds of Formula 1 include those in which: (o') m is 0.

If (p') $R^6$ and $R^7$ are different, then compounds of Formula 1 include those having stereochemical configuration given by Formula 1A or Formula 1B:

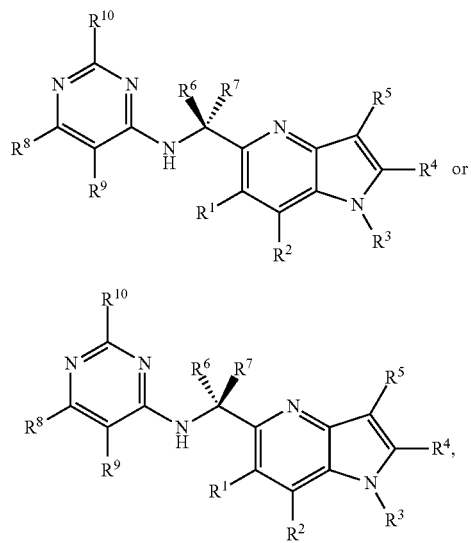

wherein $R^1$, $R^2$, $R^3$, $R^4$, $R^5$, $R^6$, $R^7$, $R^8$, $R^9$, and $R^{10}$ in Formula 1A and Formula 1B are as defined for Formula 1 or as defined in one or more of embodiments (a) through (o') in the preceding paragraphs.

Compounds of Formula 1 and pharmaceutically acceptable salts thereof include embodiments (a) through (p') described in the preceding paragraphs and all compounds specifically named in the examples.

Compounds of Formula 1 may form pharmaceutically acceptable complexes, salts, solvates and hydrates. These salts include acid addition salts (including di-acids) and base salts. Pharmaceutically acceptable acid addition salts include salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include salts derived from bases, including metal cations, such as an alkali or alkaline earth metal cation, as well as amines. Examples of suitable metal cations include sodium, potassium, magnesium, calcium, zinc, and aluminum. Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1, 3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2002).

Pharmaceutically acceptable salts may be prepared using various methods. For example, a compound of Formula 1 may be reacted with an appropriate acid or base to give the desired salt. Alternatively, a precursor of the compound of Formula 1 may be reacted with an acid or base to remove an acid- or base-labile protecting group or to open a lactone or lactam group of the precursor. Additionally, a salt of the compound of Formula 1 may be converted to another salt through treatment with an appropriate acid or base or through contact with an ion exchange resin. Following reaction, the salt may be isolated by filtration if it precipitates from solution, or by evaporation to recover the salt. The degree of ionization of the salt may vary from completely ionized to almost non-ionized.

Compounds of Formula 1 may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

Compounds of Formula 1 may also exist in unsolvated and solvated forms. The term "solvate" describes a molecular complex comprising the compound and one or more pharmaceutically acceptable solvent molecules (e.g., ethanol, isopropanol, etc.). The term "hydrate" is a solvate in which the solvent is water. Pharmaceutically acceptable solvates include those in which the solvent may be isotopically substituted (e.g., $D_2O$, acetone-$d_6$, DMSO-$d_6$).

A currently accepted classification system for solvates and hydrates of organic compounds is one that distinguishes between isolated site, channel, and metal-ion coordinated solvates and hydrates. See, e.g., K. R. Morris (H. G. Brittain ed.) *Polymorphism in Pharmaceutical Solids* (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of Formula 1 may also exist as multi-component complexes (other than salts and solvates) in which the compound (drug) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together. See, e.g., O. Almarsson and M. J. Zaworotko, *Chem. Commun.* (2004) 17:1889-1896. For a general review of multi-component complexes, see J. K. Haleblian, *J. Pharm. Sci.* (1975) 64(8): 1269-88.

When subjected to suitable conditions, compounds of Formula 1 may exist in a mesomorphic state (mesophase or liquid crystal). The mesomorphic state lies between the true crystalline state and the true liquid state (either melt or solution). Mesomorphism arising as the result of a change in temperature is described as "thermotropic" and mesomorphism resulting from the addition of a second component, such as water or another solvent, is described as "lyotropic." Compounds that have the potential to form lyotropic mesophases are described as "amphiphilic" and include molecules which possess a polar ionic moiety (e.g., —$COO^-Na^+$, —$COO^-K^+$, —$SO_3^-Na^+$) or polar non-ionic moiety (such as —$N^-N^+$($CH_3$)$_3$). See, e.g., N. H. Hartshorne and A. Stuart, *Crystals and the Polarizing Microscope* (4th ed, 1970).

Compounds of Formula 1 include all polymorphs and crystal habits, stereoisomers, and tautomers thereof, as well as all isotopically-labeled compounds thereof. The compounds of Formula 1 may be administered as prodrugs or form metabolites.

"Prodrugs" refer to compounds having little or no pharmacological activity that can, when metabolized in vivo, undergo conversion to compounds having desired pharmacological activity. Prodrugs may be prepared by replacing appropriate functionalities present in pharmacologically active compounds with "pro-moieties" as described, for example, in H. Bundgaar, *Design of Prodrugs* (1985). Examples of prodrugs include ester, ether or amide derivatives of compounds of Formula 1 having carboxylic acid, hydroxy, or amino functional groups, respectively. For further discussions of prodrugs, see e.g., T. Higuchi and V. Stella "Pro-drugs as Novel Delivery Systems," *ACS Symposium Series* 14 (1975) and E. B. Roche ed., *Bioreversible Carriers in Drug Design* (1987).

"Metabolites" refer to compounds formed in vivo upon administration of pharmacologically active compounds. Examples include hydroxymethyl, hydroxy, secondary amino, primary amino, phenol, and carboxylic acid derivatives of compounds of Formula 1 having methyl, alkoxy, tertiary amino, secondary amino, phenyl, and amide groups, respectively.

Compounds of Formula 1 include all stereoisomers, whether they are pure, substantially pure, or mixtures, and result from the presence of one or more stereogenic centers, one or more double bonds, or both. Such stereoisomers may also result from acid addition or base salts in which the counter-ion is optically active, for example, when the counter-ion is D-lactate or L-lysine.

Compounds of Formula 1 also include all tautomers, which are isomers resulting from tautomerization. Tautomeric isomerism includes, for example, imine-enamine, keto-enol, oxime-nitroso, and amide-imidic acid tautomerism.

Compounds of Formula 1 may exhibit more than one type of isomerism.

Geometrical (cis/trans) isomers may be separated by conventional techniques such as chromatography and fractional crystallization.

Conventional techniques for preparing or isolating a compound having a specific stereochemical configuration include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of Formula 1 contains an acidic or basic moiety, an acid or base such as tartaric acid or 1-phenylethylamine. The resulting diastereomeric mixture may be separated by chromatography, fractional crystallization, etc., and the appropriate diastereoisomer converted to the compound having the requisite stereochemical configuration. For a further discussion of techniques for separating stereoisomers, see E. L. Eliel and S. H. Wilen, *Stereochemistry of Organic Compounds* (1994).

Compounds of Formula 1 also include all isotopic variations, in which at least one atom is replaced by an atom having the same atomic number, but an atomic mass different from the atomic mass usually found in nature. Isotopes suitable for inclusion in compounds of Formula 1 include, for example, isotopes of hydrogen, such as $^2H$ and $^3H$; isotopes of carbon, such as $^{11}C$, $^{13}C$ and $^{14}C$; isotopes of nitrogen, such as $^{13}N$ and $^{15}N$; isotopes of oxygen, such as $^{15}O$, $^{17}O$ and $^{18}O$; isotopes of sulfur, such as $^{35}S$; isotopes of fluorine, such as $^{18}F$; isotopes of chlorine, such as $^{36}Cl$, and isotopes of iodine, such as $^{123}I$ and $^{125}I$. Use of isotopic variations (e.g., deuterium, $^2H$) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3$H, or $^{14}$C), which may be useful in drug and/or substrate tissue distribution studies. Substitution with positron emitting isotopes, such as $^{11}$C, $^{18}$F, $^{15}$O and $^{13}$N, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations* (1999), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a di-acid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry* (1999) and P. Kocienski, *Protective Groups* (2000).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxyethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

In the schemes, below, substituent identifiers (e.g., $R^1$, $R^2$, $R^3$, etc.) are as defined above for Formula 1. As mentioned earlier, however, some of the starting materials and intermediates may include protecting groups, which are removed prior to the final product. In such cases, the substituent identifier refers to moieties defined in Formula 1 and to those moieties with appropriate protecting groups. For example, a starting material or intermediate in the schemes may include $R^8$ having a potentially reactive amine. In such cases, $R^8$ would include the moiety with or without, say, a Boc or Cbz group attached to the amine.

Scheme A shows general methods for preparing compounds of Formula 1 from a pair of substituted 4-azaindoles (A1, A3). In one of the methods, a 5-aminomethyl-4-azaindole (A1) is reacted with a 6-halopyrimidine derivative (A2, $X^1$ is Cl, Br) in a solvent (e.g., acetonitrile, DMSO, etc.) and in the presence of a base (e.g., tertiary amine such as DIPEA) at elevated temperature (e.g., 75-150° C.). Alternatively, the compound of Formula 1 may be prepared through Pd-catalyzed cross-coupling, i.e., reaction of a 6-bromo-4-azaindole (A3) with a boronic acid or borate, stannane, or amine (A4) under Suzuki, Stille, or Buchwald conditions, respectively. For example, compound A3 may be reacted with an boronic acid or borate (e.g., Y is —B(OR$^{19}$)$_2$, R$^{19}$ is H or C$_{1-4}$ alkyl) in the presence of a palladium catalyst (e.g., Pd(PPh$_3$)$_4$, (PPh$_3$)$_2$PdCl$_2$, PdCl$_2$(dppf), etc.), a base (e.g., KF, Na$_2$CO$_3$, Cs$_2$CO$_3$), and one or more solvents (e.g., dioxane, DMF, H$_2$O, etc.) at elevated temperature (e.g., 90-130° C.). Alternatively, compound A3 may be reacted with an aromatic tin reagent (e.g., Y is —Sn(n-Bu)$_3$) in the presence of a palladium catalyst (e.g., Pd(PPh$_3$)$_4$) and one or more organic solvents (e.g., toluene, dioxane, etc.) at elevated temperature (e.g., 100-150° C.). Compound A3 may also be reacted with an amine (e.g., Y is H) in the presence of a palladium catalyst (e.g., Pd$_2$(dba)$_3$, Pd(OAc)$_2$, PdCl$_2$(dppf), etc.) and an optional ligand (e.g., Xantphos), a stoichiometric amount of base (e.g., NaOt-Bu), and one or more organic solvents (e.g., dioxane, toluene, etc.), at elevated temperature (e.g., about 100° C.). As indicated in Scheme A, when compound 1 is racemic, it may be optionally purified by chiral column chromatography (e.g., supercritical fluid chromatography) or by derivatization with optically-pure reagents as described above, to give individual enantiomers 1A or 1B.

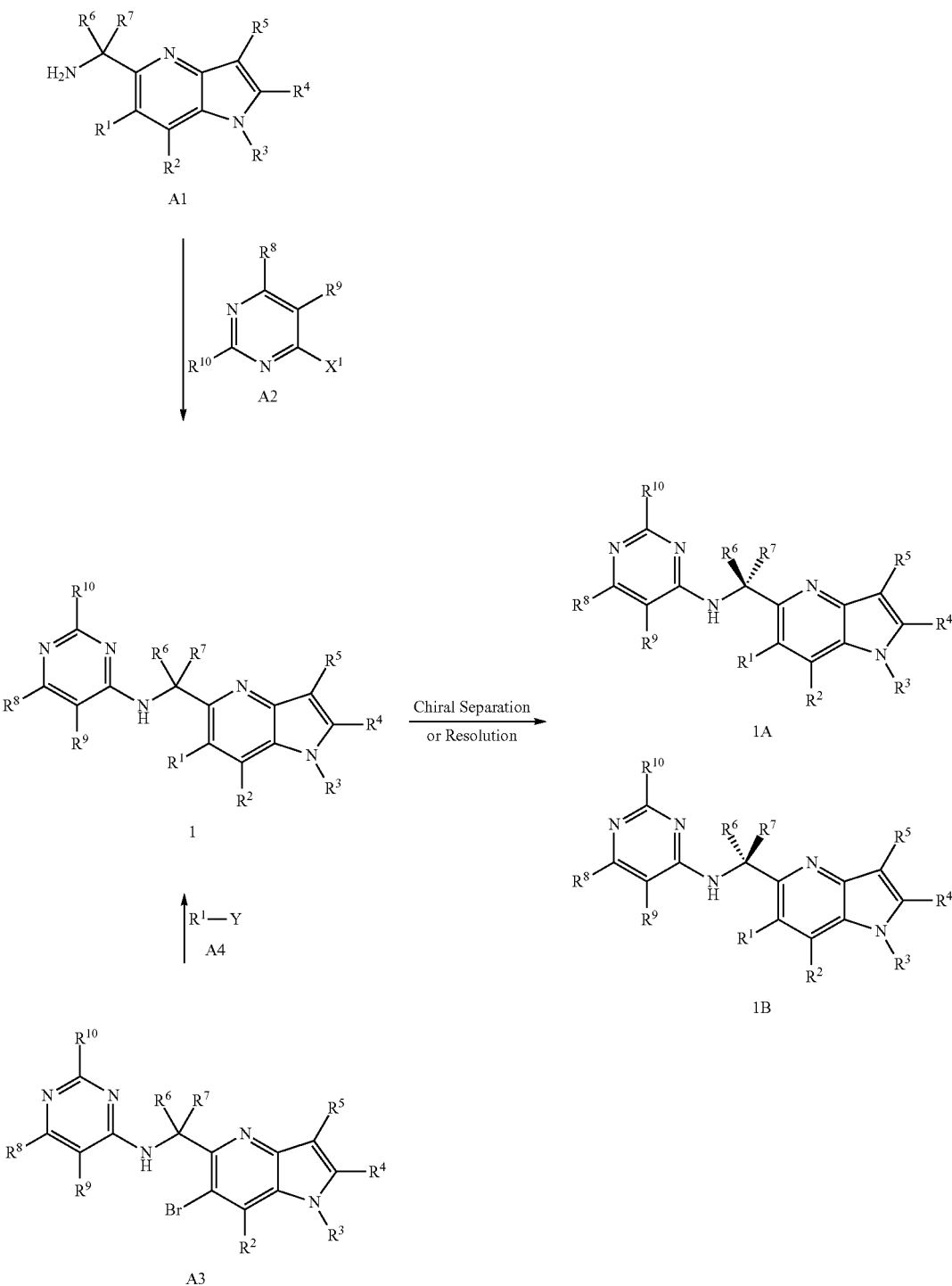

Scheme A

Scheme B shows a general method for preparing substituted 4-azaindoles (compounds A1 and A3) depicted in Scheme A. The method begins with the installation of an amine protecting group (G) on starting material B1, in which for example, 6-bromo-1H-pyrrolo[3,2-b]pyridine is reacted with TsCl in sodium hydride and DMF to give 6-bromo-1-tosyl-1H-pyrrolo[3,2-b]pyridine. Treatment of the resulting protected intermediate B2 with an oxidizing agent (e.g., mCPBA) gives an N-oxide intermediate B3, which undergoes cyanation via, for example, reaction with trimethylsilyl cyanide in the presence of base (e.g., tertiary amine such as $Et_3N$) and DMF. The resulting intermediate B4 is deprotected (e.g., Ts is removed via contact with aq NaOH) and is optionally N-alkylated through reaction with an alkyl halide B6 (e.g., $X^2$ is I) under basic conditions (e.g., NaH in DMF). As in Scheme A, reaction of the resulting bromide B7 with a boronic acid or boronate, stannane, or amine (A4) under Suzuki, Stille, or Buchwald conditions, respectively, gives an $R^1$-substituted 4-azaindole intermediate B8. Treatment of bromide B7 or intermediate B8 with a reducing agent (e.g., borane-THF) or reaction with an alkyl-Grignard or alkyl-lithium reagent followed by reduction with sodium borohydride gives, respectively, an amine intermediate B9 or desired compound A1. As in Scheme A, reaction of the amine intermediate B9 with a 6-halopyrimidine derivative A2 gives desired compound A3.

Scheme C shows an alternative method for preparing intermediate B8 depicted in Scheme B. Although Scheme C uses the same starting material as Scheme B, bromide B1 is instead first reacted with a boronic acid or boronate, stannane, or amine (A4) under Suzuki, Stille, or Buchwald conditions, respectively. The resulting $R^1$-substituted 4-azaindole intermediate C1 is optionally N-alkylated through reaction with an alkyl halide B6 under basic conditions (e.g., NaH in DMF). Treatment of the resulting intermediate C2 with an oxidizing

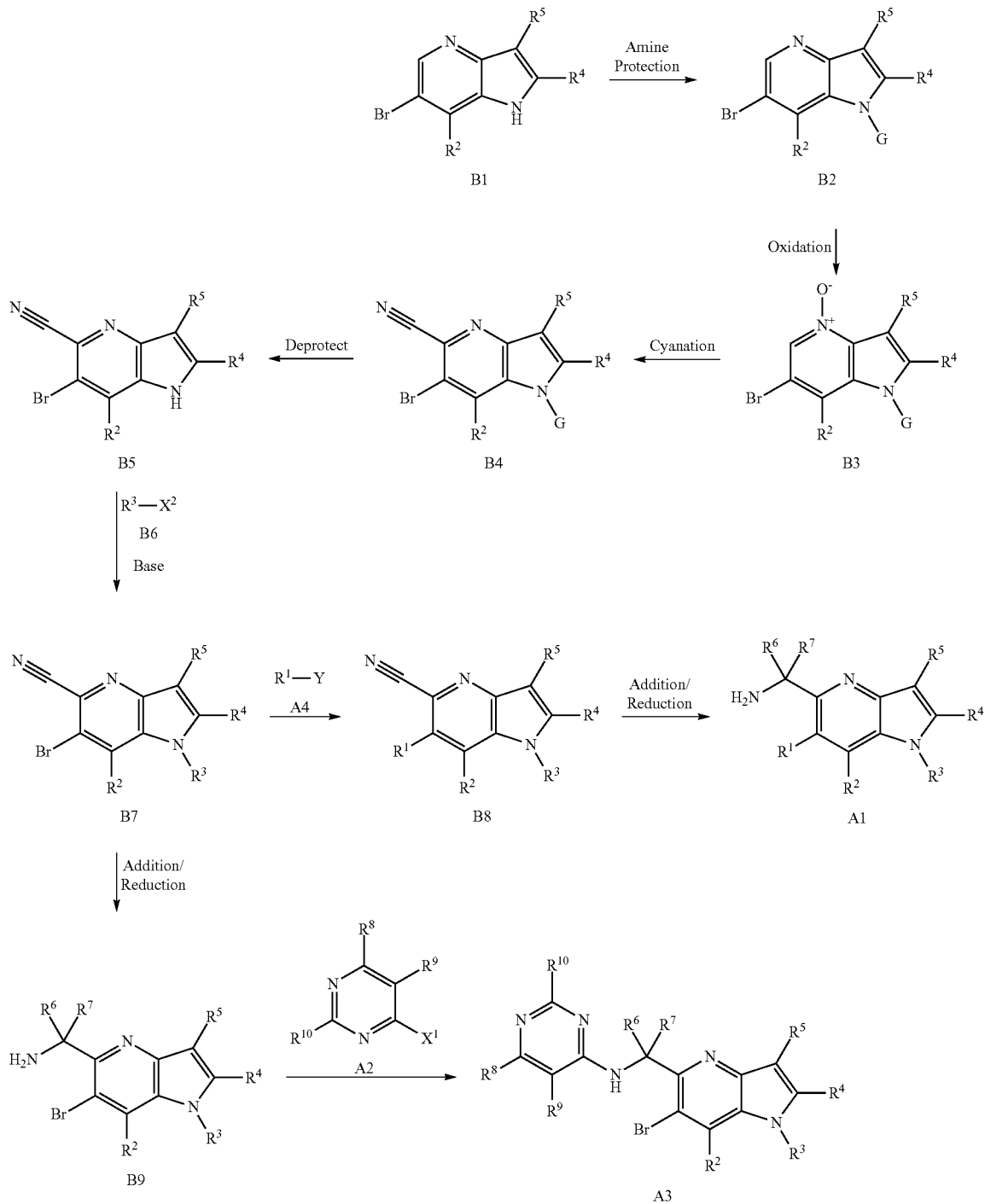

agent (e.g., mCPBA) gives an N-oxide intermediate C3, which undergoes cyanation via, for example, reaction with trimethylsilyl cyanide in the presence of base (e.g., tertiary amine such as Et₃N) and DMF to give desired intermediate B8.

Scheme C

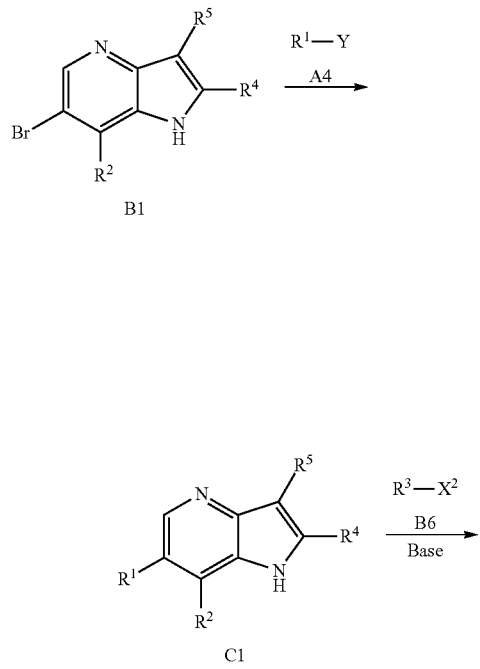

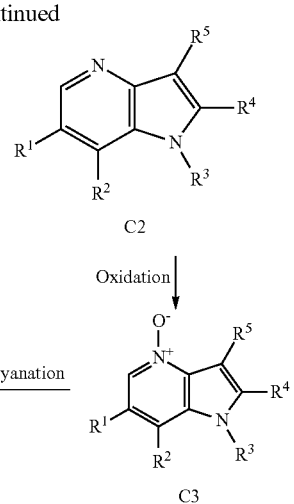

Scheme D shows two additional methods for preparing intermediate B7 depicted in Scheme B. In one of the methods, starting material B1 is optionally N-alkylated through reaction with an alkyl halide B6 under basic conditions (e.g., NaH in DMF). Treatment of the resulting intermediate D1 with an oxidizing agent (e.g., mCPBA) gives an N-oxide intermediate D2, which undergoes cyanation via, for example, reaction with trimethylsilyl cyanide in the presence of base (e.g., tertiary amine such as Et₃N) to give desired intermediate B7. Alternatively, starting material B1 may be first treated with an oxidizing agent to give an N-oxide intermediate D3, which subsequently undergoes cyanation. The resulting nitrile intermediate D4 is optionally N-alkylated through reaction with an alkyl halide B6 under basic conditions to give desired intermediate B7.

Scheme D

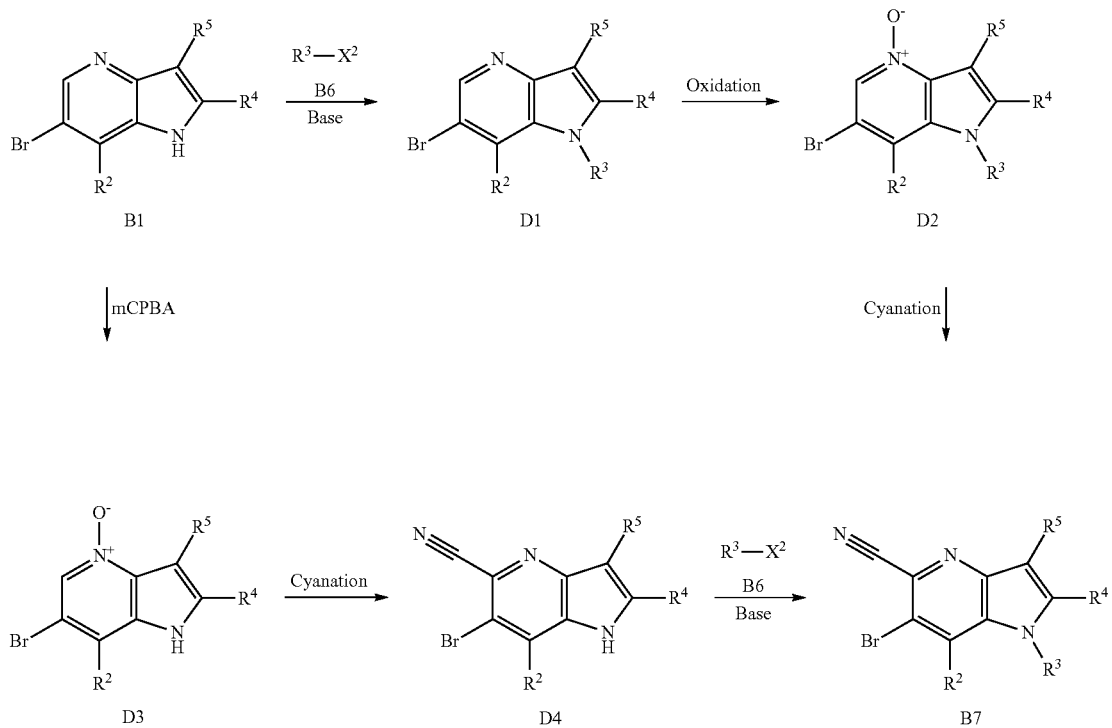

Scheme E shows alternative methods for preparing enantiomers 1A and 1B. Boc-protected intermediate E1 is resolved by chiral separation, diastereomeric salt formation or other methods of resolution, to give enantiomers E2 and E3. Each of these enantiomers may be first reacted with a boronic acid or boronate, stannane, or amine (A4) under Suzuki, Stille, or Buchwald conditions, respectively, or may undergo direct SNAr reaction to give corresponding enantiomer E4 or E6. Deprotection of the Boc-group by treatment with an acid (TFA, HCl, etc.) followed by reaction with pyrimidine derivative A2 in the presence of a base gives corresponding enantiomer 1A or 1B. Alternatively, Boc-protected E2 or E3 may be first reacted with an acid (TFA, HCl, etc.) to give corresponding free amine E5 or E7. Each may be reacted with a boronic acid or boronate, stannane, or amine (A4) under Suzuki, Stille, or Buchwald conditions, respectively, or may undergo direct SNAr reaction to give a corresponding $R^1$-substituted free amine (not shown) which is subsequently reacted with pyrimidine derivative A2 in the presence of a base to give enantiomer 1A or 1B.

Scheme F shows a method for preparing compounds of Formula 1 in which $R^8$ is —$NH_2$ and $R^9$ is —CN. As in Scheme A, bromide starting material B9 is reacted with a boronic acid or boronate, stannane, or amine (A4) under Suzuki, Stille, or Buchwald conditions, respectively, or may undergo direct SNAr reaction, to give an $R^1$-substituted 5-aminomethyl-4-azaindole intermediate F1. Subsequent reaction of amine F1 with amidine F2 (guanidine when $R^{10}$=—$NH_2$) and 2-(bis(methylthio)methylene)malononitrile in the presence of a non-nucleophilic base (e.g., $Et_3N$, pyridine, DIPEA, etc.) and one or more solvents (e.g., ACN, pyridine, DMA, DMF, DMPU, DMSO, NMP, etc.) gives desired compound F3. The conversion of compound F1 to compound F3 is typically carried out at elevated temperature (e.g., from about 60° C. to reflux). As indicated in Scheme F, when compound F3 is racemic, it may be optionally purified by chiral column chromatography (e.g., supercritical fluid chromatography) or by derivatization with optically-pure reagents as described above, to give individual enantiomers F3A or F3B.

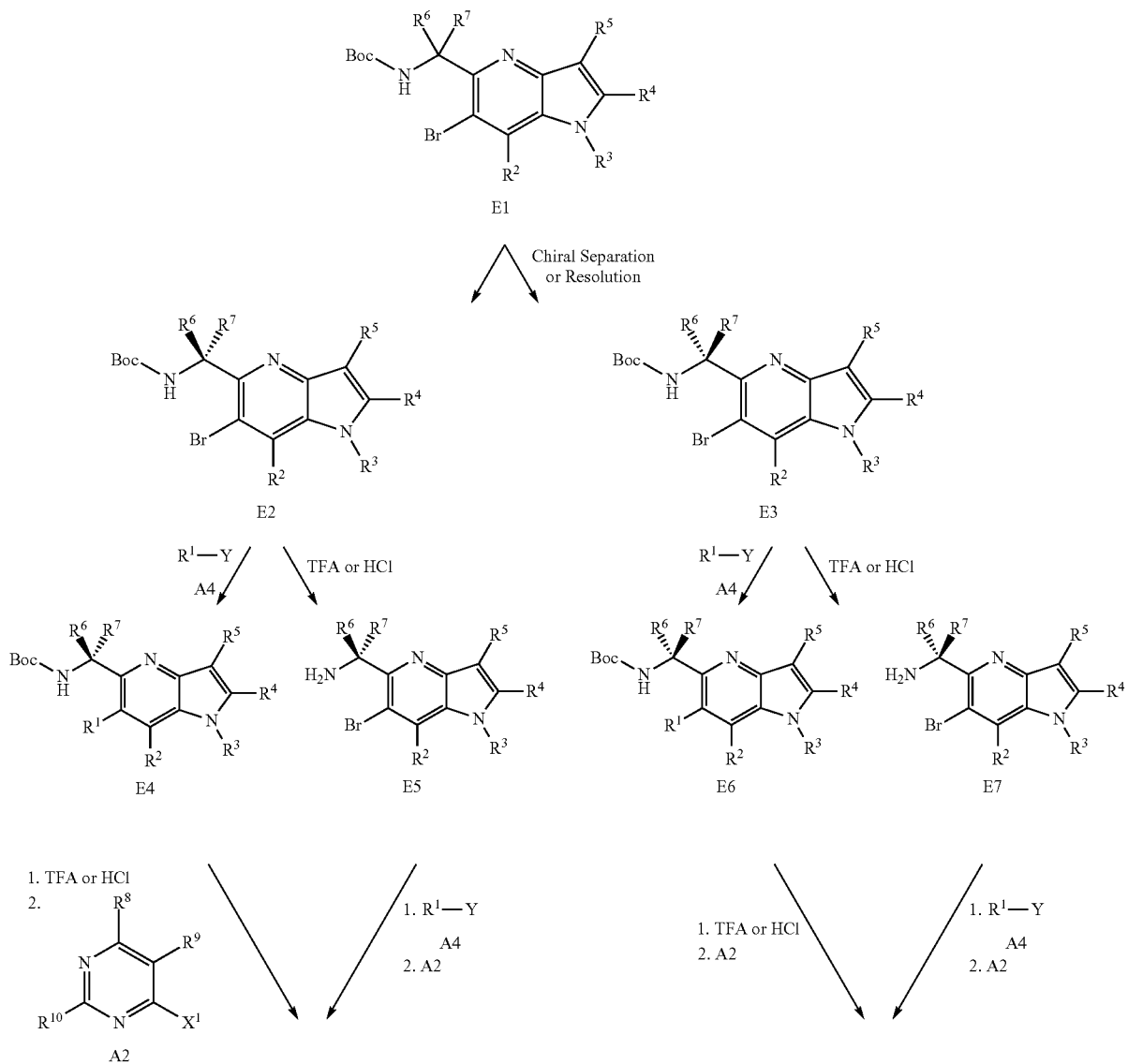

-continued
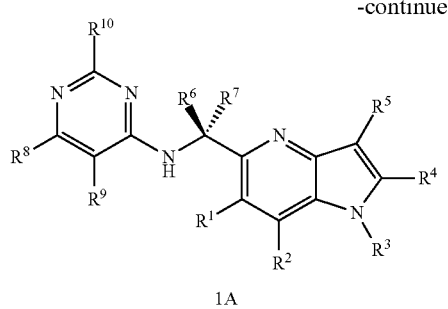
1A
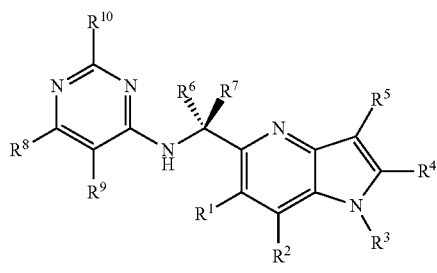
1B
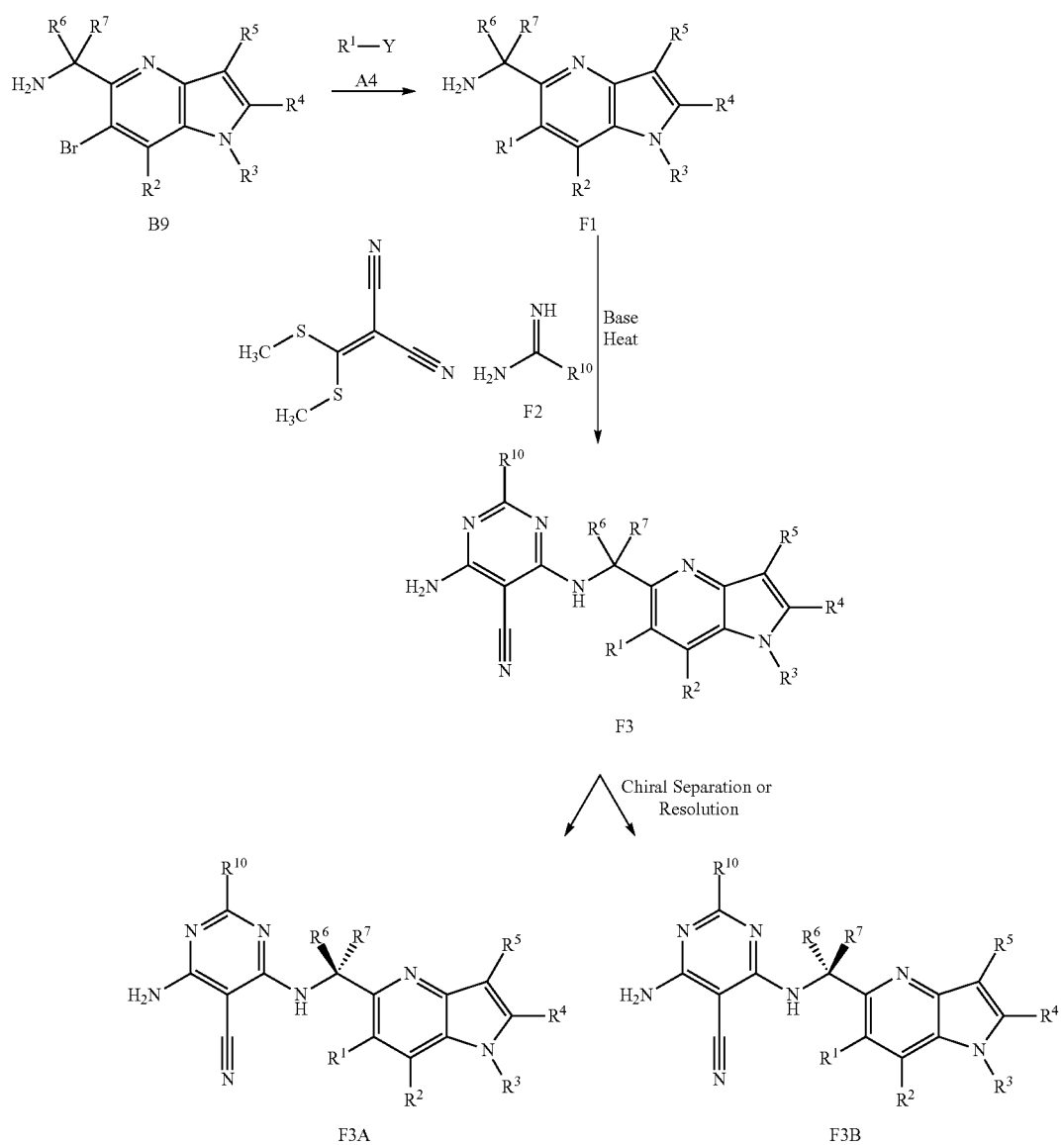
Scheme G shows a method for preparing compounds of Formula 1A in which $R^8$ is —$NH_2$ and $R^9$ is —CN. Racemate bromide starting material B9 is separated by chiral resolution to give the enantiomer G1. As in Scheme A, bromide starting material G1 is reacted with a boronic acid or boronate, stannane, or amine (G2, $R^{1a}$ is a protected $R^1$) under Suzuki, Stille, or Buchwald conditions, respectively, or may undergo direct SNAr reaction, to give an $R^{1a}$-substituted 5-aminomethyl-4-azaindole intermediate G3. Subsequent reaction of amine G3 with compound A2 in the presence of base and one or more solvents (e.g., ACN, pyridine, DMA, DMF, DMPU, DMSO, NMP, etc.) at elevated temperature (e.g., from about 60° C. to reflux) gives intermediate G4, which is deprotected with TFA, HCl, or hydrazine to give compound 1A.

Scheme F, may be resolved to give corresponding pure or substantially pure enantiomers, which may reduce or eliminate the need for downstream chiral separation or resolution depicted in Scheme A and Scheme F, respectively.

Compounds of Formula 1, which include compounds named above, and their pharmaceutically acceptable complexes, salts, solvates and hydrates, should be assessed for their biopharmaceutical properties, such as solubility and

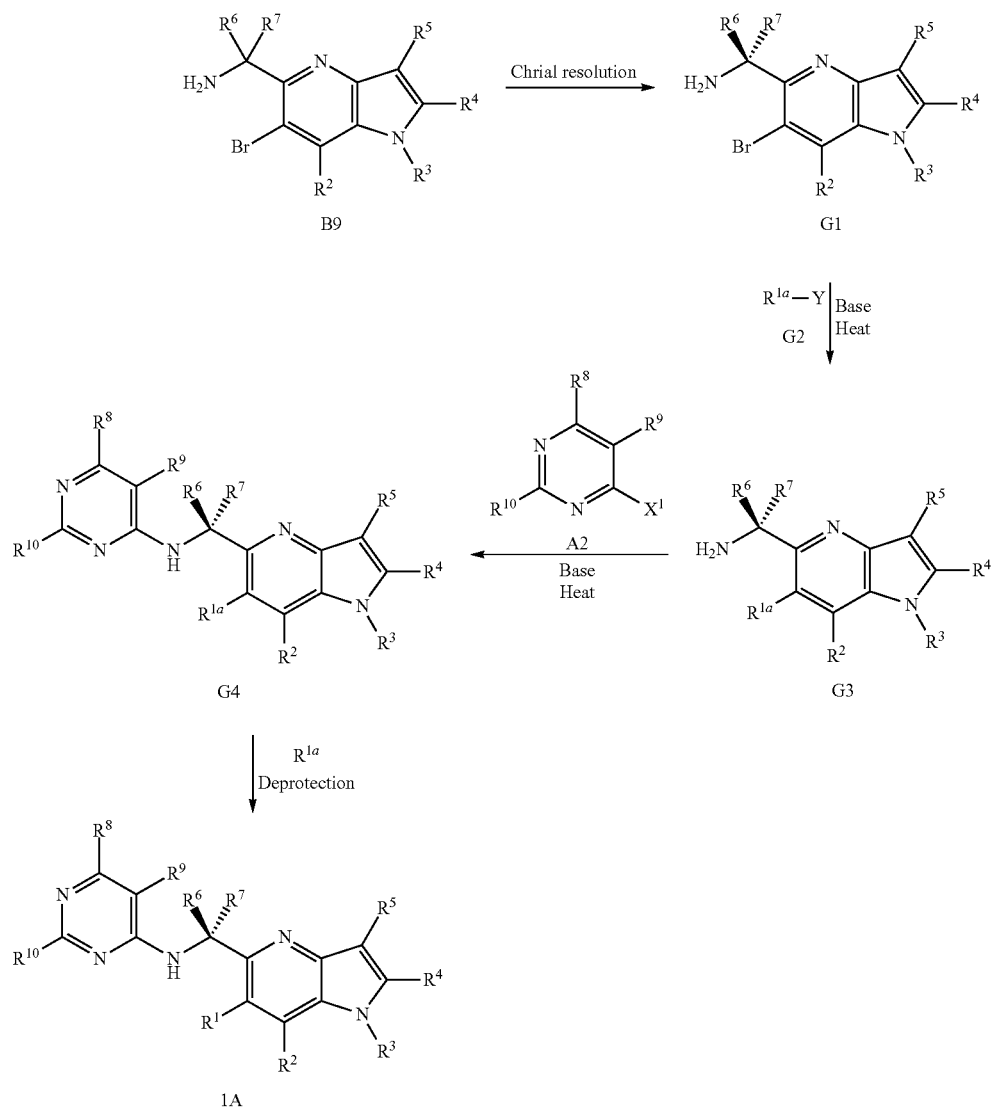

The methods depicted in Schemes A-G may be varied as desired. For example, protecting groups may be added or removed at various steps in the route. In addition, the intermediates may be further elaborated via, for example, alkylation, acylation, hydrolysis, oxidation, reduction, amidation, sulfonation, alkynation, and the like to give the desired final product. Furthermore, any racemic intermediate may be optionally purified by chiral column chromatography (e.g., supercritical fluid chromatography) or by derivatization with optically-pure reagents as described above, to give a desired stereoisomer. Thus, for example, amines A1 or B9 ($R^6$ and $R^7$ are different) in Scheme B or amines B9 or F1 (or both) in solution stability across pH, permeability, and the like, to select an appropriate dosage form and route of administration. Compounds that are intended for pharmaceutical use may be administered as crystalline or amorphous products, and may be obtained, for example, as solid plugs, powders, or films by methods such as precipitation, crystallization, freeze drying, spray drying, evaporative drying, microwave drying, or radio frequency drying.

Compounds of Formula 1 may be administered alone or in combination with one another or with one or more pharmacologically active compounds which are different than the compounds of Formula 1. Generally, one or more these compounds are administered as a pharmaceutical composition (a formulation) in association with one or more pharmaceutically acceptable excipients. The choice of excipients depends on the particular mode of administration, the effect of the excipient on solubility and stability, and the nature of the dosage form, among other things. Useful pharmaceutical compositions and methods for their preparation may be found, for example, in A. R. Gennaro (ed.), *Remington: The Science and Practice of Pharmacy* (20th ed., 2000).

Compounds of Formula 1 may be administered orally. Oral administration may involve swallowing in which case the compound enters the bloodstream via the gastrointestinal tract. Alternatively or additionally, oral administration may involve mucosal administration (e.g., buccal, sublingual, supralingual administration) such that the compound enters the bloodstream through the oral mucosa.

Formulations suitable for oral administration include solid, semi-solid and liquid systems such as tablets; soft or hard capsules containing multi- or nano-particulates, liquids, or powders; lozenges which may be liquid-filled; chews; gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

Compounds of Formula 1 may also be used in fast-dissolving, fast-disintegrating dosage forms such as those described in Liang and Chen, *Expert Opinion in Therapeutic Patents* (2001) 11(6):981-986.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets, Vol.* 1-3 (2d ed., 1990); and D. K. Parikh & C. K. Parikh, *Handbook of Pharmaceutical Granulation Technology*, Vol. 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include anti-oxidants, colorants, flavorants and flavor enhancers, preservatives, salivary stimulating agents, cooling agents, co-solvents (including oils), emollients, bulking agents, anti-foaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14.

Compounds of Formula 1 may also be administered directly into the blood stream, muscle, or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration. Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from about 3 to about 9). For some applications, however, compounds of Formula 1 may be more suitably formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques, such as the incorporation of solubility-enhancing agents. Formulations for parenteral administration may be formulated to be immediate or modified release. Modified release formulations include delayed, sustained, pulsed, controlled, targeted, and programmed release. Thus, compounds of Formula 1 may be formulated as a suspension, a solid, a semi-solid, or a thixotropic liquid for administration as an implanted depot providing modified release of the active compound. Examples of such formulations include drug-coated stents and semi-solids and suspensions comprising drug-loaded poly(DL-lactic-coglycolic) acid (PGLA) microspheres.

Compounds of Formula 1 may also be administered topically, intradermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol. Topical formulations may also include penetration enhancers. See, e.g., Finnin and Morgan, J. Pharm. Sci. 88(10):955-958 (1999).

Other means of topical administration include delivery by electroporation, iontophoresis, phonophoresis, sonophoresis and microneedle or needle-free (e.g. Powderject™ and Bioject™) injection. Formulations for topical administration may be formulated to be immediate or modified release as described above.

Compounds of Formula 1 may also be administered intranasally or by inhalation, typically in the form of a dry powder, an aerosol spray, or nasal drops. An inhaler may be used to administer the dry powder, which comprises the API alone, a powder blend of the API and a diluent, such as lactose, or a mixed component particle that includes the API and a phospholipid, such as phosphatidylcholine. For intranasal use, the powder may include a bioadhesive agent, e.g., chitosan or cyclodextrin. A pressurized container, pump, sprayer, atomizer, or nebulizer, may be used to generate the aerosol spray from a solution or suspension comprising the API, one or more agents for dispersing, solubilizing, or extending the release of the API (e.g., EtOH with or without water), one or more solvents (e.g., 1,1,1,2-tetrafluoroethane or 1,1,1,2,3,3, 3-heptafluoropropane) which serve as a propellant, and an optional surfactant, such as sorbitan trioleate, oleic acid, or an oligolactic acid. An atomizer using electrohydrodynamics may be used to produce a fine mist.

Prior to use in a dry powder or suspension formulation, the drug product is usually comminuted to a particle size suitable for delivery by inhalation (typically 90% of the particles, based on volume, having a largest dimension less than 5 microns). This may be achieved by any appropriate size reduction method, such as spiral jet milling, fluid bed jet milling, supercritical fluid processing, high pressure homogenization, or spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose or starch, and a performance modifier such as L-leucine, mannitol, or magnesium stearate. The lactose may be anhydrous or monohydrated. Other suitable excipients include dextran, glucose, maltose, sorbitol, xylitol, fructose, sucrose, and trehalose.

A suitable solution formulation for use in an atomizer using electrohydrodynamics to produce a fine mist may contain from about 1 µg to about 20 mg of the API per actuation and the actuation volume may vary from about 1 µL to about 100 µL. A typical formulation may comprise one or more compounds of Formula 1, propylene glycol, sterile water, EtOH, and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors, such as menthol and levomenthol, or sweeteners, such as saccharin or sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 µg to about 1000 µg of the API. The overall daily dose will typically range from about 100 µg to about 10 mg which may be administered in a single dose or, more usually, as divided doses throughout the day.

The active compounds may be administered rectally or vaginally, e.g., in the form of a suppository, pessary, or enema. Cocoa butter is a traditional suppository base, but various alternatives may be used as appropriate. Formulations for rectal or vaginal administration may be formulated to be immediate or modified release as described above.

Compounds of Formula 1 may also be administered directly to the eye or ear, typically in the form of drops of a micronized suspension or solution in isotonic, pH-adjusted, sterile saline. Other formulations suitable for ocular and aural administration include ointments, gels, biodegradable implants (e.g. absorbable gel sponges, collagen), non-biodegradable implants (e.g. silicone), wafers, lenses, and particulate or vesicular systems, such as niosomes or liposomes. The formulation may include one or more polymers and a preservative, such as benzalkonium chloride. Typical polymers include crossed-linked polyacrylic acid, polyvinylalcohol, hyaluronic acid, cellulosic polymers (e.g., hydroxypropylmethylcellulose, hydroxyethylcellulose, methyl cellulose), and heteropolysaccharide polymers (e.g., gelan gum). Such formulations may also be delivered by iontophoresis. Formulations for ocular or aural administration may be formulated to be immediate or modified release as described above.

To improve their solubility, dissolution rate, taste-masking, bioavailability, or stability, compounds of Formula 1 may be combined with soluble macromolecular entities, including cyclodextrin and its derivatives and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent, or solubilizer. Alpha-, beta- and gamma-cyclodextrins are commonly used for these purposes. See, e.g., WO 91/11172, WO 94/02518, and WO 98/55148.

As noted above, one or more compounds of Formula 1, including compounds specifically named above, and their pharmaceutically active complexes, salts, solvates and hydrates, may be combined with each other or with one or more other active pharmaceutically active compounds to treat various diseases, disorders or conditions. In such cases, the active compounds may be combined in a single dosage form as described above or may be provided in the form of a kit which is suitable for coadministration of the compositions. The kit comprises (1) two or more different pharmaceutical compositions, at least one of which contains a compound of Formula 1; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed and disclosed compounds is typically in the range of about 0.1 mg to about 3000 mg depending on the route of administration. For example, oral administration may require a total daily dose of from about 1 mg to about 3000 mg, while an intravenous dose may only require a total daily dose of from about 0.1 mg to about 300 mg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., an infant) whose mass falls outside of this weight range.

As noted above, the compounds of Formula 1 may be used to treat diseases, disorders or conditions for which inhibition of PI3Kδ is indicated. Such diseases, disorders or conditions generally relate to any unhealthy or abnormal state in a subject for which the inhibition of PI3Kδ provides a therapeutic or prophylactic benefit. More particularly, such diseases, disorders or conditions may involve the immune system and inflammation, including Type I hypersensitivity (allergic) reactions (allergic rhinitis, allergic asthma, and atopic dermatitis); autoimmune diseases (rheumatoid arthritis, multiple sclerosis, systemic lupus erythematosus, psoriasis, and immune thrombocytopenic purpura); inflammation of the lung (chronic obstructive pulmonary disease, including exacerbation of COPD), graft-versus-host disease, and thrombosis. The compounds of Formula 1 may also be used to treat diseases, disorders or conditions related to abnormal cell growth, including hematological malignancies, such as acute myeloid leukemia, B-cell chronic lymphocytic leukemia, B-cell lymphoma (e.g., mantle cell lymphoma), and T-cell lymphoma (e.g., peripheral T-cell lymphoma), as well as epithelial cancers (i.e., carcinomas), such as lung cancer (small cell lung cancer and non-small cell lung cancer), pancreatic cancer, and colon cancer.

In addition to the hematological malignancies and epithelial cancers noted above, the compounds of Formula 1 may also be used to treat other types of cancer, including leukemia (chronic myelogenous leukemia and chronic lymphocytic leukemia); breast cancer, genitourinary cancer, skin cancer, bone cancer, prostate cancer, and liver cancer; brain cancer; cancer of the larynx, gall bladder, rectum, parathyroid, thyroid, adrenal, neural tissue, bladder, head, neck, stomach, bronchi, and kidneys; basal cell carcinoma, squamous cell carcinoma, metastatic skin carcinoma, osteosarcoma, Ewing's sarcoma, veticulum cell sarcoma, and Kaposi's sarcoma; myeloma, giant cell tumor, islet cell tumor, acute and chronic lymphocytic and granulocytic tumors, hairy-cell tumor, adenoma, medullary carcinoma, pheochromocytoma, mucosal neuromas, intestinal ganglioneuromas, hyperplastic corneal nerve tumor, marfanoid habitus tumor, Wilms' tumor, seminoma, ovarian tumor, leiomyomater tumor, cervical dysplasia, neuroblastoma, retinoblastoma, myelodysplastic syndrome, rhabdomyosarcoma, astrocytoma, non-Hodgkin's lymphoma, malignant hypercalcemia, polycythermia vera, adenocarcinoma, glioblastoma multiforma, glioma, lymphomas, and malignant melanomas, among others.

In addition to cancer, the compounds of Formula 1 may also be used to treat other diseases related to abnormal cell growth, including non-malignant proliferative diseases such as benign prostatic hypertrophy, restinosis, hyperplasia, synovial proliferation disorder, retinopathy or other neovascular disorders of the eye, among others.

The compounds of Formula 1 may also be used to treat autoimmune disorders in addition to those listed above. Such diseases, disorders or conditions include Crohns disease, dermatomyositis, diabetes mellitus type 1, Goodpasture's syndrome, Graves' disease, Guillain-Barré syndrome, Hashimoto's disease, mixed connective tissue damage, myasthenia gravis, narcolepsy, *pemphigus vulgaris*, pernicious anemia, polymyositis, primary biliary cirrhosis, Sjögren's syndrome, temporal arteritis, ulcerative colitis, vasculitis, and Wegener's granulomatosis, among others.

Furthermore, compounds of Formula 1 may be used to treat inflammatory disorders including asthma (child-onset asthma, adult-onset asthma, allergic asthma, exercised-induced asthma, cough-variant asthma, occupational asthma, nocturnal asthma, steroid-resistant asthma, exacerbation of asthma etc.), chronic inflammation, chronic prostatitis, glomerulonephritis, hypersensitivities, inflammatory bowel diseases (ulcerative colitis in addition to Crohn's disease), pelvic inflammatory disease, reperfusion injury, transplant failure or rejection, graft-versus-host disease (including acute or chronic GVHD), vasculitis, and systemic inflammatory response syndrome.

The compounds of Formula 1 may also be used to treat specific diseases that may fall within one or more general disorders described above, including arthritis. In addition to rheumatoid arthritis, Sjögren's syndrome, systemic lupus erythematosus, SLE in children and adolescents, compounds of Formula 1 may also be used to treat other arthritis diseases, including ankylosing spondylitis, avascular necrosis, Behcet's disease, bursitis, calcium pyrophosphate dihyrate crystal deposition disease (pseudo gout), carpal tunnel syndrome, Ehlers-Danlos syndrome, fibromyalgia, Fifth disease, giant cell arteritis, gout, juvenile dermatomyositis, juvenile rheumatoid arthritis, juvenile spondyloarthopathy, Lyme disease, Marfan syndrome, myositis, osteoarthritis, osteogenesis imperfect, osteoporosis, Paget's disease, psoriatic arthritis, Raynaud's phenomenon, reactive arthritis, reflex sympathetic dystrophy syndrome, *scleroderma*, spinal stenosis, Still's disease, and tendinitis, among others.

The claimed and disclosed compounds may be combined with one or more other pharmacologically active compounds or therapies for the treatment of one or more diseases, disorders or conditions for which PI3Kδ is indicated, including diseases, disorders or conditions involving the immune system, inflammation, and abnormal cell growth. For example, compounds of Formula 1, which include compounds specifically named above, and their pharmaceutically acceptable complexes, salts, solvates and hydrates, may be administered simultaneously, sequentially or separately in combination with one or more compounds or therapies for treating arthritis, including rheumatoid arthritis and osteoarthritis, and for treating asthma, graft-versus-host disease, or cancer, including hematological malignancies, such as acute myeloid leukemia, B-cell chronic lymphocytic leukemia, B-cell lymphoma, and T-cell lymphoma, and carcinomas, such as lung cancer, pancreatic cancer, and colon cancer. Such combinations may offer significant therapeutic advantages, including fewer side effects, improved ability to treat underserved patient populations, or synergistic activity.

For example, when used to treat arthritis, the compounds of Formula 1 may be combined with one or more nonsteroidal anti-inflammatory drugs (NSAIDs), analgesics, corticosteroids, biological response modifiers, and protein-A immunoadsorption therapy. Alternatively or additionally, when treating rheumatoid arthritis, the compounds of Formula 1 may be combined with one or more disease modifying anti-rheumatic drugs (DMARDs), and when treating osteoarthritis, the compounds of Formula 1 may be combined with one or more osteoporosis agents.

Representative NSAIDs include apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac. Representative analgesics include acetaminophen and morphine sulfate, as well as codeine, hydrocodone, oxycodone, propoxyphene, and tramadol, all with or without acetaminophen. Representative corticosteroids include betamethasone, cortisone acetate, dexamethasone, hydrocortisone, methylprednisolone, prednisolone, and prednisone. Representative biological response modifiers include TNF-α inhibitors, such as adalimumab, etanercept, and infliximab; selective B-cell inhibitors, such as rituximab; IL-1 inhibitors, such as anakinra, and selective costimulation modulators, such as abatacept.

Representative DMARDs include auranofin (oral gold), azathioprine, chlorambucil, cyclophosamide, cyclosporine, gold sodium thiomalate (injectable gold), hydroxychloroquine, leflunomide, methotrexate, minocycline, myophenolate mofetil, penicillamine, and sulfasalazine. Representative osteoporosis agents include bisphosphonates, such as alendronate, ibandronate, risedronate, and zoledronic acid; selective estrogen receptor modulators, such as droloxifene, lasofoxifene, and raloxifene; hormones, such as calcitonin, estrogens, and parathyroid hormone; and immunosuppressant agents such as azathioprine, cyclosporine, and rapamycin.

Particularly useful combinations for treating rheumatoid arthritis include a compound of Formula 1 and methotrexate; a compound of Formula 1 and one or more biological response modifiers, such as leflunomide, etanercept, adalimumab, and infliximab; or a compound of Formula 1, methotrexate, and one or more biological response modifiers, such as leflunomide, etanercept, adalimumab, and infliximab.

For the treatment of thrombis and restensosis, the compounds of Formula 1 may be combined with one or more cardiovascular agents such as calcium channel blockers, statins, fibrates, beta-blockers, ACE inhibitors, and platelet aggregation inhibitors.

For the treatment of asthma, the compounds of Formula 1 may be combined with one or more long-term asthma control medications, including inhaled corticosteroids, leukotriene modifiers, long-acting beta agonists, combination inhalers, and theophylline. Representative inhaled corticosteroids include beclomethasone, budesonide, ciclesonide, flunisolide, fluticasone, and mometasone; representative leukotriene modifiers include montelukast, zafirlukast, and zileuton; and representative long-acting beta agonists include salmeterol and formoterol, which are typically administered in combination with an inhaled corticosteroid. Combination inhalers contain a long-acting beta agonist and a corticosteroid, such as fluticasone-salmeterol, budesonide-formoterol, and mometasone-formoterol. The compounds of Formula 1 may also be combined with allergy medications, including allergy shots which reduce the immune system's response to particular allergens, with omalizumab, and with other allergy medications, such as oral and nasal spray antihistamines and decongestants, corticosteroid and cromolyn nasal sprays.

For the treatment (including prophylaxis) of acute or chronic graft-versus-host disease, the compounds of Formula 1 may be combined with one or more compounds including immunosuppressive drugs, immunomodulating agents, including thalidomide, photoactive agents, antineoplastic agents, monoclonal antibodies, polyvalent antibodies or immunoglobulins, and tumor necrosis factor inhibitors. Representative immunosuppressive drugs include corticosteroids, cyclosporine, methylprednisolone, mycophenolate mofetil, prednisone, rapamycin, tacrolimus, and antithymocyte globulin; representative photoactive agents include psoralen and its derivatives, including methoxsalen, and psoralen plus ultraviolet A treatment. Representative antineoplastic agents include methotrexate, which is typically administered with cyclosporine or tacrolimus, and azathioprine, which is typically administered with steroids and cyclosporine, as well as denileukin and pentostatin. Representative monoclonal antibodies include anti-TNF-α antibodies, such as infliximab, anti-CD3 antibodies, such as muromonab-CD3, otelixizumab, teplizumab, and visilizumab, and anti-CD5 antibodies. Other monoclonal antibodies include anti-CD20 antibodies, such as ibritumomab, ofatumumab, rituximab, tiuxetan, tositumomab, and veltuzumab, anti-CD52 antibodies, such as alemtuzumab, and anti-IL-2 antibodies, such as daclizumab. Representative polyvalent antibodies and immunoglobulins include antithymocyte globulin-equine and human intravenous immune globulin. Representative TNF inhibitors include etanercept.

The compounds of Formula 1 may also be combined with one or more compounds or therapies for treating cancer. These include chemotherapeutic agents (i.e., cytotoxic or antineoplastic agents) such as alkylating agents, antibiotics, antimetabolic agents, plant-derived agents, and topoisomerase inhibitors, as well as molecularly targeted drugs which block the growth and spread of cancer by interfering with specific molecules involved in tumor growth and progression. Molecularly targeted drugs include both small molecules and biologics.

Representative alkylating agents include bischloroethylamines (nitrogen mustards, e.g., chlorambucil, cyclophosphamide, ifosfamide, mechlorethamine, melphalan, and uracil mustard); aziridines (e.g., thiotepa); alkyl alkone sulfonates (e.g., busulfan); nitrosoureas (e.g., carmustine, lomustine, and streptozocin); nonclassical alkylating agents (e.g., altretamine, dacarbazine, and procarbazine); and platinum compounds (e.g., carboplatin, cisplatin, nedaplatin, oxaliplatin, satraplatin, and triplatin tetranitrate).

Representative antibiotic agents include anthracyclines (e.g., aclarubicin, amrubicin, daunorubicin, doxorubicin, epirubicin, idarubicin, pirarubicin, valrubicin, and zorubicin); anthracenediones (e.g., mitoxantrone and pixantrone); and *streptomyces* (e.g., actinomycin, bleomycin, dactinomycin, mitomycin C, and plicamycin).

Representative antimetabolic agents include dihydrofolate reductase inhibitors (e.g., aminopterin, methotrexate, and pemetrexed); hymidylate synthase inhibitors (e.g., raltitrexed and pemetrexed); folinic acid (e.g., leucovorin); adenosine deaminase inhibitors (e.g., pentostatin); halogenated/ribonucleotide reductase inhibitors (e.g., cladribine, clofarabine, and fludarabine); thiopurines (e.g., thioguanine and mercaptopurine); thymidylate synthase inhibitors (e.g., fluorouracil, capecitabine, tegafur, carmofur, and floxuridine); DNA polymerase inhibitors (e.g., cytarabine); ribonucleotide reductase inhibitors (e.g., gemcitabine); hypomethylating agent (e.g., azacitidine and decitabine); and ribonucleotide reductase inhibitor (e.g., hydroxyurea); and an asparagine depleter (e.g., asparaginase)

Representative plant-derived agents include *vinca* alkaloids (e.g., vincristine, vinblastine, vindesine, vinzolidine, and vinorelbine), podophyllotoxins (e.g., etoposide and teniposide), and taxanes (e.g., docetaxel, larotaxel, ortataxel, paclitaxel, and tesetaxel).

Representative type I topoisomerase inhibitors include camptothecins, such as belotecan, irinotecan, rubitecan, and topotecan. Representative type II topoisomerase inhibitors include amsacrine, etoposide, etoposide phosphate, and teniposide, which are derivatives of epipodophyllotoxins.

Molecularly targeted therapies include biologic agents such as cytokines and other immune-regulating agents. Useful cytokines include interleukin-2 (IL-2, aldesleukin), interleukin 4 (IL-4), interleukin 12 (IL-12), and interferon, which includes more than 23 related subtypes. Other cytokines include granulocyte colony stimulating factor (CSF) (filgrastim) and granulocyte macrophage CSF (sargramostim). Other immuno-modulating agents include *bacillus* Calmette-Guerin, levamisole, and octreotide; monoclonal antibodies against tumor antigens, such as trastruzumab and rituximab; and cancer vaccines, which induce an immune response to tumors.

In addition, molecularly targeted drugs that interfere with specific molecules involved in tumor growth and progression include inhibitors of epidermal growth factor (EGF), transforming growth factor-alpha (TGF$_\alpha$), TGF$_\beta$, heregulin, insulin-like growth factor (IGF), fibroblast growth factor (FGF), keratinocyte growth factor (KGF), colony stimulating factor (CSF), erythropoietin (EPO), interleukin-2 (IL-2), nerve growth factor (NGF), platelet-derived growth factor (PDGF), hepatocyte growth factor (HGF), vascular endothelial growth factor (VEGF), angiopoietin, epidermal growth factor receptor (EGFR), human epidermal growth factor receptor 2 (HER2), HER4, insulin-like growth factor 1 receptor (IGF1R), IGF2R, fibroblast growth factor 1 receptor (FGF1R), FGF2R, FGF3R, FGF4R, vascular endothelial growth factor receptor (VEGFR), tyrosine kinase with immunoglobulin-like and epidermal growth factor-like domains 2 (Tie-2), platelet-derived growth factor receptor (PDGFR), Abl, Bcr-Abl, Raf, FMS-like tyrosine kinase 3 (FLT3), c-Kit, Src, protein kinase c (PKC), tropomyosin receptor kinase (Trk), Ret, mammalian target of rapamycin (mTOR), Aurora kinase, polo-like kinase (PLK), mitogen activated protein kinase (MAPK), mesenchymal-epithelial transition factor (c-MET), cyclin-dependant kinase (CDK), Akt, extracellular signal-regulated kinases (ERK), poly(ADP) ribose polymerase (PARP), and the like.

Specific molecularly targeted drugs include selective estrogen receptor modulators, such as tamoxifen, toremifene, fulvestrant, and raloxifene; antiandrogens, such as bicalutamide, nilutamide, megestrol, and flutamide; and aromatase inhibitors, such as exemestane, anastrozole, and letrozole. Other specific molecularly targeted drugs include agents which inhibit signal transduction, such as imatinib, dasatinib, nilotinib, trastuzumab, gefitinib, erlotinib, cetuximab, lapatinib, panitumumab, and temsirolimus; agents that induce apoptosis, such as bortezomib; agents that block angiogenesis, such as bevacizumab, sorafenib, and sunitinib; agents that help the immune system destroy cancel cells, such as rituximab and alemtuzumab; and monoclonal antibodies which deliver toxic molecules to cancer cells, such as gemtuzumab ozogamicin, tositumomab, 131I-tositumoab, and ibritumomab tiuxetan.

Biological Activity

The activity of compounds as PI3Kδ inhibitors may be determined by a variety of methods, including in vitro and in vivo methods. The following in vitro assay measures a test compound's ability to inhibit PI3Kδ-mediated phosphorylation of PIP2 and ATP.

Recombinant GST-tagged PIK3CD is purchased from Invitrogen (Part Number: PV5274). The protein is full length and co-expressed with untagged PIK3R1, phosphoinositide-3-kinase regulatory subunit 1 (p85α). The protein is stored at −20° C. in 50 mM TRIS (pH 7.5), 150 mM NaCl, 0.5 mM EDTA, 0.02% Triton® X-100, 2 mM DTT, and 50% glycerol.

A modified PIK3CD Adapta® assay (Invitrogen, Carlsbad, Calif.) is used to measure PI3Kδ inhibition of the example compounds. The assay has two phases. In the first phase, kinase reaction components, which include the enzyme (PIK3CD), substrates (PIP2, ATP), test compound (inhibitor), and assay buffer are added to each well, and the reaction is allowed to incubate for a pre-determined period of time. After reaction, a detection solution composed of a Eu (europium)-labeled anti-ADP antibody, Alexa Fluor® 647-labeled ADP tracer, and EDTA (to stop the kinase reaction) is added to each assay well. In this second phase, ADP formed by the kinase reaction displaces the Alexa Fluor® 647-labeled ADP tracer from the antibody, resulting in a decrease in time-resolved fluorescence resonance energy transfer (TR-FRET) signal. In the presence of the inhibitor, the amount of ADP formed by the kinase reaction is reduced, and the resulting intact antibody-tracer interaction maintains a high TR-FRET signal.

The assay uses black Greiner® 384-well plates (784076). The reaction buffer contains 50 mM Hepes (pH 7.5), 3 mM MgCl$_2$, 1 mM EGTA, 100 mM NaCl, 0.03% CHAPS; 2 mM DTT is added fresh prior to each experiment. Enzyme (4 μL, estimated 1.5 nM in buffer) is first added to the wells of the plate. Next, test compounds (2 μL) from a source plate (5% dilution plate) are introduced into the wells. The final DMSO concentration in each assay well is 1%. The dilution plate contains 5% DMSO in the bottom half of columns 23 and 24, which serve as negative (non-inhibited) controls; the top half contains a known inhibitor concentration (positive control) that gives >98% inhibition of the kinase reaction. Other wells contain test compounds serially diluted across the plate 11 times for a total of 12 data points. The kinase reactions are carried out at room temperature and are initiated by the addition of 4 μL of solution containing 2 μM ATP and 50 μM PIP2. Each reaction is stopped after 1 hour±10 minutes via addition of 10 μM stop solution, which contains a final assay concentration of 3 nM Alexa Fluor® 647-labeled ADP tracer, 2 nM Eu-anti-ADP Antibody, and 10 mM EDTA. After allowing the solutions to equilibrate for 30±10 minutes, a PHERAstar plate reader is used to excite the Eu donor (at 337 nm) and to detect emission from the Alexa Fluor® 647 at 665 nm. This emission signal is referenced or "ratioed" to the emission from Eu at 620 nm. The emission ratio (665 nm/620 nm) from each well is collected and converted to percent conversion using a standard curve for the assay conditions: % conversion=B*(C+A−emission ratio)/(emission ratio−C), where "A" and "C" are the maximum and minimum values of the emission ratio obtained from the standard curve of emission ratio vs. % conversion (ATP-ADP); "B" is the emission ratio corresponding to the % conversion at the $EC_{50}$ value for the ADP Tracer-Eu anti-ADP antibody complex. The percent inhibition for a given inhibitor concentration is computed from % conversion for the reaction and for the positive and negative controls. Corresponding $IC_{50}$ values (molar concentration at 50% inhibition) are calculated by non-linear curve fitting of the compound concentrations and values of percent inhibition to the standard $IC_{50}$ equation.

Aqueous Solubility

The aqueous solubility of the compounds may be assessed using kinetic or thermodynamic solubility assays. Testing media for both assays are prepared as follows:

JP1 (Japan Pharmacopoeia $1^{st}$ fluid for dissolution): In a 1 L volumetric flask, dissolve 2.0 g sodium chloride in about 500 mL deionized water. Add 84 mL of 1M hydrochloric acid and dilute to volume with deionized water. Mix thoroughly.

JP2 (Japan Pharmacopoeia $2^{nd}$ fluid for dissolution): In a 1 L volumetric flask dissolve 6.806 g of anhydrous potassium phosphate monobasic in about 500 mL of deionized water. Add 23.6 mL of 1M sodium hydroxide and dilute to volume with deionized water. Mix thoroughly.

GCDC (20-mM sodium glycochenodeoxycholate in JP2): In a 50 mL volumetric flask, dissolve 0.475 g of sodium glycochenodeoxycholate with ~30 mL JP2. Dilute to volume with additional JP2. Mix thoroughly.

Other pH buffers between pH 2-6 can also be prepared as additional testing media.

A. Kinetic Solubility Assay

Testing compounds as 10 mM solution in 100% DMSO are dispensed in quadruplets at 5 µL each into 96-well plate (V-shaped bottom, 500 µL well size) for calibration standard (standard plate), and in triplicates per testing medium at 4 µL each into a separate 96-well plate (sample plate). Testing medium (196 µL) is added to the sample plate (triplicates per medium). The plate is then sealed with a cap mat, and equilibrated overnight on a shaker at room temperature (19-23° C.). After equilibration, the samples in the 96-well plate are transferred to a 96-well filter plate (1 µm, fiber glass filter membrane) and centrifuge-filtered into a new 96-well sample plate (sample filtrate plate). The calibration standards are prepared by adding 195 µL of standard diluent into the standard plate (quadruplets), cap-mat sealed and equilibrated for 2 hours by vigorous shaking on a shaker. The default diluent for standards is 10% DMSO in acetonitrile. Alternative diluents such as 1:1 DMA/water as well as 1:1 0.1M HCl/water may also be used depending on the solubility behavior of the compounds. The standard plate and sample filtrate plate are then analyzed by HPLC. The calibration response factor is calculated by dividing the average compound peak area from quadruplet standards by 250 (the concentration of standard in µM). The sample solubility in a test medium (in µM) is calculated by dividing the average compound peak area from triplicate samples by the response factor of the corresponding calibration standard.

B. Thermodynamic Solubility Assay

Typically the compounds to be assayed are received as neat powders, but may occasionally be oils. About 3 mg of compound is weighed into an HPLC vial. Testing medium (0.5 mL) is then added to the compound vial. The vial is sealed with a screw-on cap and placed in an incubator set at 37° C. with orbital shaking at 150 RPM for overnight equilibration. At the end of equilibration, the final pH is measured, and whether the compound is totally dissolved (clear solution) or not (solid in vial) is recorded. Then the sample mixture is transferred to a centrifuge tube with filter insert (0.45 µm nylon filter) and centrifuge filtered. The filtrate is diluted appropriately (2 to 50× dilution) before HPLC analysis. A calibration standard is prepared by dissolving ~5 mg of compound in diluent and q.s. to volume in a 20 mL volumetric flask. A separate QC standard is prepared at about the same concentration. The default diluent is 1:1 acetonitrile/water. Alternative diluents such as 1:1 DMA/water and other mixtures may also be used depending on the solubility behavior of the compound. The calibration response factor is calculated by dividing the standard peak area with standard concentration. The sample solubility in a test medium is calculated by dividing the sample peak area with the corresponding standard response factor and multiplied by sample dilution factor. The response factor from QC standard is also calculated and compared with calibration standard. If the response factors of the calibration and QC standard differ by more than 5%, new calibration and QC standards should be prepared and samples are reanalyzed with new standards.

EXAMPLES

The following examples are intended to be illustrative and non-limiting, and represent specific embodiments of the present invention.

$^1$H Nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: $CDCl_3$ (deuterochloroform), DMSO-$d_6$ (deuterodimethylsulfoxide), $CD_3OD$ (deuteromethanol), $CD_3CN$ (deuteroacetonitrile), and THF-$d_8$ (deuterotetrahydrofuran). The mass spectra (M+H) were recorded using either electrospray ionization (ESI-MS) or atmospheric pressure chemical ionization (APCI-MS).

Where indicated, products of certain preparations and examples are purified by mass-triggered HPLC (Pump: Waters™ 2525; MS: ZQ™; Software: MassLynx™), flash chromatography or preparative thin layer chromatography (TLC). Reverse phase chromatography is typically carried out on a column (e.g., Gemini™ 5µ C18 110A, Axia™ 30×75 mm, 5µ) under acidic conditions ("acid mode") eluting with ACN and water mobile phases containing 0.035% and 0.05% trifluoroacetic acid (TFA), respectively, or under basic conditions ("basic mode") eluting with water and 20/80 (v/v) water/acetonitrile mobile phases, both containing 10 mM $NH_4HCO_3$. Preparative TLC is typically carried out on silica gel 60 $F_{254}$ plates. After isolation by chromatography, the solvent is removed and the product is obtained by drying in a centrifugal evaporator (e.g., GeneVac™), rotary evaporator, evacuated flask, etc. Reactions in an inert (e.g., nitrogen) or reactive (e.g., $H_2$) atmosphere are typically carried out at a pressure of about 1 atmosphere (14.7 psi).

Preparation 1: tert-Butyl (S)-4-(5-(1-aminoethyl)-1-methyl-1H-pyrrolo[3,2-b]pyridin-6-yl)piperazine-1-carboxylate

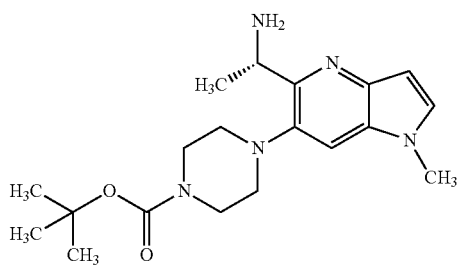

To a 50 mL pear flask were added tert-butyl piperazine-1-carboxylate (2.44 g, 12.7 mmol) and (S)-1-(6-bromo-1-methyl-1H-pyrrolo[3,2-b]pyridin-5-yl)ethanamine (1.54 g, 6.06 mmol) in 1,4-dioxane (15 mL). To this solution was added potassium 2-methylpropan-2-olate (1 M in THF) (13.3 mL, 13.3 mmol), and the resulting mixture was heated to 90° C. for 45 minutes. After cooling for 10 minutes, the red mixture was poured into saturated NaHCO$_3$ (300 mL) and then extracted with EtOAc (3×). The combined organic layers were dried over MgSO$_4$, filtered, and concentrated in vacuo to give crude product, which was purified by preparative HPLC (acid mode, 25-65% ACN/water gradient). The product-containing fractions were combined, concentrated in vacuo, and then partitioned between saturated NaHCO$_3$ and EtOAc. The combined organic layers were dried over MgSO$_4$, filtered, and concentrated to give the title compound (872 mg, 40.0%). ESI-MS m/z [M+H]$^+$ calc'd for $C_{19}H_{29}N_5O_2$, 360. found 360.

Preparation 2: tert-Butyl (S)-4-(5-(1-((2-amino-5-cyano-6-methylpyrimidin-4-yl)amino)ethyl)-1-methyl-1H-pyrrolo[3,2-b]pyridin-6-yl)piperazine-1-carboxylate

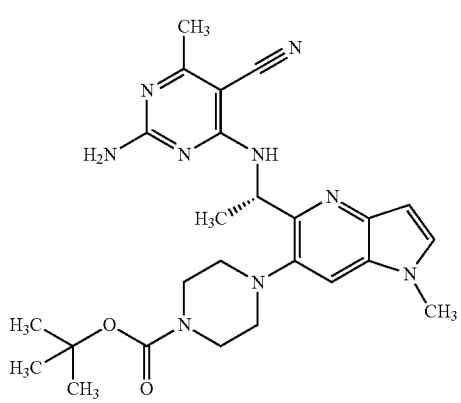

To a 50 mL pear flask were added tert-butyl (S)-4-(5-(1-aminoethyl)-1-methyl-1H-pyrrolo[3,2-b]pyridin-6-yl)piperazine-1-carboxylate (0.85 g, 2.37 mmol) and 2-amino-4-chloro-6-methylpyrimidine-5-carbonitrile (0.638 g, 3.78 mmol) in DMSO (12 mL). Triethylamine (1.65 mL, 11.8 mmol) was added to the mixture which was then heated to 85° C. for three hours. The reaction mixture was partitioned between saturated NaHCO$_3$ and ethyl acetate. The aqueous layer was extracted with ethyl acetate. The organic layers were combined, dried over MgSO$_4$, filtered, and concentrated. The crude product was purified by column chromatography (SiO$_2$, 25-100% EtOAc/heptane gradient) to give the title compound as an off-white solid (0.97 g, 83%). ESI-MS m/z [M+H]$^+$ calc'd for $C_{25}H_{33}N_9O_2$, 492. found 492.

Preparation 3: tert-Butyl (S)-4-(5-(1-aminoethyl)-1-methyl-1H-pyrrolo[3,2-b]pyridin-6-yl)-1,4-diazepane-1-carboxylate

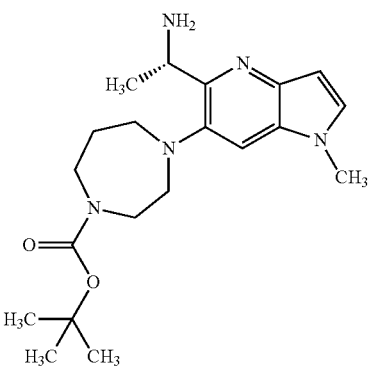 [SMILES: C[C@H](N)c1nc2ccn(C)c2cc1N1CCCN(C(=O)OC(C)(C)C)CC1]

To a 50 mL pear flask were added (S)-1-(6-bromo-1-methyl-1H-pyrrolo[3,2-b]pyridin-5-yl)ethanamine (153 mg, 0.602 mmol) and tert-butyl 1,4-diazepane-1-carboxylate (241 mg, 1.20 mmol). After evacuating the flask and flushing it with nitrogen, the flask was charged with dioxane (1.6 mL) and potassium 2-methylpropan-2-olate (1.0 M in THF) (1.32 mL, 1.32 mmol). The mixture was then heated to 90° C. for 1 hour. After cooling, the mixture was worked up with saturated NaHCO$_3$ and EtOAc. The combined organic layers were dried over MgSO$_4$, filtered, and concentrated in vacuo. The crude product was purified by preparative HPLC (acid mode, 25-50% ACN/water gradient). The product-containing fractions were combined, neutralized with saturated NaHCO$_3$, concentrated in vacuo to remove ACN, and then extracted with EtOAc. The organic layers were combined, dried over MgSO$_4$, filtered, and concentrated in vacuo to give the title compound (76 mg, 34%). ESI-MS m/z [M+H]$^+$ calc'd for $C_{20}H_{31}N_5O_2$, 374. found 374.

Preparation 4: tert-Butyl (S)-4-(5-(1-((2-amino-5-cyano-6-methylpyrimidin-4-yl)amino)ethyl)-1-methyl-1H-pyrrolo[3,2-b]pyridin-6-yl)-1,4-diazepane-1-carboxylate

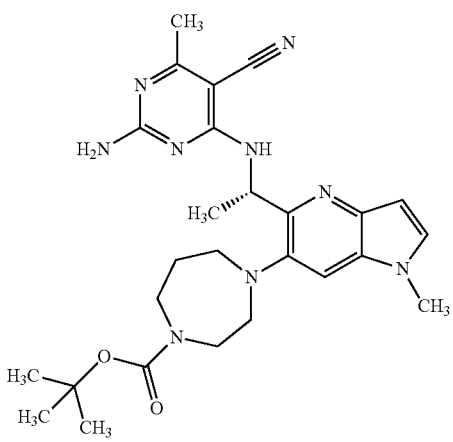 [SMILES: Cc1nc(N)nc(N[C@@H](C)c2nc3ccn(C)c3cc2N2CCCN(C(=O)OC(C)(C)C)CC2)c1C#N]

To a 25 mL pear flask were added 2-amino-4-chloro-6-methylpyrimidine-5-carbonitrile (70.7 mg, 0.419 mmol) and tert-butyl (S)-4-(5-(1-aminoethyl)-1-methyl-1H-pyrrolo[3,2-b]pyridin-6-yl)-1,4-diazepane-1-carboxylate (87 mg, 0.23 mmol) in DMSO (1.2 mL). Triethylamine (162 µL, 1.17 mmol) was added to the mixture which was then heated to 90° C. After 1 hour, UPLC indicated the reaction was complete. The reaction mixture was partitioned between saturated NaHCO$_3$ and ethyl acetate. The aqueous layer was extracted with ethyl acetate. The organic layers were combined, dried over MgSO$_4$, filtered, and concentrated. The residue was purified by liquid chromatography (SiO$_2$, 25-100% EtOAc/heptanes gradient) to give the title compound as a foam (81 mg, 69%). $^1$H NMR (400 MHz, DMSO-d$_6$) δ ppm 1.35-1.52 (m, 12H), 1.91 (s, 2H), 2.24 (s, 3H), 2.95-3.19 (m, 4H), 3.57 (d, J=5.56 Hz, 4H), 3.80 (br s, 1H), 5.90-6.01 (m, 1H), 6.49 (d, J=3.28 Hz, 1H), 6.95 (br s, 4H), 7.55 (d, J=3.03 Hz, 1H), 7.81 (d, J=6.82 Hz, 1H); ESI-MS m/z [M+H]$^+$ calc'd for C$_{26}$H$_{35}$N$_9$O$_2$, 506. found 506.

Preparation 5: tert-Butyl ((S)-1-(5-((S)-1-aminoethyl)-1-methyl-1H-pyrrolo[3,2-b]pyridin-6-yl)pyrrolidin-3-yl)(methyl)carbamate

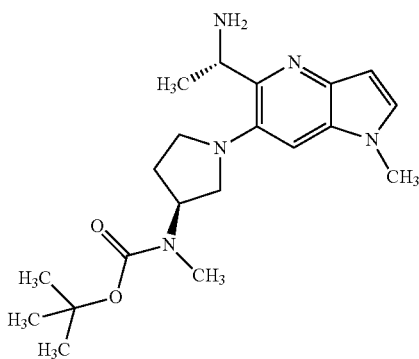 [SMILES: C[C@H](N)c1nc2ccn(C)c2cc1N1CC[C@H](N(C)C(=O)OC(C)(C)C)C1]

To a 50 mL pear flask were added (S)-tert-butyl methyl (pyrrolidin-3-yl)carbamate (235 mg, 1.173 mmol) and (S)-1-(6-bromo-1-methyl-1H-pyrrolo[3,2-b]pyridin-5-yl)ethanamine (166 mg, 0.652 mmol). After evacuating the flask and flushing it with nitrogen, the flask was charged with dioxane (1.7 mL) and potassium 2-methylpropan-2-olate (1.0 M in THF, 1.4 mL, 1.4 mmol). The mixture was then heated to 90° C. for 1 hour. After cooling, the mixture was worked up with saturated NaHCO$_3$ and EtOAc. The organic layers were combined, dried over MgSO$_4$, filtered, and concentrated in vacuo. The crude product was purified by preparative HPLC (acid mode, 25-50% ACN/water). The product-containing fractions were neutralized with a small amount of saturated NaHCO$_3$, concentrated in vacuo to remove ACN, and then extracted with EtOAc. The organic layers were combined, dried over MgSO$_4$, filtered, and concentrated in vacuo to give the title compound (120 mg, 49.0%). ESI-MS m/z [M+H]$^+$ calc'd for C$_{20}$H$_{31}$N$_5$O$_2$, 374. found 374.

Preparation 6: tert-Butyl ((S)-1-(5-((S)-1-((2-amino-5-cyano-6-methylpyrimidin-4-yl)amino)ethyl)-1-methyl-1H-pyrrolo[3,2-b]pyridin-6-yl)pyrrolidin-3-yl)(methyl)carbamate

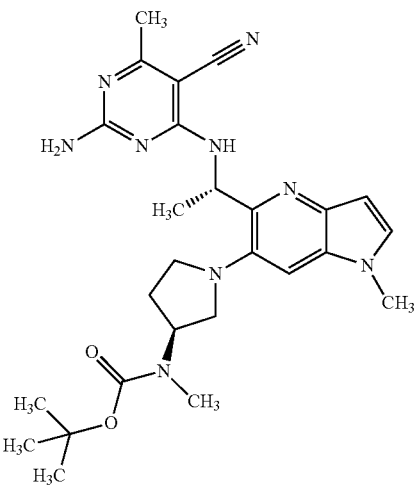 [SMILES: Cc1nc(N)nc(N[C@@H](C)c2nc3ccn(C)c3cc2N2CC[C@H](N(C)C(=O)OC(C)(C)C)C2)c1C#N]

To a 25 mL pear flask were added 2-amino-4-chloro-6-methylpyrimidine-5-carbonitrile (63.4 mg, 0.376 mmol) and tert-butyl ((S)-1-(5-((S)-1-aminoethyl)-1-methyl-1H-pyrrolo[3,2-b]pyridin-6-yl)pyrrolidin-3-yl)(methyl)carbamate (78 mg, 0.21 mmol) in DMSO (1.0 mL). Triethylamine (146 µL, 1.04 mmol) was added to the mixture, which was then heated to 90° C. for 2 hours. The reaction mixture was partitioned between saturated NaHCO$_3$ and ethyl acetate. The aqueous layer was extracted with ethyl acetate. The organic layers were combined, dried over MgSO$_4$, filtered, and concentrated. The residue was purified by liquid chromatography (SiO$_2$, 25-100% EtOAc/heptanes gradient) to give the title compound as a foam (72 mg, 68%). $^1$H NMR (400 MHz, DMSO-d$_6$) δ ppm 1.36-1.48 (m, 12H), 1.93-2.05 (m, 2H), 2.17-2.30 (m, 4H), 2.92 (s, 3H), 2.97-3.13 (m, 2H), 3.16-3.29 (m, 2H), 3.80 (s, 3H), 4.84 (br s, 1H), 5.71-5.89 (m, 1H), 6.39-6.55 (m, 1H), 6.84 (br s, 1H), 6.96 (d, J=7.58 Hz, 1H), 7.16 (br s, 1H), 7.55 (d, J=3.03 Hz, 1H), 7.85 (s, 1H); ESI-MS m/z [M+H]$^+$ calc'd for C$_{26}$H$_{35}$N$_9$O$_2$, 506. found 506.

Preparation 7: 2-((R)-1-(5-((S)-1-Aminoethyl)-1-methyl-1H-pyrrolo[3,2-b]pyridin-6-yl)piperidin-3-yl)isoindoline-1,3-dione

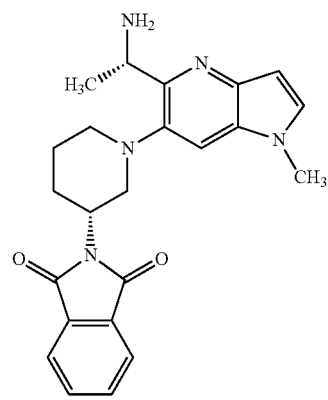 [SMILES: C[C@H](N)c1nc2ccn(C)c2cc1N1CCC[C@@H](N2C(=O)c3ccccc3C2=O)C1]

and

2-((S)-1-(5-((S)-1-Aminoethyl)-1-methyl-1H-pyrrolo[3,2-b]pyridin-6-yl)piperidin-3-yl)isoindoline-1,3-dione

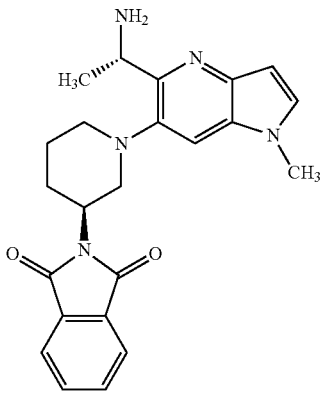 [SMILES: C[C@H](N)c1nc2ccn(C)c2cc1N1CCC[C@H](N2C(=O)c3ccccc3C2=O)C1]

Step A: 1-(5-((S)-1-Aminoethyl)-1-methyl-1H-pyrrolo[3,2-b]pyridin-6-yl)piperidin-3-ol

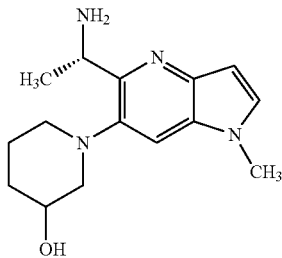 [SMILES: C[C@H](N)c1nc2ccn(C)c2cc1N1CCCC(O)C1]

A mixture of (S)-1-(6-bromo-1-methyl-1H-pyrrolo[3,2-b]pyridin-5-yl)ethan-1-amine (508 mg, 2.00 mmol), piperidin-3-ol (1.01 g, 10.0 mmol) and potassium 2-methylpropan-2-olate (1.56 g, 14.0 mmol) in dioxane (15 mL) was heated to 150° C. for 2 hours in a microwave reactor. The solvent was evaporated in vacuo to give the crude product (1.5 g) as a yellow oil which was used in the next step without further purification. ESI-MS m/z [M+H]$^+$ calc'd for $C_{15}H_{22}N_4O$, 275. found 275.

Step B: tert-Butyl ((1S)-1-(6-(3-hydroxypiperidin-1-yl)-1-methyl-1H-pyrrolo[3,2-b]pyridin-5-yl)ethyl)carbamate

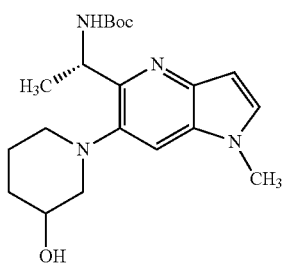 [SMILES: C[C@H](NC(=O)OC(C)(C)C)c1nc2ccn(C)c2cc1N1CCCC(O)C1]

A mixture of 1-(5-((S)-1-aminoethyl)-1-methyl-1H-pyrrolo[3,2-b]pyridin-6-yl)piperidin-3-ol (548 mg, 2.00 mmol) and Boc$_2$O (3.05 g, 14.0 mmol) in THF (20 mL) was stirred at 25° C. for 2 hours under a nitrogen atmosphere. The solvent was evaporated in vacuo, and the residue was purified by preparative HPLC to give the title compound as a yellow oil (300 mg, 38.6%). $^1$H NMR (400 MHz, CDCl$_3$) δ ppm 7.38 (d, J=15.6 Hz, 1H), 7.23 (s, 1H), 6.63 (s, 1H), 6.0-5.51 (m, 2H), 4.07-4.03 (m, 1H), 3.80 (s, 3H), 3.17-2.87 (m, 4H), 1.51-1.42 (m, 12H).

Step C: tert-Butyl ((1S)-1-(6-(3-(1,3-dioxoisoindolin-2-yl)piperidin-1-yl)-1-methyl-1H-pyrrolo[3,2-b]pyridin-5-yl)ethyl)carbamate

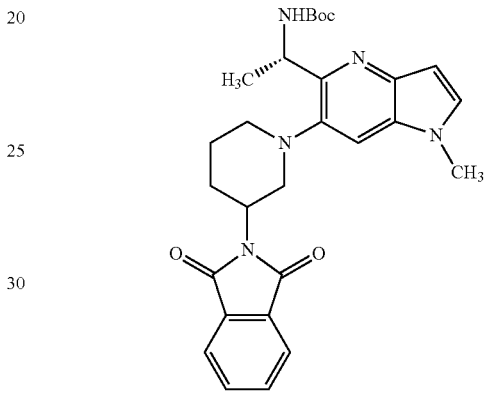

A mixture of tert-butyl ((1S)-1-(6-(3-hydroxypiperidin-1-yl)-1-methyl-1H-pyrrolo[3,2-b]pyridin-5-yl)ethyl)carbamate (300 mg, 0.802 mmol), isoindoline-1,3-dione (165 mg, 1.12 mmol) and PPh$_3$ (377 g, 1.44 mmol) in THF (2 mL) was stirred at 0° C. Next, diethyl azodicarboxylate (251 mg, 1.44 mmol) was added dropwise at 0° C., and the mixture was stirred at 20° C. for 16 hours. The solvent was evaporated in vacuo, and the residue was purified by preparative TLC to give the title compound as a white solid (100 mg, 35.2%). ESI-MS m/z [M+H]$^+$ calc'd for $C_{28}H_{33}N_5O_4$, 504. found 504.

Step D: 2-((R)-1-(5-((S)-1-aminoethyl)-1-methyl-1H-pyrrolo[3,2-b]pyridin-6-yl)piperidin-3-yl)isoindoline-1,3-dione, and 2-((S)-1-(5-((S)-1-aminoethyl)-1-methyl-1H-pyrrolo[3,2-b]pyridin-6-yl)piperidin-3-yl)isoindoline-1,3-dione A mixture of tert-butyl ((1S)-1-(6-(3-(1,3-dioxoisoindolin-2-yl)piperidin-1-yl)-1-methyl-1H-pyrrolo[3,2-b]pyridin-5-yl)ethyl)carbamate (100 mg, 0.59 mmol) in HCl/dioxane (10 mL) was stirred at 20° C. for 2 hours. The mixture was concentrated in vacuo and the residue was purified by preparative HPLC to give title diastereomers. Peak 2 (longer retention time, 20 mg, 18% yield): $^1$H NMR (400 MHz, CD$_3$OD) δ ppm 7.90-7.98 (m, 1H), 7.68-7.77 (m, 4H), 7.40 (d, J=3.0 Hz, 1H), 6.50 (d, J=3.1 Hz, 1H), 5.07 (q, J=6.6 Hz, 1H), 4.04-4.16 (m, 1H), 3.75 (s, 3H), 3.59-3.74 (m, 3H), 2.79-2.94 (m, 1H), 2.21-2.32 (m, 1H), 1.82-2.13 (m, 3H), 1.69 (d, J=6.8 Hz, 3H); ESI-MS m/z [M+H]+ calc'd for $C_{23}H_{25}N_5O_2$, 404. found 404. Peak 1 (shorter retention time, 30 mg, 27% yield): 1H NMR (400 MHz, $CD_3OD$) δ 7.85 (s, 1H), 7.64-7.57 (m, 4H), 7.32-7.26 (m, 1H), 6.35 (d, J=2.4 Hz, 1H), 5.29 (q, J=6.9 Hz, 1H), 4.20-4.08 (m, 1H), 3.85-3.70 (m, 2H), 3.67 (s, 3H), 3.45 (ddd, J=5.1, 7.4, 9.0 Hz, 1H), 2.95-2.86 (m, 1H), 2.34-2.22 (m, 1H), 2.12-2.00 (m, 2H), 1.82 (qd, J=8.5, 12.2 Hz, 1H), 1.65 (d, J=6.8 Hz, 3H); ESI-MS m/z [M+H]+ calc'd for $C_{23}H_{25}N_5O_2$, 404. found 404.

Preparation 8: 2-Amino-4-(((S)-1-(6-((R)-3-(1,3-dioxoisoindolin-2-yl)piperidin-1-yl)-1-methyl-1H-pyrrolo[3,2-b]pyridin-5-yl)ethyl)amino)-6-methylpyrimidine-5-carbonitrile

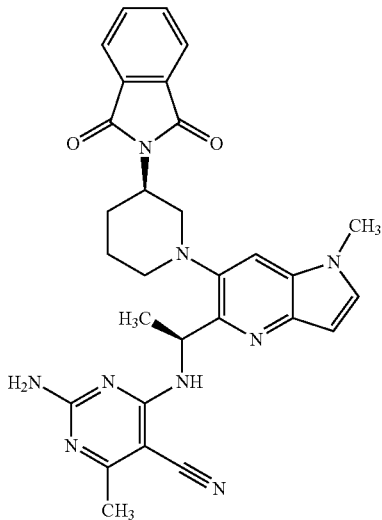 [SMILES: Cc1nc(N)nc(N[C@@H](C)c2nc3ccn(C)c3cc2N2CCC[C@@H](N3C(=O)c4ccccc4C3=O)C2)c1C#N]

A TFA salt of 2-((R)-1-(5-((S)-1-aminoethyl)-1-methyl-1H-pyrrolo[3,2-b]pyridin-6-yl)piperidin-3-yl)isoindoline-1,3-dione (Peak 2 of PREPARATION 7) was partitioned between saturated $NaHCO_3$ and ethyl acetate. The aqueous and organic phases were separated, and the organic layer was extracted with ethyl acetate. The organic layers were combined and concentrated to give the free base of 2-((R)-1-(5-((S)-1-aminoethyl)-1-methyl-1H-pyrrolo[3,2-b]pyridin-6-yl)piperidin-3-yl)isoindoline-1,3-dione. To a 25 mL pear flask were added the free base (15 mg, 0.037 mmol) and 2-amino-4-chloro-6-methylpyrimidine-5-carbonitrile (9.4 mg, 0.056 mmol) in DMSO (500 μL). Next, triethylamine (26 μL, 0.19 mmol) was added, and the mixture was heated to 85° C. for 2 hours. After cooling, the reaction mixture was partitioned between saturated $NaHCO_3$ and ethyl acetate. The aqueous and organic phases were separated, and the aqueous layer was extracted with ethyl acetate. The organic layers were combined, dried over $MgSO_4$, filtered, and concentrated to give the title compound, which was used without further purification. The absolute configuration of the stereocenter on the piperidine ring was not determined, but was assigned the opposite configuration of PREPARATION 9. ESI-MS m/z [M+H]+ calc'd for $C_{29}H_{29}N_9O_2$, 536. found 536.

Preparation 9: 2-Amino-4-(((S)-1-(6-((S)-3-(1,3-dioxoisoindolin-2-yl)piperidin-1-yl)-1-methyl-1H-pyrrolo[3,2-b]pyridin-5-yl)ethyl)amino)-6-methylpyrimidine-5-carbonitrile

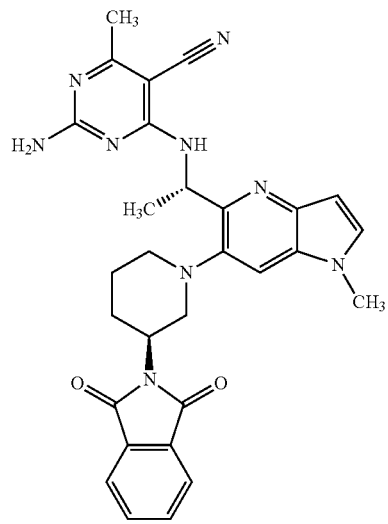 [SMILES: Cc1nc(N)nc(N[C@@H](C)c2nc3ccn(C)c3cc2N2CCC[C@H](N3C(=O)c4ccccc4C3=O)C2)c1C#N]

A TFA salt of 2-((S)-1-(5-((S)-1-aminoethyl)-1-methyl-1H-pyrrolo[3,2-b]pyridin-6-yl)piperidin-3-yl)isoindoline-1,3-dione (Peak 1 of PREPARATION 7) was partitioned between saturated $NaHCO_3$ and ethyl acetate. The aqueous and organic phases were separated, and the aqueous layer was extracted with ethyl acetate. The organic layers were combined and concentrated to give the free base of 2-((S)-1-(5-((S)-1-aminoethyl)-1-methyl-1H-pyrrolo[3,2-b]pyridin-6-yl)piperidin-3-yl)isoindoline-1,3-dione. To a 25 mL pear flask were added the free-base (16 mg, 0.040 mmol) and 2-amino-4-chloro-6-methylpyrimidine-5-carbonitrile (10 mg, 0.059 mmol) in DMSO (500 μL). Triethylamine (28 μl, 0.20 mmol) was added and the mixture was heated to 85° C. for 2 hours. After cooling, the reaction mixture was partitioned between saturated $NaHCO_3$ and ethyl acetate. The aqueous and organic phases were separated, and the aqueous layer was extracted with ethyl acetate. The organic layers were combined, dried over $MgSO_4$, filtered, and concentrated to give the title compound, which was used in without further purification. The absolute configuration of the stereocenter on the piperidine ring was not determined, but was assigned the opposite configuration of PREPARATION 8. ESI-MS m/z [M+H]+ calc'd for $C_{29}H_{29}N_9O_2$, 536. found 536.

Preparation 10: tert-Butyl (S)-4-(5-((S)-1-aminoethyl)-1-methyl-1H-pyrrolo[3,2-b]pyridin-6-yl)-2-methylpiperazine-1-carboxylate

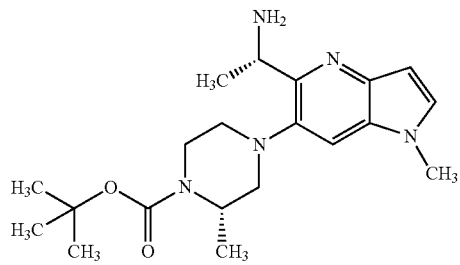 [SMILES: C[C@H](N)c1nc2ccn(C)c2cc1N1CCN(C(=O)OC(C)(C)C)[C@@H](C)C1]

To a 250 mL round-bottom flask were added (S)-tert-butyl 2-methylpiperazine-1-carboxylate (3.94 g, 19.7 mmol) and (S)-1-(6-bromo-1-methyl-1H-pyrrolo[3,2-b]pyridin-5-yl)ethanamine (2.5 g, 9.8 mmol) in 1,4-dioxane (23 mL). To the resulting solution was added potassium 2-methylpropan-2-olate (1 M in THF, 21 mL, 21 mmol), and the mixture was heated to 90° C. for 1 hour. After cooling for 10 minutes, the red mixture was poured into 300 mL of saturated NaHCO$_3$ and then extracted with EtOAc (3×). The organic layers were combined, dried over MgSO$_4$, filtered, and concentrated in vacuo to give crude product, which was purified by preparative HPLC (acid mode, 25-50% ACN/water gradient). The product-containing fractions were combined, concentrated in vacuo, and partitioned between saturated NaHCO$_3$ and EtOAc. The combined organic layers were dried over MgSO$_4$, filtered, and concentrated to give the title compound (1.41 g, 38.4%). ESI-MS m/z [M+H]$^+$ calc'd for $C_{20}H_{31}N_5O_2$, 374. found 374.

Preparation 11: tert-Butyl (S)-4-(5-((S)-1-((2-amino-5-cyano-6-methylpyrimidin-4-yl)amino)ethyl)-1-methyl-1H-pyrrolo[3,2-b]pyridin-6-yl)-2-methylpiperazine-1-carboxylate

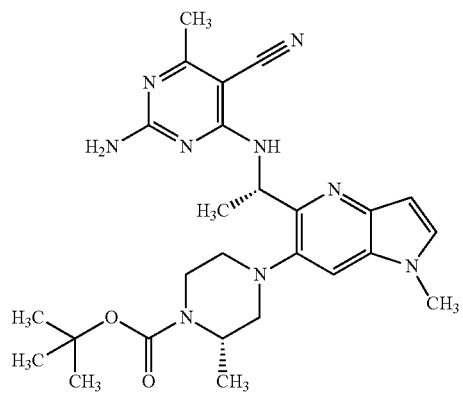 [SMILES: Cc1nc(N)nc(N[C@@H](C)c2nc3ccn(C)c3cc2N2CCN(C(=O)OC(C)(C)C)[C@@H](C)C2)c1C#N]

To a 250 mL round-bottom flask were added 2-amino-4-chloro-6-methylpyrimidine-5-carbonitrile (0.821 g, 4.87 mmol) and tert-butyl (S)-4-(5-((S)-1-aminoethyl)-1-methyl-1H-pyrrolo[3,2-b]pyridin-6-yl)-2-methylpiperazine-1-carboxylate (1.40 g, 3.75 mmol) in DMSO (15 mL). Triethylamine (2.1 mL, 15 mmol) was added to the mixture, which was then heated to 85° C. for 2 hours. After cooling, the mixture was partitioned between saturated NaHCO$_3$ and ethyl acetate. The aqueous layer was extracted with ethyl acetate. The organic layers were combined, dried over MgSO$_4$, filtered, and concentrated. The crude product was purified by column chromatography (SiO$_2$, 20-100% EtOAc/heptane gradient). The product-containing fractions were combined and then concentrated in vacuo to give the title compound as light-yellow oil (1.7 g, 90%). ESI-MS m/z [M+H]$^+$ calc'd for $C_{26}H_{35}N_9O_2$, 506. found 506.

Preparation 12: 2-(1-(5-((S)-1-Aminoethyl)-1-methyl-1H-pyrrolo[3,2-b]pyridin-6-yl)pyrrolidin-3-yl)isoindoline-1,3-dione

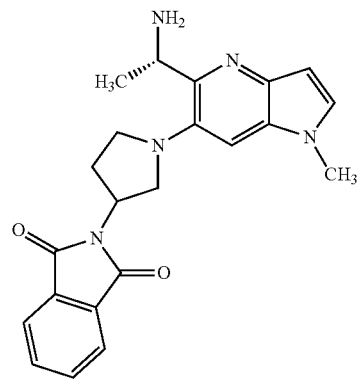 [SMILES: C[C@H](N)c1nc2ccn(C)c2cc1N1CCC(N2C(=O)c3ccccc3C2=O)C1]

Step A: 1-(5-((S)-1-Aminoethyl)-1-methyl-1H-pyrrolo[3,2-b]pyridin-6-yl)pyrrolidin-3-ol

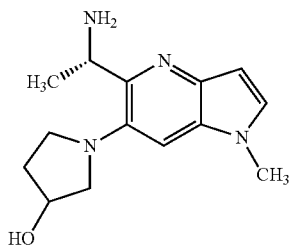

A mixture of (S)-1-(6-bromo-1-methyl-1H-pyrrolo[3,2-b]pyridin-5-yl)ethan-1-amine (510 mg, 2.0 mmol), pyrrolidin-3-ol (870 mg, 10 mmol) and potassium 2-methylpropan-2-olate (1.56 g, 14.0 mmol) in dioxane (15 mL) was heated to 150° C. for 2 hours in a microwave reactor. The solvent was evaporated in vacuo to give the title compound as a yellow oil which was used without further purification (1.5 g). ESI-MS m/z [M+H]$^+$ calc'd for $C_{14}H_{20}N_4O$, 261. found 261.

Step B: tert-Butyl ((1S)-1-(6-(3-hydroxypyrrolidin-1-yl)-1-methyl-1H-pyrrolo[3,2-b]pyridin-5-yl)ethyl)carbamate

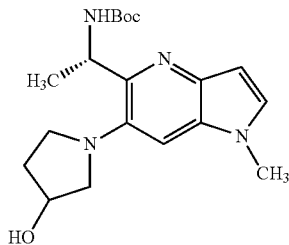

A mixture of 1-(5-((S)-1-aminoethyl)-1-methyl-1H-pyrrolo[3,2-b]pyridin-6-yl)pyrrolidin-3-ol (520 mg, 2.0 mmol) and Boc$_2$O (3.05 g, 14.0 mmol) in THF (20 mL) was stirred at 25° C. for 2 hours under a nitrogen atmosphere. The solvent was evaporated in vacuo, and the residue was purified by preparative HPLC to give the title compound as a yellow oil (200 mg, 27.8%). $^1$H NMR (400 MHz, CDCl$_3$) δ ppm 7.43 (d, J=6.4 Hz, 1H), 7.21 (s, 1H), 6.63 (s, 1H), 5.95-5.74 (m, 1H), 5.63-5.46 (m, 1H), 4.52 (s, 1H), 3.78 (s, 3H), 3.51-3.09 (m, 6H), 2.37-2.33 (m, 1H), 2.05-1.95 (m, 1H), 1.55-1.43 (m, 12H).

Step C: tert-Butyl ((1S)-1-(6-(3-(1,3-dioxoisoindolin-2-yl)pyrrolidin-1-yl)-1-methyl-1H-pyrrolo[3,2-b]pyridin-5-yl)ethyl)carbamate

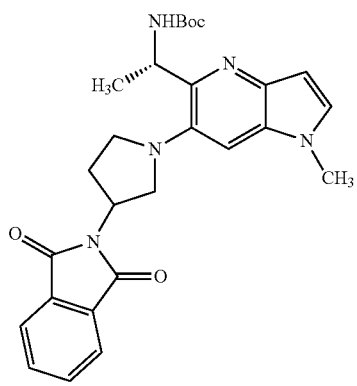 [SMILES: C[C@H](NC(=O)OC(C)(C)C)c1nc2ccn(C)c2cc1N1CCC(N2C(=O)c3ccccc3C2=O)C1]

A mixture of tert-butyl ((1S)-1-(6-(3-hydroxypyrrolidin-1-yl)-1-methyl-1H-pyrrolo[3,2-b]pyridin-5-yl)ethyl)carbamate (250 mg, 0.694 mmol), isoindoline-1,3-dione (153 mg, 1.04 mmol) and PPh$_3$ (328 g, 1.25 mmol) in THF (2 mL) was stirred at 0° C. Next, diethyl azodicarboxylate (217 mg, 1.25 mmol) was added dropwise at 0° C. and the mixture was stirred at 20° C. for 16 hours. The solvent was evaporated in vacuo, and the residue was purified by preparative TLC to give the title compound as a white solid (200 mg, 42.3%). ESI-MS m/z [M+H]$^+$ calc'd for C$_{22}$H$_{31}$N$_5$O$_4$, 490. found 490.

Step D: 2-(1-(5-((S)-1-aminoethyl)-1-methyl-1H-pyrrolo[3,2-b]pyridin-6-yl)pyrrolidin-3-yl)isoindoline-1,3-dione A mixture of tert-butyl ((1S)-1-(6-(3-(1,3-dioxoisoindolin-2-yl)pyrrolidin-1-yl)-1-methyl-1H-pyrrolo[3,2-b]pyridin-5-yl)ethyl)carbamate (200 mg, 0.409 mmol) in HCl/dioxane (10 mL) was stirred at 20° C. for 2 hours. The solvent was concentrated in vacuo. The residue was purified by preparative HPLC to give a TFA salt of the title compound as a yellow solid (190 mg, 94.2%). $^1$H NMR (400 MHz, CD$_3$OD) δ ppm 8.19 (d, J=3.2 Hz, 1H), 7.92-7.90 (m, 2H), 7.86-7.84 (m, 2H), 7.62 (d, J=3.2 Hz, 1H), 6.65 (d, J=3.2 Hz, 1H), 5.21-5.13 (m, 2H), 3.91 (s, 3H), 3.59-3.54 (m, 2H), 3.47 (q, J=4.8 Hz, 1H), 3.34 (m, 1H), 2.54-2.47 (m, 2H), 1.74 (dd, J=6.8 Hz, 1.6 Hz, 3H); ESI-MS m/z [M+H]$^+$ calc'd for C$_{22}$H$_{23}$N$_5$O$_2$, 390. found 390.

Preparation 13: 2-Amino-4-(((S)-1-(6-((R)-3-(1,3-dioxoisoindolin-2-yl)pyrrolidin-1-yl)-1-methyl-1H-pyrrolo[3,2-b]pyridin-5-yl)ethyl)amino)-6-methylpyrimidine-5-carbonitrile

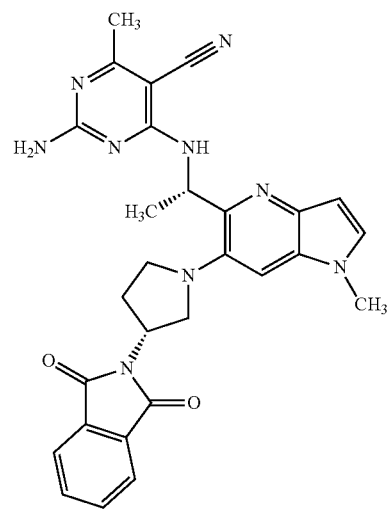 [SMILES: Cc1nc(N)nc(N[C@@H](C)c2nc3ccn(C)c3cc2N2CC[C@@H](N3C(=O)c4ccccc4C3=O)C2)c1C#N]

and

2-Amino-4-(((S)-1-(6-((S)-3-(1,3-dioxoisoindolin-2-yl)pyrrolidin-1-yl)-1-methyl-1H-pyrrolo[3,2-b]pyridin-5-yl)ethyl)amino)-6-methylpyrimidine-5-carbonitrile

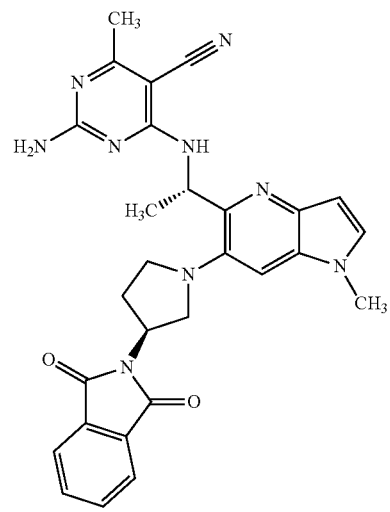 [SMILES: Cc1nc(N)nc(N[C@@H](C)c2nc3ccn(C)c3cc2N2CC[C@H](N3C(=O)c4ccccc4C3=O)C2)c1C#N]

A TFA salt of 2-(1-(5-((S)-1-aminoethyl)-1-methyl-1H-pyrrolo[3,2-b]pyridin-6-yl)pyrrolidin-3-yl)isoindoline-1,3-dione (110 mg, 0.218 mmol) was partitioned between saturated NaHCO$_3$ and EtOAc. The aqueous and organic phases were separated and the aqueous layer was extracted with EtOAc (2×). The organic layers were combined, dried over MgSO₄, and filtered, and then concentrated in a 50 mL pear flask. To this residue was added 2-amino-4-chloro-6-methylpyrimidine-5-carbonitrile (55.2 mg, 0.328 mmol) in DMSO (1.1 mL) followed by triethylamine (152 μL, 1.09 mmol). The mixture was heated to 85° C. for 3 hours and then partitioned between saturated NaHCO₃ and ethyl acetate. The aqueous layer was extracted with ethyl acetate. The organic layers were combined, dried over MgSO₄, filtered, and concentrated. The crude product was purified by preparative HPLC (acid mode, 50-55% ACN/water gradient) to give the title diastereomers. Peak 1 (shorter retention time, 30 mg, 26%): ¹H NMR (400 MHz, CDCl₃) δ ppm 1.52 (d, J=6.57 Hz, 3H), 2.33-2.40 (m, 3H), 2.40-2.60 (m, 2H), 3.31-3.48 (m, 3H), 3.70 (t, J=8.34 Hz, 1H), 3.76-3.83 (m, 3H), 5.09-5.22 (m, 1H), 5.28 (s, 2H), 5.87-5.96 (m, 1H), 6.66 (dd, J=3.28, 0.76 Hz, 1H), 7.20-7.25 (m, 2H), 7.57 (s, 1H), 7.71-7.79 (m, 2H), 7.84-7.92 (m, 2H); ESI-MS m/z [M+H]⁺ calc'd for C₂₈H₂₇N₉O₂, 522. found 522. Peak 2 (longer retention time, 12 mg, 11%): ESI-MS m/z [M+H]⁺ calc'd for C₂₈H₂₇N₉O₂, 522. found 522.

Preparation 14: tert-Butyl (R)-4-(5-((S)-1-aminoethyl)-1-methyl-1H-pyrrolo[3,2-b]pyridin-6-yl)-2-methylpiperazine-1-carboxylate

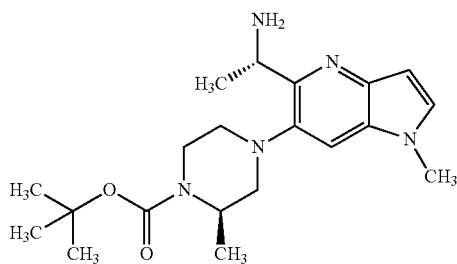 [SMILES: C[C@H](N)c1nc2ccn(C)c2cc1N1CCN(C(=O)OC(C)(C)C)[C@H](C)C1]

To a 50 mL pear flask were added (R)-tert-butyl 2-methylpiperazine-1-carboxylate (156 mg, 0.777 mmol) and (S)-1-(6-bromo-1-methyl-1H-pyrrolo[3,2-b]pyridin-5-yl)ethanamine (94 mg, 0.370 mmol) in 1,4-dioxane (0.92 mL). Potassium 2-methylpropan-2-olate (1 M in THF, 0.81 mL, 0.81 mmol) was added, and the mixture was heated to 90° C. for 45 minutes. After cooling for 10 minutes, the red mixture was poured into saturated NaHCO₃ and the pH was adjusted to ~10 by adding K₂CO₃. The mixture was extracted with EtOAc (3×). The organic layers were combined, dried over MgSO₄, filtered, and concentrated in vacuo to give crude product, which was purified by preparative HPLC (basic mode, 30-55% ACN/water gradient). The product-containing fractions were combined, concentrated in vacuo, and then partitioned between saturated NaHCO₃ and EtOAc. The organic phase was dried over MgSO₄, filtered, and concentrated to give the title compound as a colorless oil (45 mg, 33%). ESI-MS m/z [M+H]⁺ calc'd for C₂₀H₃₁N₅O₂, 374. found 374.

Preparation 15: tert-Butyl (R)-4-(5-((S)-1-((2-amino-5-cyano-6-methylpyrimidin-4-yl)amino)ethyl)-1-methyl-1H-pyrrolo[3,2-b]pyridin-6-yl)-2-methylpiperazine-1-carboxylate

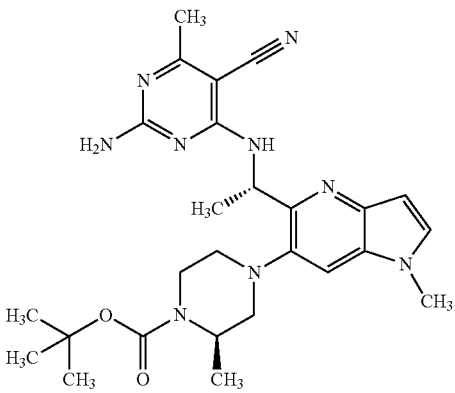 [SMILES: Cc1nc(N)nc(N[C@@H](C)c2nc3ccn(C)c3cc2N2CCN(C(=O)OC(C)(C)C)[C@H](C)C2)c1C#N]

To a 50 mL pear flask were added 2-amino-4-chloro-6-methylpyrimidine-5-carbonitrile (30.5 mg, 0.181 mmol) and tert-butyl (R)-4-(5-((S)-1-aminoethyl)-1-methyl-1H-pyrrolo[3,2-b]pyridin-6-yl)-2-methylpiperazine-1-carboxylate (45 mg, 0.120 mmol) in DMSO (0.60 mL). Triethylamine (84 μL, 0.60 mmol) was added, and the mixture was stirred at 80° C. for 2 hours. Additional triethylamine (84 μL, 0.602 mmol) and 2-amino-4-chloro-6-methylpyrimidine-5-carbonitrile (10 mg, 0.060 mmol) were added and the mixture was heated for another 3 hours at 80° C. The cooled mixture was partitioned between saturated NaHCO₃ and ethyl acetate. The aqueous layer was extracted with ethyl acetate. The organic layers were combined, dried over MgSO₄, filtered, and concentrated. The residue was purified by liquid chromatography (SiO₂, 25-100% EtOAc/heptanes gradient) to give the title compound as a white solid (51 mg, 84%). ¹H NMR (400 MHz, CDCl₃) δ ppm 1.48-1.52 (m, 12H), 1.54 (d, J=6.82 Hz, 3H), 2.39 (s, 3H), 2.79-2.86 (m, 1H), 2.89-3.09 (m, 3H), 3.35 (br s, 1H), 3.78 (s, 3H), 4.05 (d, J=9.85 Hz, 1H), 4.34 (br s, 1H), 5.27 (br s, 1H), 5.94 (quin, J=6.76 Hz, 1H), 6.66 (d, J=3.28 Hz, 1H), 7.24 (d, J=3.28 Hz, 1H), 7.31 (d, J=7.83 Hz, 1H), 7.40 (s, 1H); ESI-MS m/z [M+H]⁺ calc'd for C₂₆H₃₅N₉O₂, 506. found 506.

Preparation 16: Benzyl (S)-(1-(6-bromo-1-methyl-1H-pyrrolo[3,2-b]pyridin-5-yl)ethyl)carbamate

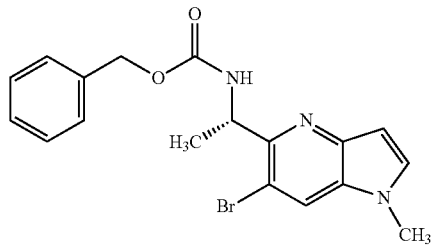 [SMILES: C[C@H](NC(=O)OCc1ccccc1)c1nc2ccn(C)c2cc1Br]

To a stirred solution of (S)-1-(6-bromo-1-methyl-1H-pyrrolo[3,2-b]pyridin-5-yl)ethan-1-amine (1.0 g, 3.93 mmol) in DCM (20 mL) was added triethylamine (796 mg, 7.87 mmol) followed by CbzCl (808 mg, 4.72 mmol) at 0° C. The reaction mixture was stirred at about 0 to 26° C. for 1.5 hours. After the solvent was removed, the residue was purified by silica gel column chromatography (PE/EtOAc=10:1) to give the title compound as a yellow oil (1.44 g, 94.7%).

Preparation 17: tert-Butyl 3-(5-((S)-1-aminoethyl)-1-methyl-1H-pyrrolo[3,2-b]pyridin-6-yl)pyrrolidine-1-carboxylate

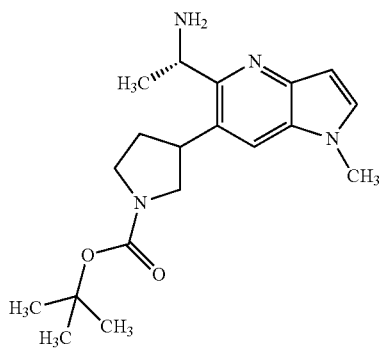 [SMILES: C[C@H](N)c1nc2ccn(C)c2cc1C1CCN(C(=O)OC(C)(C)C)C1]

Step A: tert-Butyl (S)-3-(5-(1-(((benzyloxy)carbonyl)amino)ethyl)-1-methyl-1H-pyrrolo[3,2-b]pyridin-6-yl)-2,5-dihydro-1H-pyrrole-1-carboxylate

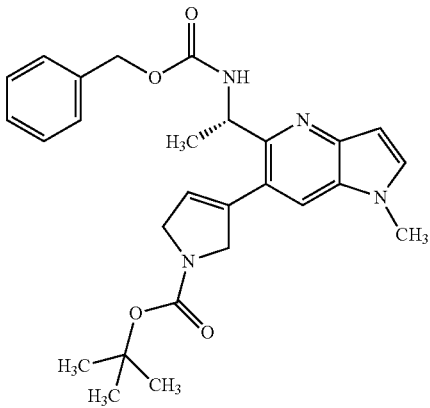 [SMILES: C[C@H](NC(=O)OCc1ccccc1)c1nc2ccn(C)c2cc1C1=CCN(C(=O)OC(C)(C)C)C1]

A mixture of benzyl (S)-(1-(6-bromo-1-methyl-1H-pyrrolo[3,2-b]pyridin-5-yl)ethyl)carbamate (850 mg, 2.19 mmol), tert-butyl 3-(4,4,5,5-tetramethyl-1,3,2-dioxaborolan-2-yl)-2,5-dihydro-1H-pyrrole-1-carboxylate (904 mg, 3.06 mmol), K$_2$CO$_3$ (605 mg, 4.38 mmol) and Pd(dppf)Cl$_2$ (170 mg, 0.22 mmol) in anhydrous DMF (25 mL) was stirred at 100° C. for 5 hours under nitrogen. After the solvent was removed, the residue was purified by silica gel column chromatography (PE/EtOAc=7:1) to give the title compound as a yellow oil (900 mg, 87%). ESI-MS m/z [M+H]$^+$ calc'd for C$_{22}$H$_{32}$N$_4$O$_4$, 477. found 477.

Step B: tert-Butyl 3-(5-((S)-1-aminoethyl)-1-methyl-1H-pyrrolo[3,2-b]pyridin-6-yl)pyrrolidine-1-carboxylate A mixture of tert-butyl (S)-3-(5-(1-(((benzyloxy)carbonyl)amino)ethyl)-1-methyl-1H-pyrrolo[3,2-b]pyridin-6-yl)-2,5-dihydro-1H-pyrrole-1-carboxylate (900 mg, 1.89 mmol) and Pd/C (100 mg) in EtOH (50 mL) was stirred at 27° C. for 3 hours under H$_2$ (50 psi). The reaction mixture was subsequently filtered, and the filtrate was concentrated to dryness. The residue was purified by preparative HPLC to afford a mixture of the diastereomers of the title compound as a yellow oil (350 mg, 54%). $^1$H NMR (400 MHz, CDCl$_3$) δ ppm 7.44 (d, J=6.4 Hz, 1H), 7.22 (d, J=3.2 Hz, 1H), 6.61 (d, J=3.2 Hz, 1H), 4.51 (q, J=6.4 Hz, 1H), 3.86-3.37 (m, 1H), 3.76 (s, 3H), 2.31-2.30 (m, 1H), 1.50 (s, 9H), 1.44 (d, J=6.4 Hz, 3H); ESI-MS m/z [M+H]$^+$ calc'd for C$_{19}$H$_{28}$N$_4$O$_2$, 345. found 345.

Preparation 18: tert-Butyl (R)-3-(5-((S)-1-((2-amino-5-cyano-6-methylpyrimidin-4-yl)amino)ethyl)-1-methyl-1H-pyrrolo[3,2-b]pyridin-6-yl)pyrrolidine-1-carboxylate

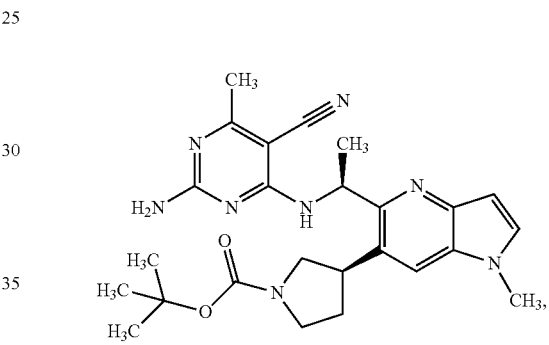

and tert-Butyl (S)-3-(5-((S)-1-((2-amino-5-cyano-6-methylpyrimidin-4-yl)amino)ethyl)-1-methyl-1H-pyrrolo[3,2-b]pyridin-6-yl)pyrrolidine-1-carboxylate

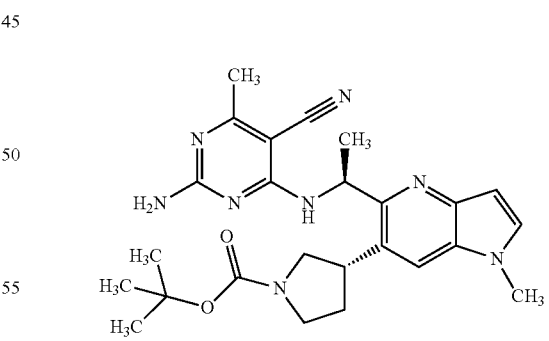

To a 25 mL pear flask were added the mixture of diastereomers of tert-butyl 3-(5-((S)-1-aminoethyl)-1-methyl-1H-pyrrolo[3,2-b]pyridin-6-yl)pyrrolidine-1-carboxylate (0.057 g, 0.17 mmol) and 2-amino-4-chloro-6-methylpyrimidine-5-carbonitrile (0.042 g, 0.25 mmol) in DMSO (1 mL). Triethylamine (0.069 mL, 0.50 mmol) was added and the mixture was heated to 85° C. for 14 hours. The reaction mixture was partitioned between saturated NaHCO$_3$ and ethyl acetate. The aqueous layer was extracted with ethyl acetate. The organic layers were combined, dried over MgSO₄, filtered, and concentrated. The crude product was purified by liquid chromatography (SiO₂, 25-100% EtOAc/hexanes). The product-containing fractions from two different peaks were pooled separately and concentrated in vacuo to give the title diastereomers. Peak 1 (shorter retention time, 19 mg, 24%): $^1$H NMR (400 MHz, CDCl₃) δ ppm 0.69-0.85 (m, 5H), 1.32-1.51 (m, 22H), 2.15-2.40 (m, 8H), 3.33-3.49 (m, 2H), 3.52-3.86 (m, 8H), 4.70 (dd, J=10.74, 7.45 Hz, 1H), 5.27 (br s, 1H), 5.62-5.75 (m, 1H), 5.82-5.96 (m, 2H), 6.60 (br s, 2H), 6.73 (d, J=8.84 Hz, 1H), 7.19 (s, 2H), 7.33-7.45 (m, 1H); ESI-MS m/z [M+H]⁺ calc'd for C₂₅H₃₂N₈O₂, 477. found 477. Peak 2 (longer retention time, 41 mg, 52%): $^1$H NMR (400 MHz, CDCl₃) δ ppm 0.66-0.90 (m, 3H), 1.39-1.52 (m, 15H), 1.88-2.07 (m, 3H), 2.21-2.40 (m, 5H), 3.30-3.89 (m, 10H), 5.02-5.20 (m, 2H), 5.65 (t, J=6.44 Hz, 1H), 6.61 (d, J=3.03 Hz, 1H), 7.14-7.24 (m, 2H), 7.28-7.46 (m, 2H); ESI-MS m/z [M+H]⁺ calc'd for C₂₅H₃₂N₈O₂, 477. found 477.

Preparation 19: tert-Butyl (S)-4-(5-(1-aminoethyl)-1-methyl-1H-pyrrolo[3,2-b]pyridin-6-yl)piperidine-1-carboxylate

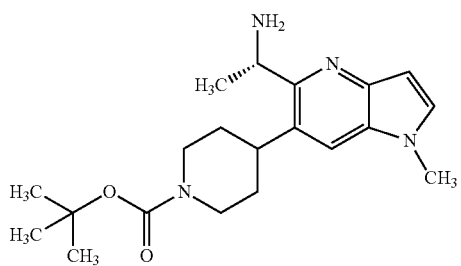

Step A: tert-Butyl (S)-4-(5-(1-(((benzyloxy)carbonyl)amino)ethyl)-1-methyl-1H-pyrrolo[3,2-b]pyridin-6-yl)-3,6-dihydropyridine-1(2H)-carboxylate

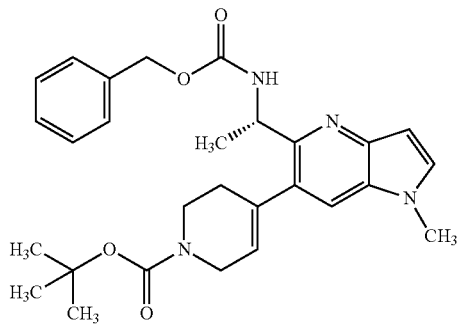 [SMILES: C[C@H](NC(=O)OCc1ccccc1)c1nc2ccn(C)c2cc1C1=CCN(C(=O)OC(C)(C)C)CC1]

The title compound was prepared similar to STEP A in PREPARATION 17 using tert-butyl 4-(4,4,5,5-tetramethyl-1,3,2-dioxaborolan-2-yl)-3,6-dihydropyridine-1(2H)-carboxylate and benzyl (S)-(1-(6-bromo-1-methyl-1H-pyrrolo[3,2-b]pyridin-5-yl)ethyl)carbamate as starting materials.

Step B: tert-Butyl (S)-4-(5-(1-aminoethyl)-1-methyl-1H-pyrrolo[3,2-b]pyridin-6-yl)piperidine-1-carboxylate A formate salt of the title compound was prepared similar to STEP B in PREPARATION 17. $^1$H NMR (400 MHz, CDCl₃) δ ppm 8.24 (br, 1H), 7.49 (s, 1H), 7.28 (d, J=3.2 Hz, 1H), 6.59 (d, J=2.8 Hz, 1H), 5.01 (d, J=6.4 Hz, 1H), 4.31-4.26 (m, 3H), 3.80 (s, 3H), 2.88 (br, 3H), 1.89-1.76 (m, 3H), 1.60 (d, J=6.4 Hz, 3H), 1.49 (s, 9H); ESI-MS m/z [M+H]⁺ calc'd for C₂₀H₃₀N₄O₂, 359. found 359.

Preparation 20: tert-Butyl (S)-4-(5-(1-(2-amino-5-cyano-6-methylpyrimidin-4-yl)amino)ethyl)-1-methyl-1H-pyrrolo[3,2-b]pyridin-6-yl)piperidine-1-carboxylate

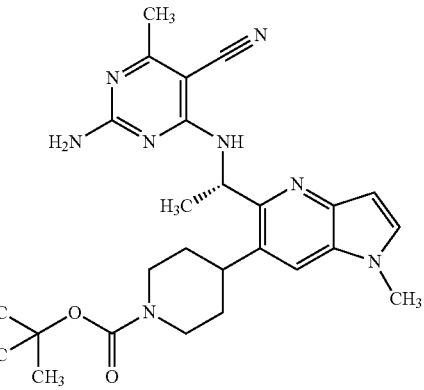

To a 25 mL pear flask were added 2-amino-4-chloro-6-methylpyrimidine-5-carbonitrile (0.044 g, 0.26 mmol) and the formate salt of tert-butyl (S)-4-(5-(1-aminoethyl)-1-methyl-1H-pyrrolo[3,2-b]pyridin-6-yl)piperidine-1-carboxylate (0.071 g, 0.176 mmol) in DMSO (1.5 mL). Triethylamine (0.12 mL, 0.88 mmol) was added and the mixture was stirred at 85° C. for 2 hours. The mixture was subsequently cooled and partitioned between saturated NaHCO₃ and ethyl acetate. The aqueous layer was extracted with ethyl acetate. The organic layers were combined, dried over MgSO₄, filtered, and concentrated. The residue was purified by liquid chromatography (SiO₂, 25-100% EtOAc/heptanes gradient) to give the title compound as a white solid (28 mg, 33%). ESI-MS m/z [M+H]⁺ calc'd for C₂₆H₃₄N₈O₂, 491. found 491.

Preparation 21: tert-Butyl (S)-4-(5-(1-((2,6-diamino-5-cyanopyrimidin-4-yl)amino)ethyl)-1-methyl-1H-pyrrolo[3,2-b]pyridin-6-yl)piperazine-1-carboxylate

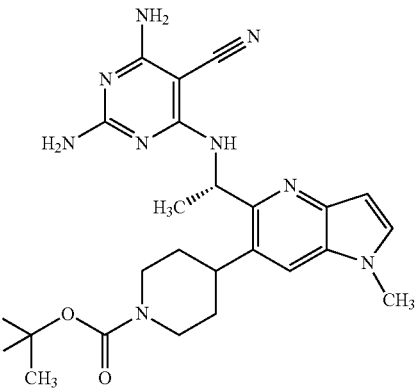

To a 25 mL pear flask were added tert-butyl (S)-4-(5-(1-aminoethyl)-1-methyl-1H-pyrrolo[3,2-b]pyridin-6-yl)piperazine-1-carboxylate (0.076 g, 0.21 mmol) and 2,4-diamino-6-chloropyrimidine-5-carbonitrile (0.054 g, 0.32 mmol) in DMSO (1 mL) to give a yellow suspension. Triethylamine (0.088 mL, 0.63 mmol) was added and the mixture was heated to 95° C. for 2 hours. The reaction appeared to stall so 1 equivalent of triethylamine was added. After a total of 4 hours of heating, the mixture was cooled and the reaction mixture was partitioned between saturated NaHCO₃ and ethyl acetate. The aqueous layer was extracted with ethyl acetate. The organic layers were combined, dried over MgSO₄, filtered, and concentrated. The crude product was purified by preparative HPLC (acid mode, 20-25% ACN/water gradient). The product-containing fractions were combined, neutralized with a small amount of saturated NaHCO3, concentrated in vacuo to remove ACN, and then extracted with EtOAc. The organic layers were combined, dried over MgSO₄, filtered, and concentrated in vacuo to give the title compound as a pale beige solid (37 mg, 36%). ¹H NMR (400 MHz, CDCl₃) δ ppm 1.43 (s, 11H), 1.87 (br s, 2H), 2.72 (br s, 2H), 2.97 (br s, 2H), 3.70 (s, 3H), 4.80-5.11 (m, 4H), 5.92 (br s, 1H), 6.59 (d, J=2.27 Hz, 1H), 6.76 (d, J=6.06 Hz, 1H), 7.16 (d, J=2.78 Hz, 2H), 7.32 (s, 1H); ESI-MS m/z [M+H]⁺ calc'd for $C_{24}H_{32}N_{10}O_2$, 493. found 493.

Preparation 22: tert-Butyl (1S,4S)-5-(5-((S)-1-aminoethyl)-1-methyl-1H-pyrrolo[3,2-b]pyridin-6-yl)-2,5-diazabicyclo[2.2.1]heptane-2-carboxylate

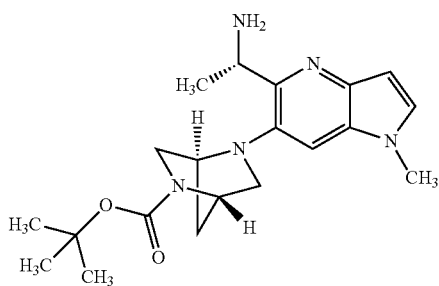 [SMILES: C[C@H](N)c1nc2ccn(C)c2cc1N1C[C@@H]2C[C@H]1CN2C(=O)OC(C)(C)C]

To a 50 mL pear flask were added (S)-1-(6-bromo-1-methyl-1H-pyrrolo[3,2-b]pyridin-5-yl)ethanamine (628 mg, 2.471 mmol) and (1S,4S)-tert-butyl 2,5-diazabicyclo[2.2.1]heptane-2-carboxylate (906 mg, 4.57 mmol). After evacuating the flask and flushing it with nitrogen, 1,4-dioxane (5.9 mL) and potassium 2-methylpropan-2-olate (1 M in THF, 5.4 mL, 5.4 mmol) were added. The mixture was heated to 90° C. for 1 hour. The reaction mixture was then cooled and worked up with saturated NaHCO₃ and EtOAc. The combined organic layers were dried over MgSO₄, filtered, and concentrated in vacuo. The crude product was purified by preparative HPLC (acid mode, 25-65% ACN/water gradient). The product-containing fractions were combined, neutralized with a small amount of saturated NaHCO₃, concentrated in vacuo to remove ACN, and then extracted with EtOAc. The organic layers were combined, dried over MgSO₄, filtered, and concentrated in vacuo to give the title compound (305 mg, 33.2%). ESI-MS m/z [M+H]⁺ calc'd for $C_{20}H_{29}N_5O_2$, 372. found 372.

Preparation 23: tert-Butyl (1S,4S)-5-(5-((S)-1-(2-amino-5-cyano-6-methylpyrimidin-4-yl)amino) ethyl)-1-methyl-1H-pyrrolo[3,2-b]pyridin-6-yl)-2,5-diazabicyclo[2.2.1]heptane-2-carboxylate

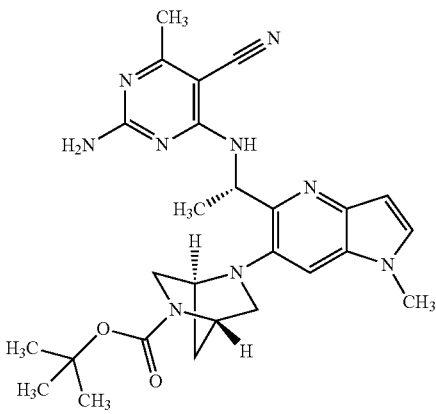 [SMILES: Cc1nc(N)nc(N[C@@H](C)c2nc3ccn(C)c3cc2N2C[C@@H]3C[C@H]2CN3C(=O)OC(C)(C)C)c1C#N]

To a 50 mL pear flask were added 2-amino-4-chloro-6-methylpyrimidine-5-carbonitrile (102 mg, 0.603 mmol) and tert-butyl (1S,4S)-5-(5-((S)-1-aminoethyl)-1-methyl-1H-pyrrolo[3,2-b]pyridin-6-yl)-2,5-diazabicyclo[2.2.1]heptane-2-carboxylate (160 mg, 0.431 mmol) in DMSO (2.2 mL). Triethylamine (180 µL, 1.29 mmol) was added and the mixture was heated to 90° C. After 3.5 hours UPLC indicated the reaction was complete. The reaction mixture was partitioned between saturated NaHCO₃ and ethyl acetate. The aqueous layer was extracted with ethyl acetate. The organic layers were combined, dried over MgSO₄, filtered, and concentrated. The residue was purified by liquid chromatography (SiO₂, 25-100% EtOAc/heptanes gradient) to give the title compound as a colorless oil (215 mg, 99%). ESI-MS m/z [M+H]⁺ calc'd for $C_{26}H_{33}N_9O_2$, 504. found 504.

Preparation 24: 1-(6-Bromo-1-methyl-1H-pyrrolo[3,2-b]pyridin-5-yl)propan-1-amine

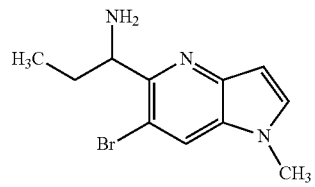

Ethylmagnesium bromide (4.18 mL, 12.54 mmol) was added to a stirred solution of 6-bromo-1-methyl-1H-pyrrolo[3,2-b]pyridine-5-carbonitrile (740 mg, 3.13 mmol) in THF (16 mL) at room temperature. The mixture was stirred for one hour at room temperature and then quenched with methanol (5 mL). Sodium borohydride (237 mg, 6.27 mmol) was added. The reaction mixture was stirred for one hour, quenched with 1N HCl (1.5 mL) and stirred for 20 minutes. Next, the mixture was basified with saturated aqueous sodium bicarbonate and extracted with ethyl acetate (2×). The organic layer was dried over anhydrous magnesium sulfate and concentrated to give the title compound as a tan oil (680 mg, 81%). ESI-MS m/z [M+H]⁺ calc'd for $C_{11}H_{14}BrN_3$, 268. found 268.

Preparation 25: tert-Butyl 4-(5-(1-aminopropyl)-1-methyl-1H-pyrrolo[3,2-b]pyridin-6-yl)piperazine-1-carboxylate

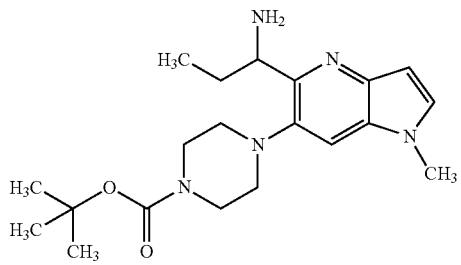 [SMILES: CCC(N)c1nc2ccn(C)c2cc1N1CCN(C(=O)OC(C)(C)C)CC1]

The title compound was prepared similar to PREPARATION 1, using 1-(6-bromo-1-methyl-1H-pyrrolo[3,2-b]pyridin-5-yl)propan-1-amine in place of (S)-1-(6-bromo-1-methyl-1H-pyrrolo[3,2-b]pyridin-5-yl)ethanamine. The crude product was used without further purification. ESI-MS m/z [M+H]$^+$ calc'd for $C_{20}H_{31}N_5O_2$, 374. found 374.

Preparation 26: tert-Butyl (S)-4-(5-(1-((2-amino-5-cyano-6-methylpyrimidin-4-yl)amino)propyl)-1-methyl-1H-pyrrolo[3,2-b]pyridin-6-yl)piperazine-1-carboxylate

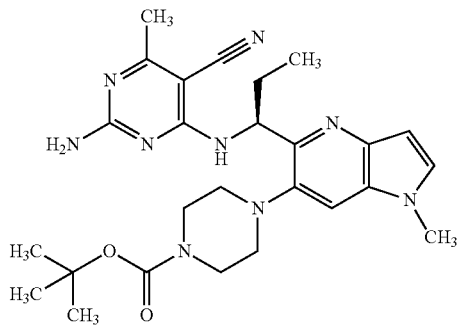 [SMILES: CC[C@H](Nc1nc(N)nc(C)c1C#N)c1nc2ccn(C)c2cc1N1CCN(C(=O)OC(C)(C)C)CC1]

The title compound was prepared similar to PREPARATION 2, using tert-butyl 4-(5-(1-aminopropyl)-1-methyl-1H-pyrrolo[3,2-b]pyridin-6-yl)piperazine-1-carboxylate in place of tert-butyl (S)-4-(5-(1-aminoethyl)-1-methyl-1H-pyrrolo[3,2-b]pyridin-6-yl)piperazine-1-carboxylate. The desired enantiomer was isolated by chiral HPLC as an off-white solid. ESI-MS m/z [M+H]$^+$ calc'd for $C_{26}H_{35}N_9O_2$, 506. found 506.

Example 1

(S)-2-Amino-4-methyl-6-(1-(1-methyl-6-(piperazin-1-yl)-1H-pyrrolo[3,2-b]pyridin-5-yl)ethylamino)pyrimidine-5-carbonitrile

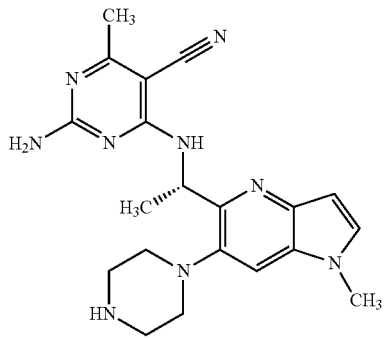

To a 100 mL round-bottom flask was added tert-butyl (S)-4-(5-(1-(2-amino-5-cyano-6-methylpyrimidin-4-yl)amino)ethyl)-1-methyl-1H-pyrrolo[3,2-b]pyridin-6-yl)piperazine-1-carboxylate (740 mg, 1.51 mmol) in ether (9 mL). At room temperature, 1.0 M HCl in ether (35 mL) was added. After stirring for about 2 hours at room temperature, an additional 3.5 mL of 1.0 M HCl in ether was added, and the mixture was stirred for another 1 hour. A yellow solid was then collected on a fritted glass filter funnel under nitrogen, and the solid was washed three times with ether to give an HCl salt of the title product. The solid was dispersed in water (120 mL) to give a yellow solution. To this solution was added saturated $NaHCO_3$ (30 mL) and a solid began to precipitate at a pH of about 8. The mixture was stirred vigorously while 2-propanol (15 mL) was added. The orange solution was warmed gently until most of the solid was dissolved, and the undissolved residue was removed by filtration. The clear filtrate was then stirred in an Erlenmeyer flask under a stream of nitrogen. A white solid began to form after 5 minutes, and the nitrogen flow was removed. The mixture was stirred for 24 hours. The white solid product was collected on a fritted glass funnel, washed with water (3×), and then dried in a stream of nitrogen. The filtrate was stirred for 2 hours, yielding additional solid, which was collected on a fritted glass funnel. The two batches of off-white solids were combined (420 mg) and were taken up in diethyl ether (10 mL). After sonication, the suspension was stirred overnight to remove residual non-polar impurities. The solids were collected on a fritted glass funnel and dried under a stream of nitrogen for 1 hour. The solid was then dried in a vacuum oven at 50° C. for 20 hours to give the title compound as a white solid (398 mg, 67%). $^1$H NMR (400 MHz, DMSO-d$_6$) δ ppm 1.42 (s, 3H), 2.24 (s, 3H), 2.69 (d, J=7.33 Hz, 2H), 2.81-2.99 (m, 6H), 3.81 (s, 3H), 5.74-5.87 (m, 1H), 6.49 (d, J=3.03 Hz, 1H), 7.01 (d, J=7.58 Hz, 3H), 7.56 (d, J=3.28 Hz, 1H), 7.80 (s, 1H); ESI-MS m/z [M+H]$^+$ calc'd for $C_{20}H_{25}N_9$, 392. found 392.

Example 2

(S)-4-(1-(6-(1,4-Diazepan-1-yl)-1-methyl-1H-pyrrolo[3,2-b]pyridin-5-yl)ethylamino)-2-amino-6-methylpyrimidine-5-carbonitrile

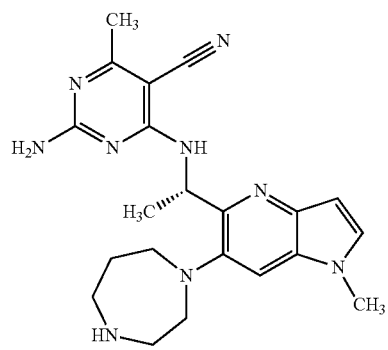 [SMILES: Cc1nc(N)nc(N[C@@H](C)c2nc3ccn(C)c3cc2N2CCCNCC2)c1C#N]

To a 25 mL pear flask was added tert-butyl (S)-4-(5-(1-(2-amino-5-cyano-6-methylpyrimidin-4-yl)amino)ethyl)-1-methyl-1H-pyrrolo[3,2-b]pyridin-6-yl)-1,4-diazepane-1-carboxylate (75 mg, 0.148 mmol) in dichloromethane (0.8 mL) to give a solution. To this solution was added TFA (0.27 mL) and the mixture was stirred at room temperature for 30 minutes. All the volatiles were removed in vacuo, and the residue was re-suspended in toluene and concentrated to remove residual TFA. The residue was then diluted in ACN and water (total of about 90 mL), followed by the addition of 2 N HCl (4 mL). The mixture was then lyophilized to give an HCl salt of the title compound as a yellow solid. $^1$H NMR (400 MHz, DMSO-d$_6$) δ ppm 1.62-1.82 (m, 3H), 2.12 (br s, 2H), 2.41 (s, 3H), 3.11 (dt, J=12.32, 5.84 Hz, 1H), 3.19-3.56 (m, 7H), 3.97 (s, 3H), 5.92 (quin, J=6.95 Hz, 1H), 6.75-7.01 (m, 1H), 7.50-8.36 (m, 2H), 8.52-9.00 (m, 1H), 9.63 (br s, 1H); ESI-MS m/z [M+H]$^+$ calc'd for C$_{21}$H$_{27}$N$_9$, 406. found 406.

Example 3

2-Amino-4-methyl-6-((S)-1-(1-methyl-6-((S)-3-(methylamino)pyrrolidin-1-yl)-1H-pyrrolo[3,2-b]pyridin-5-yl)ethylamino)pyrimidine-5-carbonitrile

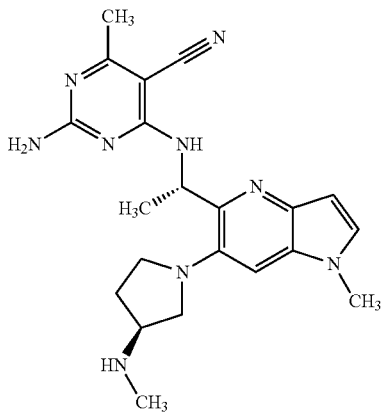 [SMILES: CN[C@H]1CCN(c2cc3c(ccn3C)nc2[C@H](C)Nc2nc(N)nc(C)c2C#N)C1]

To a 25 mL pear flask was added tert-butyl ((S)-1-(5-((S)-1-((2-amino-5-cyano-6-methylpyrimidin-4-yl)amino)ethyl)-1-methyl-1H-pyrrolo[3,2-b]pyridin-6-yl)pyrrolidin-3-yl)(methyl)carbamate (61 mg, 0.121 mmol) in dichloromethane (0.8 mL) to give a solution. To this solution was added TFA (0.27 mL), and the mixture was stirred at room temperature for 18 hours. All the volatiles were removed in vacuo, and the residue was re-suspended in toluene and concentrated to remove residual TFA. The residue was then diluted in ACN and water (total of about 90 mL), followed by the addition of 2 N HCl (4 mL). The mixture was then lyophilized to give an HCl salt of the title compound as a yellow-green solid (41 mg, 84%). $^1$H NMR (400 MHz, DMSO-d$_6$) δ ppm 1.66 (d, J=6.82 Hz, 2H), 2.17 (td, J=12.69, 7.20 Hz, 1H), 2.31-2.45 (m, 3H), 2.61 (s, 2H), 3.20-3.39 (m, 2H), 3.46 (br s, 1H), 3.57 (br s, 1H), 3.95 (s, 3H), 5.91 (t, J=6.95 Hz, 1H), 6.79 (br s, 1H), 7.68 (br s, 1H), 8.03 (br s, 1H), 8.48 (br s, 1H), 8.77 (br s, 1H), 9.32-9.50 (m, 1H), 9.60-9.82 (m, 1H); ESI-MS m/z [M+H]$^+$ calc'd for C$_{21}$H$_{27}$N$_9$, 406. found 406.

Example 4

2-Amino-4-((S)-1-(6-((R)-3-aminopiperidin-1-yl)-1-methyl-1H-pyrrolo[3,2-b]pyridin-5-yl)ethylamino)-6-methylpyrimidine-5-carbonitrile

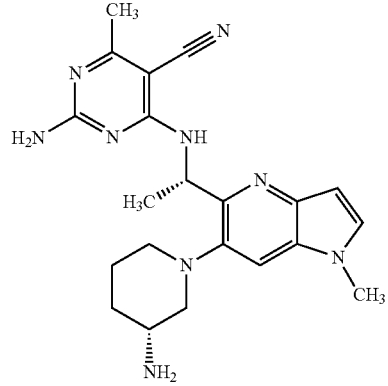 [SMILES: Cc1nc(N)nc(N[C@@H](C)c2nc3ccn(C)c3cc2N2CCC[C@@H](N)C2)c1C#N]

To a 25 mL pear flask were added 2-amino-4-(((S)-1-(6-((R)-3-(1,3-dioxoisoindolin-2-yl)piperidin-1-yl)-1-methyl-1H-pyrrolo[3,2-b]pyridin-5-yl)ethyl)amino)-6-methylpyrimidine-5-carbonitrile (20 mg, 0.037 mmol) and hydrazine monohydrate (0.027 mL, 0.56 mmol) in ethanol (1 mL). The mixture was heated to 60° C. for 8 hours and then at room temperature overnight. Additional hydrazine (30 eq, 0.054 mL) was added and the mixture was heated for another 4 hours. The crude reaction mixture was diluted with acetonitrile and was then purified by preparative HPLC (basic mode, 20-45% ACN/water gradient). The product-containing fractions were combined and lyophilized to give the title compound as a light brown solid (4.0 mg, 28%). The absolute configuration of the stereocenter on the piperidine ring was not determined, but was assigned the opposite configuration of EXAMPLE 5. $^1$H NMR (400 MHz, DMSO-d$_6$) δ ppm 1.41 (d, J=6.57 Hz, 3H), 1.72-1.99 (m, 3H), 2.09-2.22 (m, 1H), 2.27-2.36 (m, 3H), 2.56-2.73 (m, 3H), 3.47 (ddd, J=9.09, 7.20, 4.93 Hz, 1H), 3.59-3.66 (m, 1H), 3.67-3.73 (m, 3H), 5.19 (br s, 2H), 5.77-5.95 (m, 1H), 6.57 (d, J=3.28 Hz, 1H), 6.93-7.07 (m, 1H), 7.12-7.16 (m, 1H), 7.17-7.23 (m, 2H), 7.40 (s, 1H); ESI-MS m/z [M+H]$^+$ calc'd for C$_{21}$H$_{27}$N$_9$, 406. found 406.

Example 5

2-Amino-4-((S)-1-(6-((S)-3-aminopiperidin-1-yl)-1-methyl-1H-pyrrolo[3,2-b]pyridin-5-yl)ethylamino)-6-methylpyrimidine-5-carbonitrile

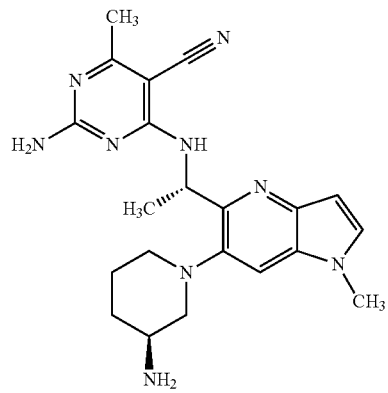

To a 25 mL pear flask were added 2-amino-4-(((S)-1-(6-((S)-3-(1,3-dioxoisoindolin-2-yl)piperidin-1-yl)-1-methyl-1H-pyrrolo[3,2-b]pyridin-5-yl)ethyl)amino)-6-methylpyrimidine-5-carbonitrile (20 mg, 0.037 mmol) and hydrazine monohydrate (0.081 mL, 1.7 mmol) in ethanol (1 mL). The mixture was heated to 65° C. for 4 hours. The mixture was diluted with acetonitrile and was then directly purified by preparative HPLC (basic mode, 25-45% ACN/water gradient). The product-containing fractions were combined and lyophilized to give the title compound as a light brown solid (6.9 mg, 46%). The absolute configuration of the stereocenter on the piperidine ring was not determined, but was assigned the opposite configuration of EXAMPLE 4. $^1$H NMR (400 MHz, DMSO-$d_6$) δ ppm 1.50-1.56 (m, 3H), 1.84-1.96 (m, 1H), 2.01-2.12 (m, 2H), 2.14-2.26 (m, 2H), 2.31 (s, 4H), 2.57 (d, J=4.55 Hz, 2H), 2.89-2.99 (m, 1H), 3.43-3.51 (m, 1H), 3.59-3.67 (m, 1H), 3.78-3.85 (m, 3H), 6.27 (s, 1H), 6.53-6.56 (m, 1H), 7.43-7.47 (m, 1H), 7.88 (s, 1H); ESI-MS m/z [M+H]$^+$ calc'd for $C_{21}H_{27}N_9$, 406. found 406.

Example 6

2-Amino-4-methyl-6-((S)-1-(1-methyl-6-((S)-3-methylpiperazin-1-yl)-1H-pyrrolo[3,2-b]pyridin-5-yl)ethylamino)pyrimidine-5-carbonitrile

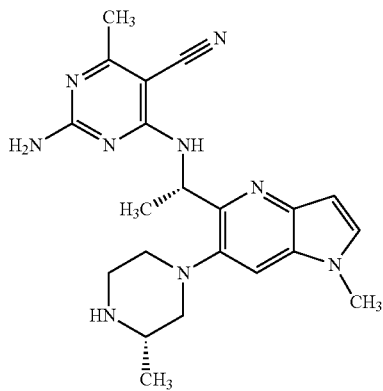

To a 200 mL pear flask was added tert-butyl (S)-4-(5-((S)-1-(2-amino-5-cyano-6-methylpyrimidin-4-yl)amino)ethyl)-1-methyl-1H-pyrrolo[3,2-b]pyridin-6-yl)-2-methylpiperazine-1-carboxylate (1.60 g, 3.16 mmol) in ether (92 mL) to give a light yellow solution. To this solution was added 2 N HCl in ether (55 mL). The resulting yellow suspension was stirred at room temperature for a total of 24 hours. The suspension was subsequently filtered on a fritted-glass funnel to collect a light yellow precipitate, which was washed with cold ether (2×) and then dried under a stream of nitrogen. The fine yellow powder was then dissolved in water and the solution was neutralized with saturated NaHCO$_3$. The final pH was increased to about 10 with K$_2$CO$_3$. The oily product was extracted into ethyl acetate (3×). The organic layers were combined, dried over MgSO$_4$, filtered, and concentrated to give an off-white solid. This residue was re-dissolved in a 1:1 mixture of acetonitrile and 2-propanol and was purified by preparative HPLC (basic mode, 20-55% ACN/water gradient). The product-containing fractions were combined and concentrated to near dryness. The residue was then re-dissolved in 2-propanol (about 10 mL) and the product gradually crystallized out of solution. After 2 hours, a white solid was collected on a fritted-glass funnel. The solid was washed with chilled 2-propanol (2×) and dried under a stream of nitrogen overnight. The solid was further dried in vacuo to give the title compound as a white solid (476 mg, 37.1%). $^1$H NMR (400 MHz, DMSO-$d_6$) δ ppm 0.90 (d, J=6.32 Hz, 3H), 1.41 (d, J=6.57 Hz, 3H), 2.08 (br s, 1H), 2.14-2.30 (m, 4H), 2.73-2.87 (m, 2H), 2.88-3.05 (m, 4H), 3.77-3.85 (m, 3H), 5.75-5.92 (m, 1H), 6.45-6.56 (m, 1H), 6.88-7.20 (m, 3H), 7.56 (d, J=3.28 Hz, 1H), 7.79 (s, 1H); ESI-MS m/z [M+H]$^+$ calc'd for $C_{21}H_{27}N_9$, 406. found 406.

Example 7

2-Amino-4-((S)-1-(6-((R)-3-aminopyrrolidin-1-yl)-1-methyl-1H-pyrrolo[3,2-b]pyridin-5-yl)ethylamino)-6-methylpyrimidine-5-carbonitrile

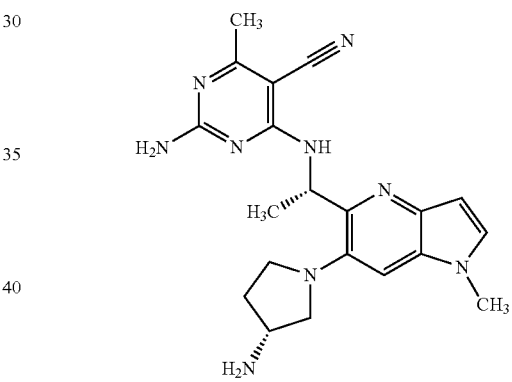

To a 25 mL pear flask was added 2-amino-4-(((S)-1-(6-(3-(1,3-dioxoisoindolin-2-yl)pyrrolidin-1-yl)-1-methyl-1H-pyrrolo[3,2-b]pyridin-5-yl)ethyl)amino)-6-methylpyrimidine-5-carbonitrile (peak 1 of PREPARATION 13, 27 mg, 0.052 mmol) in ethanol (520 μL) to give a solution. To this solution was added hydrazine monohydrate (25 μL, 0.52 mmol). The mixture was heated to 65° C. for 3.5 hours, at which time the reaction was deemed to be complete based on MS/UPLC. The mixture was diluted with acetonitrile and was directly purified by preparative HPLC (basic mode, 25-45% ACN/water gradient). The product-containing fractions were concentration and lyophilized to give the title compound as a white solid (6.3 mg, 31%). The absolute configuration of the stereocenter on the pyrrolidine ring was not determined, but was assigned the opposite configuration of EXAMPLE 8. $^1$H NMR (400 MHz, DMSO-$d_6$) δ ppm 1.41 (d, J=6.32 Hz, 3H), 1.63-1.74 (m, 1H), 2.16 (dd, J=12.25, 7.20 Hz, 1H), 2.25 (s, 3H), 2.71 (dd, J=9.09, 4.80 Hz, 1H), 3.04 (td, J=8.27, 5.18 Hz, 1H), 3.60 (t, J=6.32 Hz, 1H), 3.71-3.85 (m, 3H), 5.75 (d, J=6.82 Hz, 1H), 6.42-6.51 (m, 1H), 7.18 (d, J=7.58 Hz, 1H), 7.51 (d, J=3.28 Hz, 1H), 7.68-7.78 (m, 1H); ESI-MS m/z [M+H]$^+$ calc'd for $C_{20}H_{25}N_9$, 392. found 392.

Example 8

2-Amino-4-((S)-1-(6-((S)-3-aminopyrrolidin-1-yl)-1-methyl-1H-pyrrolo[3,2-b]pyridin-5-yl)ethylamino)-6-methylpyrimidine-5-carbonitrile

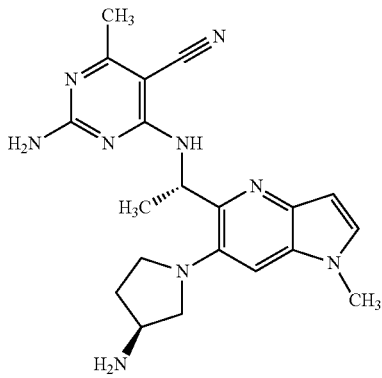 [SMILES: Cc1nc(N)nc(N[C@@H](C)c2nc3ccn(C)c3cc2N2CC[C@H](N)C2)c1C#N]

To a 25 mL pear flask were added 2-amino-4-(((S)-1-(6-(3-(1,3-dioxoisoindolin-2-yl)pyrrolidin-1-yl)-1-methyl-1H-pyrrolo[3,2-b]pyridin-5-yl)ethyl)amino)-6-methylpyrimidine-5-carbonitrile (peak 2 of PREPARATION 13, 10 mg, 0.019 mmol) and hydrazine monohydrate (0.019 mL, 0.38 mmol) in ethanol (2 mL). The mixture was heated to 75° C. for 3 hours, then diluted with acetonitrile, and directly purified by preparative HPLC (basic mode, 20-45% ACN/water gradient). The product-containing fractions were combined, concentrated, and lyophilized to give the title compound as a white solid (6.9 mg, 92%). The absolute configuration of the stereocenter on the pyrrolidine ring was not determined, but was assigned the opposite configuration of EXAMPLE 7. $^1$H NMR (400 MHz, DMSO-$d_6$) δ ppm 1.41 (d, J=6.32 Hz, 3H), 1.63-1.74 (m, 1H), 2.16 (dd, J=12.25, 7.20 Hz, 1H), 2.25 (s, 3H), 2.71 (dd, J=9.09, 4.80 Hz, 1H), 3.04 (td, J=8.27, 5.18 Hz, 1H), 3.60 (t, J=6.32 Hz, 1H), 3.71-3.85 (m, 3H), 5.75 (d, J=6.82 Hz, 1H), 6.42-6.51 (m, 1H), 7.07 (br s, 2H), 7.18 (d, J=7.58 Hz, 1H), 7.51 (d, J=3.28 Hz, 1H), 7.68-7.78 (m, 1H); ESI-MS m/z [M+H]$^+$ calc'd for $C_{20}H_{25}N_9$, 392. found 392.

Example 9

2-Amino-4-methyl-6-((S)-1-(1-methyl-6-((R)-3-methylpiperazin-1-yl)-1H-pyrrolo[3,2-b]pyridin-5-yl)ethylamino)pyrimidine-5-carbonitrile

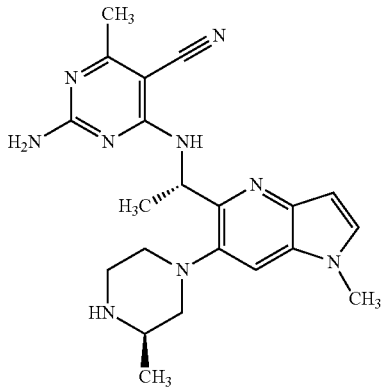 [SMILES: Cc1nc(N)nc(N[C@@H](C)c2nc3ccn(C)c3cc2N2CCN[C@H](C)C2)c1C#N]

To a 25 mL pear flask was added tert-butyl (R)-4-(5-((S)-1-(2-amino-5-cyano-6-methylpyrimidin-4-yl)amino)ethyl)-1-methyl-1H-pyrrolo[3,2-b]pyridin-6-yl)-2-methylpiperazine-1-carboxylate (0.051 g, 0.10 mmol) in dichloromethane (0.75 mL) to give a solution. To this solution was added trifluoroacetic acid (0.25 mL, 2.9 mmol) at room temperature. The mixture was stirred for 15 minutes, at which time the reaction was deemed to be complete based on UPLC/MS. The reaction mixture was then poured into saturated NaHCO$_3$ and the pH was adjusted to about 11 with K$_2$CO$_3$. The aqueous mixture was then extracted with EtOAc (2×). The organic layers were combined, dried over MgSO$_4$, filtered, and concentrated to give the title compound as a light brown film (0.041 g, 100%). $^1$H NMR (400 MHz, CD$_3$OD) δ ppm 1.33 (d, J=6.57 Hz, 3H), 1.52 (d, J=6.57 Hz, 3H), 2.31 (s, 3H), 2.82-2.93 (m, 1H), 2.96-3.06 (m, 1H), 3.07-3.14 (m, 1H), 3.15-3.22 (m, 1H), 3.24-3.31 (m, 1H), 3.32 (dt, J=3.28, 1.64 Hz, 1H), 3.35-3.39 (m, 1H), 3.39-3.48 (m, 1H), 3.83 (s, 3H), 6.05 (q, J=6.65 Hz, 1H), 6.54 (d, J=3.28 Hz, 1H), 7.44 (d, J=3.28 Hz, 1H), 7.79 (s, 1H); ESI-MS m/z [M+H]$^+$ calc'd for $C_{21}H_{27}N_9$, 406. found 406.

Example 10

2-Amino-4-methyl-6-((S)-1-(1-methyl-6-((S)-pyrrolidin-3-yl)-1H-pyrrolo[3,2-b]pyridin-5-yl)ethylamino)pyrimidine-5-carbonitrile

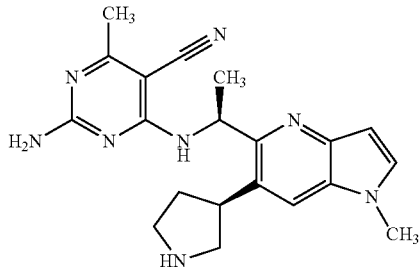 [SMILES: Cc1nc(N)nc(N[C@@H](C)c2nc3ccn(C)c3cc2[C@@H]2CCNC2)c1C#N]

In a 25 mL pear flask was dissolved tert-butyl (S)-3-(5-((S)-1-(2-amino-5-cyano-6-methylpyrimidin-4-yl)amino)ethyl)-1-methyl-1H-pyrrolo[3,2-b]pyridin-6-yl)pyrrolidine-1-carboxylate (peak 2 of PREPARATION 18, 32 mg, 0.067 mmol) in CH$_2$Cl$_2$ (750 μL) to give a light yellow solution. To this solution was added, at room temperature, trifluoroacetic acid (250 μL, 2.0 mmol). The mixture was stirred at room temperature for 1 hour. The volatiles were removed in vacuo. Toluene was added and residual TFA was removed by azeotropic distillation in vacuo. The residue was triturated with ether, and the solid was diluted in water (15 mL). The solution was then lyophilized to give a TFA salt of the title compound as a white powder (34 mg, 100%). The absolute configuration of the stereocenter on the pyrrolidine ring was not determined, but was assigned the opposite configuration of EXAMPLE 11. $^1$H NMR (400 MHz, DMSO-$d_6$) δ ppm 1.56 (d, J=5.56 Hz, 3H), 2.12 (d, J=7.83 Hz, 1H), 2.32 (br s, 3H), 2.33 (m, 1H), 3.27-3.43 (m, 2H), 3.51 (br s, 1H), 3.66 (br s, 1H), 3.90 (s, 3H), 3.90 (m, 1H), 5.60-5.77 (m, 1H), 6.64 (br s, 1H), 7.45 (br s, 1H), 7.86 (br s, 2H), 8.28 (br s, 1H), 8.95 (br s, 1H), 9.20 (br s, 1H); ESI-MS m/z [M+H]$^+$ calc'd for $C_{20}H_{24}N_8$, 377. found 377.

Example 11

2-Amino-4-methyl-6-((S)-1-(1-methyl-6-((R)-pyrrolidin-3-yl)-1H-pyrrolo[3,2-b]pyridin-5-yl)ethylamino)pyrimidine-5-carbonitrile

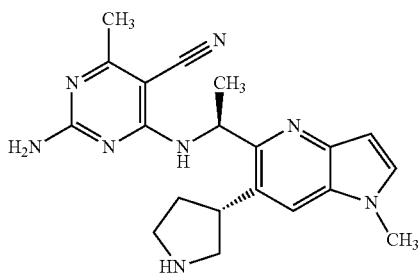 [SMILES: Cc1nc(N)nc(N[C@@H](C)c2nc3ccn(C)c3cc2[C@H]2CCNC2)c1C#N]

In a 25 mL pear flask was dissolved tert-butyl (R)-3-(5-((S)-1-(2-amino-5-cyano-6-methylpyrimidin-4-yl)amino)ethyl)-1-methyl-1H-pyrrolo[3,2-b]pyridin-6-yl)pyrrolidine-1-carboxylate (peak 1 of PREPARATION 18, 13 mg, 0.027 mmol) in CH$_2$Cl$_2$ (500 µL) to give a light yellow solution. To this solution was added, at room temperature, trifluoroacetic acid (150 µL, 2.0 mmol). The mixture was stirred at room temperature for 1 hour. The volatiles were removed in vacuo. Toluene was added and residual TFA was removed by azeotropic distillation in vacuo. The residue was triturated with ether, and the solid was diluted in water (15 mL). The solution was lyophilized to give a TFA salt of the title compound as a white powder. The absolute configuration of the stereocenter on the pyrrolidine ring was not determined, but was assigned the opposite configuration of EXAMPLE 10. $^1$H NMR (400 MHz, DMSO-d$_6$) δ ppm 1.56 (d, J=5.81 Hz, 3H), 2.12-2.26 (m, 1H), 2.27-2.34 (m, 2H), 2.36-2.47 (m, 1H), 3.34 (dd, J=16.29, 7.20 Hz, 2H), 3.55 (d, J=3.79 Hz, 1H), 3.76 (d, J=3.28 Hz, 1H), 3.84-4.03 (m, 3H), 5.56-5.78 (m, 2H), 6.55-6.69 (m, 1H), 6.98 (br s, 1H), 7.10-7.29 (m, 1H), 7.45 (br s, 1H), 7.70 (br s, 1H), 7.89 (br s, 1H), 8.31 (br s, 1H), 8.76-8.99 (m, 1H), 9.12 (br s, 1H); ESI-MS m/z [M+H]$^+$ calc'd for C$_{20}$H$_{24}$N$_8$, 377. found 377.

Example 12

(S)-2-Amino-4-methyl-6-(1-(1-methyl-6-(piperidin-4-yl)-1H-pyrrolo[3,2-b]pyridin-5-yl)ethylamino)pyrimidine-5-carbonitrile

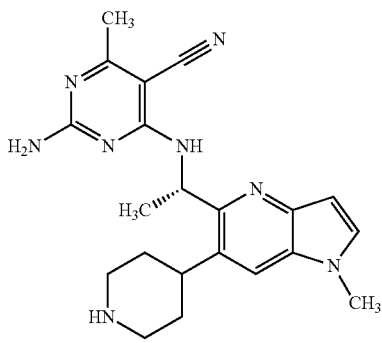

To a 100 mL pear flask was added tert-butyl (S)-4-(5-(1-(2-amino-5-cyano-6-methylpyrimidin-4-yl)amino)ethyl)-1-methyl-1H-pyrrolo[3,2-b]pyridin-6-yl)piperidine-1-carboxylate (25 mg, 0.051 mmol) in dichloromethane (0.75 mL) to give a solution. To this solution was added TFA (0.25 mL). The mixture was stirred at room temperature for 35 minutes. All the volatiles were removed in vacuo, and the residue was re-suspended in toluene and concentrated to remove residual TFA. The residue was then diluted in ACN and water (total of about 90 mL), followed by the addition of 2 N HCl (4 mL). The mixture was lyophilized to give an HCl salt of the title compound as an off-white solid (21.5 mg, 91%). $^1$H NMR (400 MHz, DMSO-d$_6$) δ ppm 1.76 (d, J=6.57 Hz, 2H), 1.85 (d, J=13.39 Hz, 1H), 2.00 (br s, 1H), 2.04-2.09 (m, 1H), 2.08-2.27 (m, 2H), 2.31-2.42 (m, 3H), 3.04-3.24 (m, 2H), 3.26-3.67 (m, 3H), 3.99 (s, 3H), 5.81 (quin, J=6.88 Hz, 1H), 6.79-6.99 (m, 1H), 7.68 (br s, 1H), 8.11 (br s, 1H), 8.44 (br s, 1H), 8.69 (br s, 1H), 9.09 (br s, 1H), 9.41 (br s, 1H), 9.67 (br s, 1H); ESI-MS m/z [M+H]$^+$ calc'd for C$_{21}$H$_{26}$N$_8$, 391. found 391.

Example 13

(S)-2,4-Diamino-6-(1-(1-methyl-6-(piperazin-1-yl)-1H-pyrrolo[3,2-b]pyridin-5-yl)ethylamino)pyrimidine-5-carbonitrile

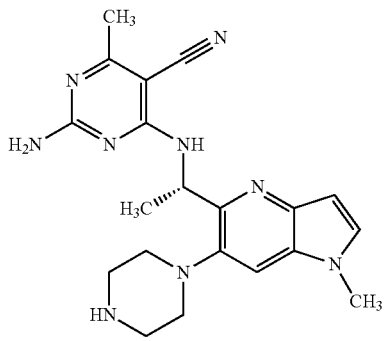

To a 25 mL pear flask was added tert-butyl (S)-4-(5-(1-((2,6-diamino-5-cyanopyrimidin-4-yl)amino)ethyl)-1-methyl-1H-pyrrolo[3,2-b]pyridin-6-yl)piperazine-1-carboxylate (10 mg, 0.020 mmol) in dioxane (0.4 mL) to give a solution. To this solution was added, slowly and at room temperature, 4 M hydrogen chloride in dioxane (0.1 mL, 0.4 mmol) resulting in the gradual formation of a precipitate. The solid was collected on a fritted glass funnel and was dried overnight under a stream of nitrogen to give an HCl salt of the title compound as a light yellow solid (9.2 mg, 97%). $^1$H NMR (400 MHz, DMSO-d$_6$) δ ppm 1.59 (d, J=5.81 Hz, 3H), 3.01-3.14 (m, 2H), 3.23-3.37 (m, 6H), 3.94 (s, 3H), 5.67-5.92 (m, 1H), 6.73 (br s, 1H), 7.84-8.61 (m, 6H), 9.44 (br s, 2H); ESI-MS m/z [M+H]$^+$ calc'd for C$_{19}$H$_{24}$N$_{10}$, 393. found 393.

Example 14

4-((S)-1-(6-((1S,4S)-2,5-Diazabicyclo[2.2.1]heptan-2-yl)-1-methyl-1H-pyrrolo[3,2-b]pyridin-5-yl)ethylamino)-2-amino-6-methylpyrimidine-5-carbonitrile

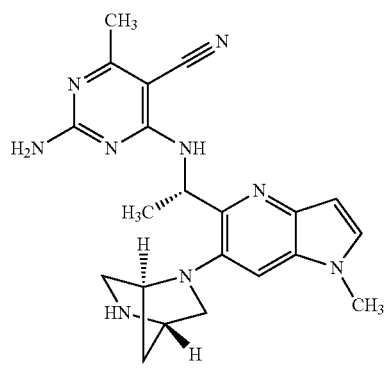 [SMILES: Cc1nc(N)nc(N[C@@H](C)c2nc3ccn(C)c3cc2N2C[C@@H]3C[C@H]2CN3)c1C#N]

To a 100 mL pear flask was added tert-butyl (1S,4S)-5-(5-((S)-1-((2-amino-5-cyano-6-methylpyrimidin-4-yl)amino)ethyl)-1-methyl-1H-pyrrolo[3,2-b]pyridin-6-yl)-2,5-diazabicyclo[2.2.1]heptane-2-carboxylate (220 mg, 0.44 mmol) in dichloromethane (4.5 mL) to give a solution. To this solution was added TFA (1.5 mL). The mixture was stirred at room temperature for 30 minutes. All the volatiles were removed in vacuo, and the residue was re-suspended in toluene and concentrated to remove residual TFA. The residue was then diluted in ACN and water (total of about 90 mL), followed by the addition of 2 N HCl (4 mL). The mixture was lyophilized to give an HCl salt of the title compound as a yellow-green solid (160 mg, 78%). $^1$H NMR (400 MHz, DMSO-$d_6$) δ ppm 1.67 (d, J=7.07 Hz, 3H), 2.00 (d, J=10.61 Hz, 1H), 2.33 (br s, 1H), 2.43 (s, 3H), 3.09-3.25 (m, 1H), 3.45 (d, J=10.11 Hz, 2H), 3.96-4.06 (m, 4H), 4.10-4.18 (m, 1H), 4.49 (br s, 1H), 5.95 (quin, J=6.88 Hz, 1H), 6.78 (d, J=2.27 Hz, 1H), 7.76 (br s, 1H), 8.03 (br s, 1H), 8.25 (br s, 1H), 8.63 (br s, 1H), 9.08 (br s, 1H), 9.78 (br s, 1H), 10.19 (br s, 1H); ESI-MS m/z [M+H]$^+$ calc'd for $C_{21}H_{25}N_9$, 404. found 404.

Example 15

(S)-2-Amino-4-methyl-6-((1-(1-methyl-6-(piperidin-4-ylamino)-1H-pyrrolo[3,2-b]pyridin-5-yl)ethyl)amino)pyrimidine-5-carbonitrile

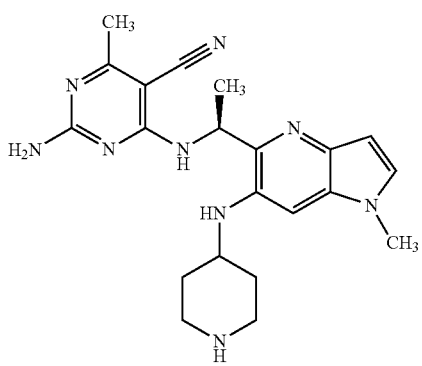 [SMILES: Cc1nc(N)nc(N[C@@H](C)c2nc3ccn(C)c3cc2NC2CCNCC2)c1C#N]

Step A: tert-Butyl (S)-4-((5-(1-aminoethyl)-1-methyl-1H-pyrrolo[3,2-b]pyridin-6-yl)amino)piperidine-1-carboxylate

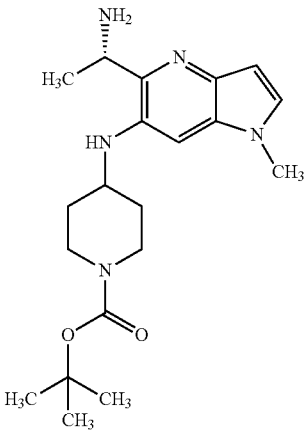 [SMILES: C[C@H](N)c1nc2ccn(C)c2cc1NC1CCN(C(=O)OC(C)(C)C)CC1]

To a suspension of potassium tert-butoxide (44.2 mg, 0.394 mmol) and tert-butyl 4-aminopiperidine-1-carboxylate (79 mg, 0.394 mmol) in dioxane (2 mL), was added dropwise at 90° C., a solution of (S)-1-(6-bromo-1-methyl-1H-pyrrolo[3,2-b]pyridin-5-yl)ethan-1-amine (50 mg, 0.197 mmol) in dioxane (1 mL). After 2 hours LCMS showed the reaction was complete. The volatiles were removed by nitrogen flow. The crude title compound was used without further purification. ESI-MS m/z [M+H]$^+$ calc'd for $C_{20}H_{31}N_5O_2$, 374. found 374.

Step B: tert-Butyl (S)-4-((5-(1-((2-amino-5-cyano-6-methylpyrimidin-4-yl)amino)ethyl)-1-methyl-1H-pyrrolo[3,2-b]pyridin-6-yl)amino)piperidine-1-carboxylate

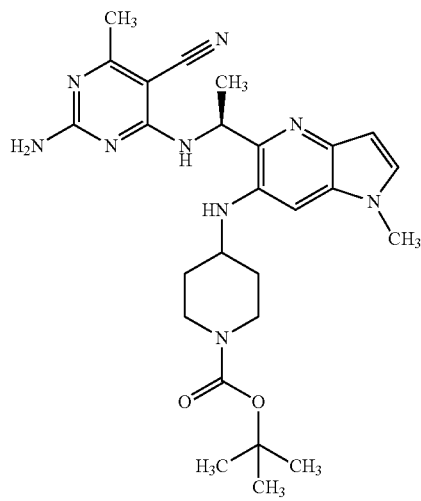 [SMILES: Cc1nc(N)nc(N[C@@H](C)c2nc3ccn(C)c3cc2NC2CCN(C(=O)OC(C)(C)C)CC2)c1C#N]

To crude tert-butyl (S)-4-((5-(1-aminoethyl)-1-methyl-1H-pyrrolo[3,2-b]pyridin-6-yl)amino)piperidine-1-carboxylate was added HOAc (2 drops), followed by ACN (2 mL), 2-amino-4-chloro-6-methylpyrimidine-5-carbonitrile (0.083 g, 0.493 mmol), and DIPEA (0.344 mL, 1.970 mmol). The reaction mixture was stirred at 75° C. for 1 hour. LCMS showed the reaction was complete, though messy. The volatiles were removed by $N_2$ flow. The crude title compound was used without further purification. ESI-MS m/z [M+H]$^+$ calc'd for $C_{26}H_{35}N_9O_2$, 506. found 506.

Step C: (S)-2-Amino-4-methyl-6-((1-(1-methyl-6-(piperidin-4-ylamino)-1H-pyrrolo[3,2-b]pyridin-5-yl)ethyl)amino)pyrimidine-5-carbonitrile Crude tert-butyl (S)-4-((5-(1-(2-amino-5-cyano-6-methylpyrimidin-4-yl)amino)ethyl)-1-methyl-1H-pyrrolo[3,2-b]pyridin-6-yl)amino)piperidine-1-carboxylate was dissolved MeOH (2 mL). To this solution was added TFA (1 mL) and the reaction mixture was stirred at room temperature for 1 hour. LCMS showed the reaction was complete. The volatiles were removed by nitrogen flow. The residue was dissolved in MeOH, basified with 7 N $NH_3$ in methanol (2 drops), and purified by preparative HPLC (2×, basic mode) to give the title compound as pale yellow solid (9.6 mg, 12% over three steps). $^1$H NMR (400 MHz, $CD_3Cl$) δ ppm 7.05 (d, J=3.3 Hz, 1H), 6.72-6.87 (m, 2H), 6.57 (d, J=2.8 Hz, 1H), 5.47-5.60 (m, 1H), 5.19 (s, 2H), 3.95 (br s, 1H), 3.75 (s, 3H), 3.35-3.46 (m, 1H), 3.05-3.25 (m, 2H), 2.76 (q, J=10.4 Hz, 2H), 2.39 (s, 3H), 2.16 (d, J=12.6 Hz, 1H), 1.99-2.11 (m, 1H), 1.60 (d, J=6.6 Hz, 3H), 1.28-1.51 (m, 2H). ESI-MS m/z [M+H]$^+$ calc'd for $C_{21}H_{27}N_9$, 406. found 406.

Example 16

(S)-2-Amino-4-((1-(6-(azetidin-3-yl(methyl)amino)-1-methyl-1H-pyrrolo[3,2-b]pyridin-5-yl)ethyl)amino)-6-methylpyrimidine-5-carbonitrile

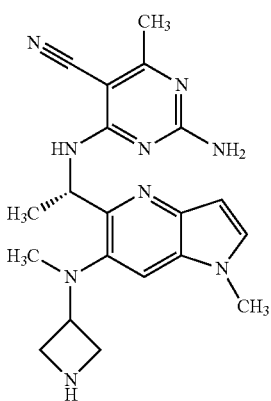 [SMILES: Cc1nc(N)nc(N[C@@H](C)c2nc3ccn(C)c3cc2N(C)C2CNC2)c1C#N]

Step A: tert-Butyl (S)-3-((5-(1-aminoethyl)-1-methyl-1H-pyrrolo[3,2-b]pyridin-6-yl)(methyl)amino)azetidine-1-carboxylate

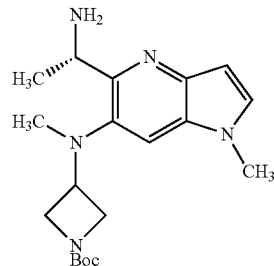 [SMILES: C[C@H](N)c1nc2ccn(C)c2cc1N(C)C1CN(C(=O)OC(C)(C)C)C1]

Into a 8 mL 2-necked round-bottom flask equipped for stirring and fitted with a septum cap were added tert-butyl 3-(methylamino)azetidine-1-carboxylate (0.220 g, 1.181 mmol), potassium tert-butoxide (0.132 g, 1.181 mmol) and 2-Me THF (2 mL). The reaction mixture was heated to 85° C. (S)-1-(6-Bromo-1-methyl-1H-pyrrolo[3,2-b]pyridin-5-yl) ethan-1-amine (0.100 g, 0.394 mmol) in 2-Me THF (2.000 mL) was added dropwise via syringe and the reaction mixture was stirred at 85° C. for 37 minutes. The reaction mixture was then cooled and partitioned between water and ethyl acetate. The organic layer was dried over anhydrous sodium sulfate, filtered, concentrated, and dried under vacuum. The crude product was purified by preparative HPLC (acid mode, 20-45% ACN/water gradient) to give the title compound as a light brown film (27.4 mg, 15%). ESI-MS m/z [M+H]$^+$ calc'd for $C_{19}H_{29}N_5O_2$, 360. found 360.

Step B: tert-Butyl (S)-3-((5-(1-((2-amino-5-cyano-6-methylpyrimidin-4-yl)amino)ethyl)-1-methyl-1H-pyrrolo[3,2-b]pyridin-6-yl)(methyl)amino)azetidine-1-carboxylate

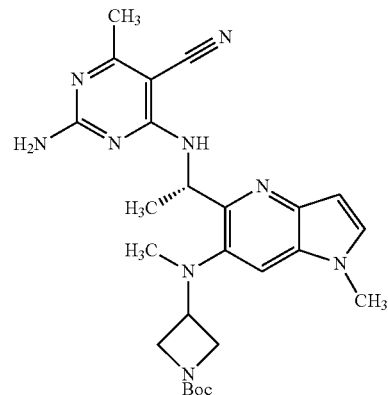 [SMILES: Cc1nc(N)nc(N[C@@H](C)c2nc3ccn(C)c3cc2N(C)C2CN(C(=O)OC(C)(C)C)C2)c1C#N]

To a solution of tert-butyl (S)-3-((5-(1-aminoethyl)-1-methyl-1H-pyrrolo[3,2-b]pyridin-6-yl)(methyl)amino)azetidine-1-carboxylate (27.4 mg, 0.060 mmol) and 2-amino-4-chloro-6-methylpyrimidine-5-carbonitrile (17.20 mg, 0.102 mmol) in DMSO (2 mL) was added triethylamine (0.046 mL, 0.330 mmol) at room temperature. The reaction mixture was stirred at 90° C. for 5 hours. The solvent was removed with a stream of nitrogen. The crude title compound was used without further purification. ESI-MS m/z [M+H]+ calc'd for C25H33N9O2, 492. found 492.

Step C: (S)-2-Amino-4-((1-(6-(azetidin-3-yl(methyl) amino)-1-methyl-1H-pyrrolo[3,2-b]pyridin-5-yl) ethyl)amino)-6-methylpyrimidine-5-carbonitrile Crude tert-butyl (S)-3-((5-(1-((2-amino-5-cyano-6-methylpyrimidin-4-yl)amino)ethyl)-1-methyl-1H-pyrrolo[3,2-b]pyridin-6-yl)(methyl)amino)azetidine-1-carboxylate was dissolved in dichloromethane (1 mL). To this solution was added TFA (0.462 mL, 6.00 mmol) at room temperature. The reaction mixture was stirred at room temperature for 5 minutes. The solvent was removed with a stream of nitrogen and the crude product was purified by preparative HPLC (acid mode, 1-25% ACN/water gradient) to give a TFA salt of the title compound as a clear film (5.9 mg, 19% over two steps). 1H NMR (400 MHz, CD3OD) δ ppm 1.73-1.82 (m, 3H), 2.49-2.56 (m, 3H), 2.82-2.89 (m, 3H), 3.94-4.08 (m, 4H), 4.19-4.33 (m, 3H), 4.46-4.57 (m, 1H), 5.97-6.09 (m, 1H), 6.70-6.77 (m, 1H), 7.85-7.94 (m, 1H), 8.32-8.47 (m, 1H). ESI-MS m/z [M+H]+ calc'd for C20H25N9, 392. found 392.

Example 17

2-Amino-4-(((1S)-1-(6-(4-aminocyclohex-1-en-1-yl)-1-methyl-1H-pyrrolo[3,2-b]pyridin-5-yl)ethyl) amino)-6-methylpyrimidine-5-carbonitrile

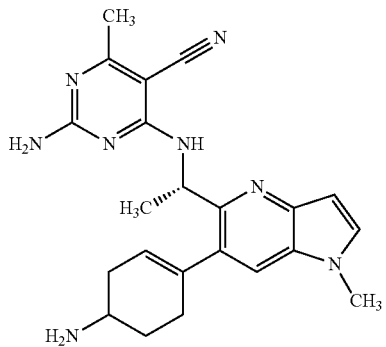 [SMILES: Cc1nc(N)nc(N[C@@H](C)c2nc3ccn(C)c3cc2C2=CCC(N)CC2)c1C#N]

Step A: (S)-2-Amino-4-((1-(6-bromo-1-methyl-1H-pyrrolo[3,2-b]pyridin-5-yl)ethyl)amino)-6-methylpyrimidine-5-carbonitrile

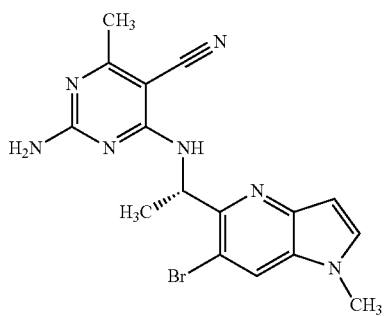 [SMILES: Cc1nc(N)nc(N[C@@H](C)c2nc3ccn(C)c3cc2Br)c1C#N]

A microwave vial was charged with (S)-1-(6-bromo-1-methyl-1H-pyrrolo[3,2-b]pyridin-5-yl)ethanamine (2 g, 7.87 mmol), 2-amino-4-chloro-6-methylpyrimidine-5-carbonitrile (1.592 g, 9.44 mmol), acetonitrile (40 mL), and DIPEA (5.50 mL, 31.5 mmol). The reaction mixture was heated to 75° C. for 1 hour in an oil bath and then cooled to room temperature. A precipitate was isolated by vacuum filtration and washed with acetonitrile to give the title compound as an off-white solid (2.85 g, 94%). ESI-MS m/z [M+H]+ calc'd for C16H16BrN7, 386. found 386.

Step B: tert-Butyl (4-(5-((S)-1-((2-amino-5-cyano-6-methylpyrimidin-4-yl)amino)ethyl)-1-methyl-1H-pyrrolo[3,2-b]pyridin-6-yl)cyclohex-3-en-1-yl)carbamate

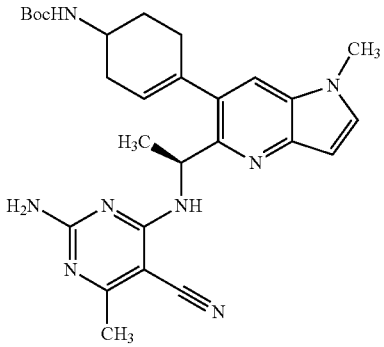 [SMILES: Cc1nc(N)nc(N[C@@H](C)c2nc3ccn(C)c3cc2C2=CCC(NC(=O)OC(C)(C)C)CC2)c1C#N]

A microwave vial was charged with (S)-2-amino-4-((1-(6-bromo-1-methyl-1H-pyrrolo[3,2-b]pyridin-5-yl)ethyl) amino)-6-methylpyrimidine-5-carbonitrile (0.07 g, 0.181 mmol), tert-butyl (4-(4,4,5,5-tetramethyl-1,3,2-dioxaborolan-2-yl)cyclohex-3-en-1-yl)carbamate (0.076 g, 0.236 mmol), PdCl2(dppf)-CH2Cl2 adduct (0.015 g, 0.018 mmol) and sodium bicarbonate (0.030 g, 0.362 mmol) in dioxane (2 mL) and water (0.500 mL). The reaction mixture was heated to 100° C. for 40 minutes in a microwave reactor. Following reaction, the solvent was removed under a nitrogen stream and the residue was partitioned between ethyl acetate (20 mL) and water (20 mL). The organic phase was dried over anhydrous sodium sulfate and purified on a silica gel column (20-80% ethyl acetate/heptanes gradient) to give the title compound as a tan solid (79 mg, 87%). ESI-MS m/z [M+H]+ calc'd for C27H34N8O2, 503. found 503.

Step C: 2-Amino-4-(((1S)-1-(6-(4-aminocyclohex-1-en-1-yl)-1-methyl-1H-pyrrolo[3,2-b]pyridin-5-yl) ethyl)amino)-6-methylpyrimidine-5-carbonitrile A round-bottom flask was charged with tert-butyl (4-(5-((S)-1-((2-amino-5-cyano-6-methylpyrimidin-4-yl)amino) ethyl)-1-methyl-1H-pyrrolo[3,2-b]pyridin-6-yl)cyclohex-3-en-1-yl)carbamate (0.079 g, 0.157 mmol), DCM (2 mL), and TFA (0.969 mL, 12.57 mmol). The reaction mixture was stirred at room temperature for 30 minutes. The solvent was evaporated using a stream of nitrogen. A portion of the crude material was purified via preparative HPLC (acid mode, 5-25% ACN/water gradient). The product-containing fractions were dried in vacuo to give the title compound as an off-white solid. 1H NMR (400 MHz, DMSO-d6) δ ppm 0.81 (d, J=6.82 Hz, 3H), 0.97-1.16 (m, 1H), 1.30-1.51 (m, 2H), 1.57 (s, 3H), 1.63-1.94 (m, 3H), 2.66 (d, J=8.84 Hz, 1H), 3.07-3.15 (m, 3H), 4.69-4.88 (m, 1H), 5.02 (br s, 1H), 5.86 (d, J=3.03 Hz, 1H), 7.05 (d, J=3.03 Hz, 1H), 7.45 (d, J=4.04 Hz, 1H); ESI-MS m/z [M+H]+ calc'd for $C_{22}H_{26}N_8$, 403. found 403.

Example 18

(S)-2-Amino-4-((1-(6-(4-aminocyclohexyl)-1-methyl-1H-pyrrolo[3,2-b]pyridin-5-yl)ethyl)amino)-6-methylpyrimidine-5-carbonitrile

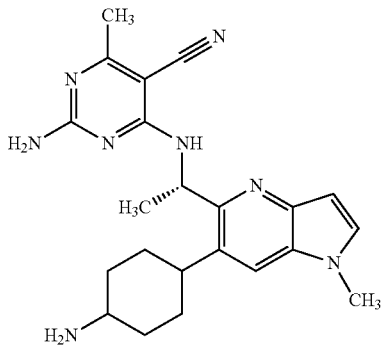 [SMILES: Cc1nc(N)nc(N[C@@H](C)c2nc3ccn(C)c3cc2C2CCC(N)CC2)c1C#N]

Step A: tert-Butyl (S)-(4-(5-(1-(2-amino-5-cyano-6-methylpyrimidin-4-yl)amino)ethyl)-1-methyl-1H-pyrrolo[3,2-b]pyridin-6-yl)cyclohexyl)carbamate

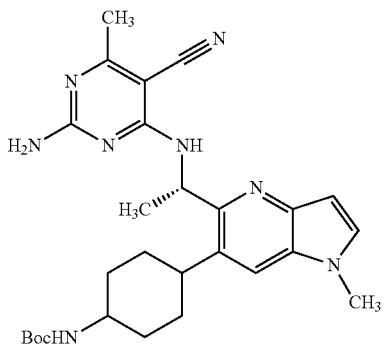 [SMILES: Cc1nc(N)nc(N[C@@H](C)c2nc3ccn(C)c3cc2C2CCC(NC(=O)OC(C)(C)C)CC2)c1C#N]

A 10 mL round-bottom flask, which was charged with tert-butyl (4-(5-((S)-1-(2-amino-5-cyano-6-methylpyrimidin-4-yl)amino)ethyl)-1-methyl-1H-pyrrolo[3,2-b]pyridin-6-yl)cyclohex-3-en-1-yl)carbamate (0.079 g, 0.157 mmol), Pd/C (0.017 g, 0.157 mmol), and ethanol (2 mL), was fitted with a hydrogen-filled balloon, purged, and stirred at room temperature overnight. The flask was subsequently re-charged with Pd/C (0.017 g, 0.157 mmol), fitted with a hydrogen-filled balloon, purged, and stirred at room temperature overnight. The reaction mixture was then filtered through a pad of Celite and the filtrate was evaporated via a stream of nitrogen. The crude product was dissolved in a mixture of DMSO and MeOH (1:1) and purified by preparative HPLC (basic mode, 65-75% ACN/water gradient). The product-containing fractions were dried in vacuo to give the title compound as an off-white solid (12 mg, 15%). ESI-MS m/z [M+H]+ calc'd for $C_{22}H_{36}N_8O_2$, 505. found 505.

Step B: (S)-2-Amino-4-((1-(6-(4-aminocyclohexyl)-1-methyl-1H-pyrrolo[3,2-b]pyridin-5-yl)ethyl)amino)-6-methylpyrimidine-5-carbonitrile A scintillation vial was charged with (S)-tert-butyl (4-(5-(1-((2-amino-5-cyano-6-methylpyrimidin-4-yl)amino)ethyl)-1-methyl-1H-pyrrolo[3,2-b]pyridin-6-yl)cyclohexyl)carbamate (0.012 g, 0.024 mmol), DCM (1 mL), and TFA (0.916 mL, 11.89 mmol). The reaction mixture was stirred at room temperature for 45 minutes. The solvent was evaporated via a stream of nitrogen. The crude product was dissolved in a mixture of DMSO and MeOH (1:1) and was purified by preparative HPLC (basic mode, 25-50% ACN/$H_2O$ gradient). The product-containing fractions were dried in vacuo to give the title compound as a white solid (5 mg, 53%). $^1$H NMR (400 MHz, $CD_3OD$) δ ppm 1.31 (br s, 1H), 1.55 (d, J=6.57 Hz, 5H), 1.62-1.82 (m, 2H), 1.85-2.04 (m, 7H), 2.05-2.26 (m, 2H), 2.36 (s, 3H), 2.94-3.12 (m, 2H), 3.84-3.89 (m, 3H), 5.77-5.97 (m, 1H), 6.57 (d, J=4.72 Hz, 1H), 7.46 (d, J=4.49 Hz, 1H), 7.94 (s, 1H), 7.78 (s, J=64.10 Hz, 1H); ESI-MS m/z [M+H]+ calc'd for $C_{22}H_{28}N_8$, 405. found 405.

Analytical HPLC analysis indicates the product is a mixture of cis/trans isomers, 2-amino-4-(((S)-1-(6-((1s,4R)-4-aminocyclohexyl)-1-methyl-1H-pyrrolo[3,2-b]pyridin-5-yl)ethyl)amino)-6-methylpyrimidine-5-carbonitrile,

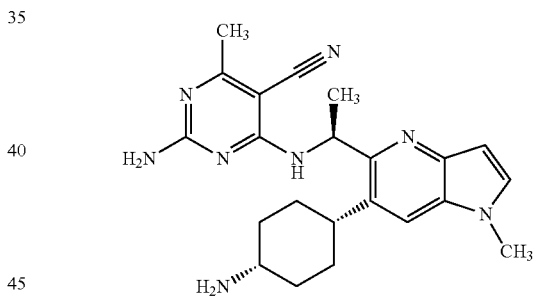

and 2-amino-4-(((S)-1-(6-((1r,4S)-4-aminocyclohexyl)-1-methyl-1H-pyrrolo[3,2-b]pyridin-5-yl)ethyl)amino)-6-methylpyrimidine-5-carbonitrile

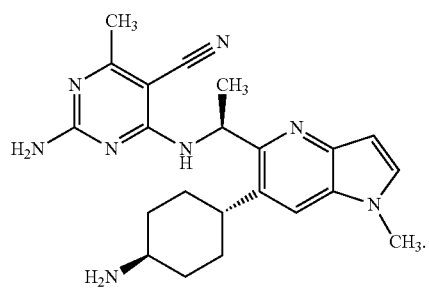 [SMILES: Cc1nc(N)nc(N[C@@H](C)c2nc3ccn(C)c3cc2[C@H]2CC[C@H](N)CC2)c1C#N]

Example 19

(S)-2-Amino-4-methyl-6-((1-(1-methyl-6-(piperazin-1-yl)-1H-pyrrolo[3,2-b]pyridin-5-yl)propyl)amino)pyrimidine-5-carbonitrile

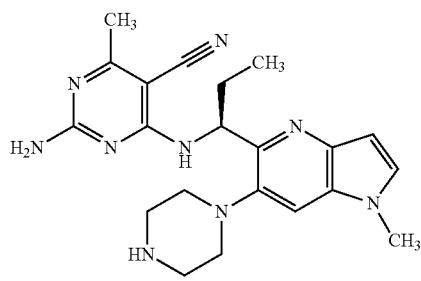 [SMILES: CC[C@H](Nc1nc(N)nc(C)c1C#N)c1nc2ccn(C)c2cc1N1CCNCC1]

The title compound was prepared similar to EXAMPLE 1, using tert-butyl (S)-4-(5-(1-((2-amino-5-cyano-6-methylpyrimidin-4-yl)amino)propyl)-1-methyl-1H-pyrrolo[3,2-b]pyridin-6-yl)piperazine-1-carboxylate in place of tert-butyl (S)-4-(5-(1-((2-amino-5-cyano-6-methylpyrimidin-4-yl)amino)ethyl)-1-methyl-1H-pyrrolo[3,2-b]pyridin-6-yl)piperazine-1-carboxylate. The title compound was isolated as an off-white solid. $^1$H NMR (400 MHz, DMSO-$d_6$) δ ppm 0.81 (t, J=7.45 Hz, 3H), 1.94 (t, J=7.33 Hz, 2H), 2.82 (br s, 2H), 3.13 (dd, J=3.28, 1.52 Hz, 6H), 5.91-6.12 (m, 1H), 6.54 (d, J=3.03 Hz, 1H), 7.44 (d, J=3.28 Hz, 1H), 7.76 (s, 1H); ESI-MS m/z [M+H]$^+$ calc'd for $C_{21}H_{27}N_9$, 406. found 406.

Example 20

(S)-2-Amino-4-ethyl-6-((1-(1-methyl-6-(piperazin-1-yl)-1H-pyrrolo[3,2-b]pyridin-5-yl)ethyl)amino)pyrimidine-5-carbonitrile

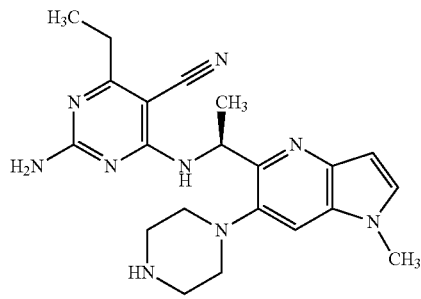 [SMILES: CCc1nc(N)nc(N[C@@H](C)c2nc3ccn(C)c3cc2N2CCNCC2)c1C#N]

Step A: 4-Chloro-6-ethyl-2-(methylthio)pyrimidine-5-carbonitrile

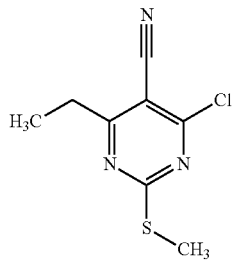

To a 100 mL round-bottom flask was added 4,6-dichloro-2-(methylthio)pyrimidine-5-carbonitrile (300 mg, 1.363 mmol) in tetrahydrofuran (10 mL). The reaction mixture was cooled to −78° C. Ethylmagnesium bromide in ether (3.0 M, 0.454 mL, 1.363 mmol) was added and the reaction mixture was allowed to stir for 1 hour at room temperature. LCMS indicated the reaction was complete. The reaction mixture was quenched with a few drops saturated aqueous NH$_4$Cl and allowed to warm to room temperature. The reaction mixture was diluted with EtOAc and washed with saturated aqueous NH$_4$Cl (3×). The combined organic layers were dried over MgSO$_4$, filtered, and concentrated. The product was purified by column chromatography (ISCO 12 g, 20-100% EtOAc/hexane gradient) to give the title compound as a pasty yellow solid. ESI-MS m/z [M+H]$^+$ calc'd for $C_8H_8ClN_3S$, 214. found 214.

Step B: tert-Butyl (S)-4-(5-(1-((5-cyano-6-ethyl-2-(methylthio)pyrimidin-4-yl)amino)ethyl)-1-methyl-1H-pyrrolo[3,2-b]pyridin-6-yl)piperazine-1-carboxylate

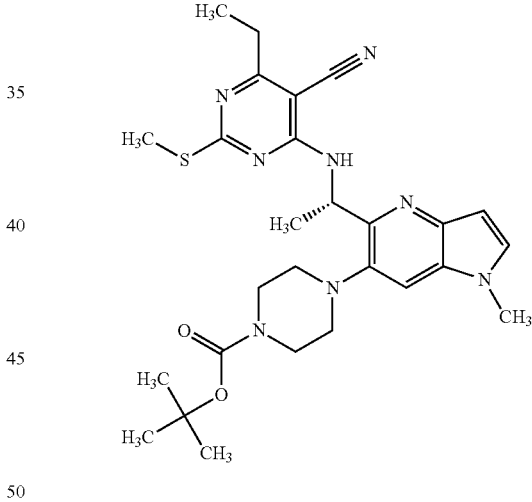

To a 20 mL vial were added (S)-tert-butyl 4-(5-(1-aminoethyl)-1-methyl-1H-pyrrolo[3,2-b]pyridin-6-yl)piperazine-1-carboxylate (63 mg, 0.175 mmol) in THF (5 mL), 4-chloro-6-ethyl-2-(methylthio)pyrimidine-5-carbonitrile (37.5 mg, 0.175 mmol) and Et$_3$N (0.027 mL, 0.193 mmol). The resulting yellow solution was heated to 60° C. and stirred overnight. The next day LCMS indicated the reaction was mostly complete. The reaction mixture was diluted with EtOAc and washed with saturated aqueous NH$_4$Cl (3×). The combined organic layers were dried over MgSO$_4$, filtered, and concentrated. The product was purified by column chromatography (ISCO 12 g, 30-100% EtOAc/hexane gradient) to give the title compound as a yellow solid. ESI-MS m/z [M+H]$^+$ calc'd for $C_{27}H_{36}N_8O_2S$, 537. found 537.

Step C: tert-Butyl (S)-4-(5-(1-((5-cyano-6-ethyl-2-(methylsulfonyl)pyrimidin-4-yl)amino)ethyl)-1-methyl-1H-pyrrolo[3,2-b]pyridin-6-yl)piperazine-1-carboxylate

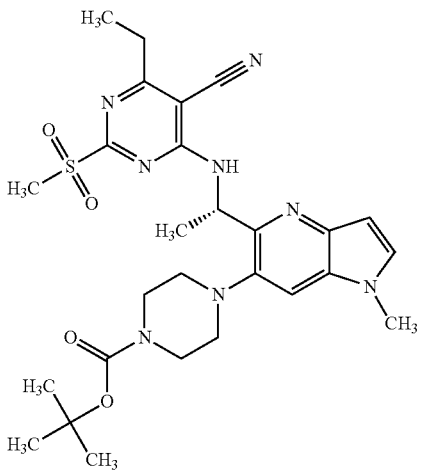 [SMILES: CCc1nc(S(C)(=O)=O)nc(N[C@@H](C)c2nc3ccn(C)c3cc2N2CCN(C(=O)OC(C)(C)C)CC2)c1C#N]

To a 20 mL round-bottom flask were added (S)-tert-butyl 4-(5-(1-((5-cyano-6-ethyl-2-(methylthio)pyrimidin-4-yl)amino)ethyl)-1-methyl-1H-pyrrolo[3,2-b]pyridin-6-yl)piperazine-1-carboxylate (78 mg, 0.145 mmol) in acetonitrile (1.5 mL) and water (1.5 mL) along with OXONE® (223 mg, 0.363 mmol) at 0° C. The reaction mixture was allowed to stir for 30 minutes at 0° C. and then for 3.5 hours at room temperature. LCMS indicated the reaction was mostly complete. The reaction mixture was diluted with EtOAc and washed with brine (3×). The combined organic layers were dried over MgSO$_4$, filtered, and concentrated. The product was purified by column chromatography (ISCO 4 g, 30-100% EtOAc/hexane gradient) to give the title compound as a yellow oil. ESI-MS m/z [M+H]$^+$ calc'd for $C_{27}H_{36}N_8O_4S$, 569. found 569.

Step D: tert-Butyl (S)-4-(5-(1-((2-amino-5-cyano-6-ethylpyrimidin-4-yl)amino)ethyl)-1-methyl-1H-pyrrolo[3,2-b]pyridin-6-yl)piperazine-1-carboxylate

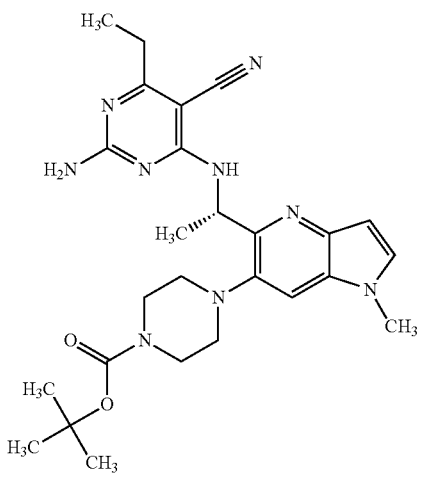 [SMILES: CCc1nc(N)nc(N[C@@H](C)c2nc3ccn(C)c3cc2N2CCN(C(=O)OC(C)(C)C)CC2)c1C#N]

To a 10 mL vial were added tert-butyl (S)-4-(5-(1-((5-cyano-6-ethyl-2-(methylsulfonyl)pyrimidin-4-yl)amino)ethyl)-1-methyl-1H-pyrrolo[3,2-b]pyridin-6-yl)piperazine-1-carboxylate (32 mg, 0.056 mmol) in dioxane (2 mL) along with 0.5 M ammonia in dioxane (6.09 µL, 0.281 mmol) to give a yellow solution. The vial was sealed and the reaction mixture was stirred overnight at 75° C. The next day LCMS indicated the reaction was incomplete. Additional NH$_3$ solution (2 eq) was added and the reaction mixture was allowed to stir for 6 hours at 75° C. LCMS showed the reaction was mostly complete. The reaction mixture was diluted with EtOAc and washed with saturated aqueous NH$_4$Cl (3×). The combined organic layers were dried over MgSO$_4$, filtered, and concentrated. The product was purified by column chromatography (ISCO 4 g, 50-100% EtOAc/hexane gradient) to give the title compound as a yellow oil.

Step E: (S)-2-Amino-4-ethyl-6-((1-(1-methyl-6-(piperazin-1-yl)-1H-pyrrolo[3,2-b]pyridin-5-yl)ethyl)amino)pyrimidine-5-carbonitrile To a 10 mL round-bottom flask were added (S)-tert-butyl 4-(5-(1-((2-amino-5-cyano-6-ethylpyrimidin-4-yl)amino)ethyl)-1-methyl-1H-pyrrolo[3,2-b]pyridin-6-yl)piperazine-1-carboxylate (20 mg, 0.040 mmol) in diethyl ether (1 mL) along with 2 M HCl in ether (0.079 mL, 0.158 mmol) to give a yellow suspension. The reaction mixture was allowed to stir for 6 hours at room temperature. LCMS showed the reaction was complete. The reaction mixture was concentrated and the product purified by HPLC (acid mode, 5-35% ACN/water gradient). The pure fractions were combined and lyophilized to give a TFA salt of the title compound as a white solid. $^1$H NMR (400 MHz, DMSO-d$_6$) δ ppm 1.16 (s, 3H), 1.37-1.44 (m, 3H), 2.58-2.75 (m, 2H), 2.81-3.01 (m, 5H), 3.81 (s, 3H), 5.75-5.88 (m, 1H), 6.44-6.53 (m, 1H), 6.94-7.13 (m, 3H), 7.52-7.57 (m, 1H), 7.78-7.83 (m, 1H); ESI-MS m/z [M+H]$^+$ calc'd for $C_{21}H_{27}N_9$, 406. found 406.

TABLE 1 lists PI3Kδ inhibition data for compounds described in the examples, where smaller IC$_{50}$ values represent higher potency. The compounds were tested in accordance with the assay described in the specification beginning at page 44.

TABLE 1

PI3Kδ Inhibition for Example Compounds

| EXAMPLE No. | PI3Kδ IC$_{50}$ µM |
|---|---|
| 1 | 0.0007 |
| 2 | 0.0050 |
| 3 | 0.0056 |
| 4 | 0.0029 |
| 5 | 0.0054 |
| 6 | 0.0050 |
| 7 | 0.0042 |
| 8 | 0.0026 |
| 9 | 0.0022 |
| 10 | 0.0035 |
| 11 | 0.0013 |
| 12 | 0.0014 |
| 13 | 0.0010 |
| 14 | 0.0006 |
| 15 | 0.0055 |
| 16 | 0.0024 |
| 17 | 0.0085 |
| 18 | 0.0017 |
| 19 | 0.0008 |
| 20 | 0.22 |

TABLE 2 lists thermodynamic (aqueous) solubility for compounds described in EXAMPLE 1, 6, 12, and 14, where larger values indicate higher solubility. TABLE 2 also lists thermodynamic solubility for compounds A and B, which correspond to compounds shown in EXAMPLE 26 and 29, respectively, in international patent application PCT/US13/49612 (published as WO 2014/011568). For each compound in TABLE 2, the thermodynamic solubility of the solid free base in JP2 was measured in accordance with the method described in the specification beginning at page 46.

TABLE 2

Thermodynamic solubility in JP2

| EXAMPLE No. | Structure | Thermodynamic Solubility in JP2 (µg/mL) |
| --- | --- | --- |
| 1 | [structure] | 2195 |
| 6 | [structure] | 1730 |
| 12 | [structure] | 150 |
| 14 | [structure] | >1830 |
| A | [structure] | 20 |
| B | [structure] | 26 |

As used in the description and the claims, singular articles such as "a," "an," and "the," may refer to a single object or to a plurality of objects unless the context clearly indicates otherwise. Thus, for example, reference to a composition containing "a compound" may include a single compound or two or more compounds. The above description is intended to be illustrative and not restrictive. Therefore, the scope of the invention should be determined with reference to the claims and includes the full scope of equivalents to which such claims are entitled. The disclosures of all articles and references, including patents and published patent applications, are herein incorporated by reference in their entirety and for all purposes.

What is claimed is:

1. A compound of Formula 1,

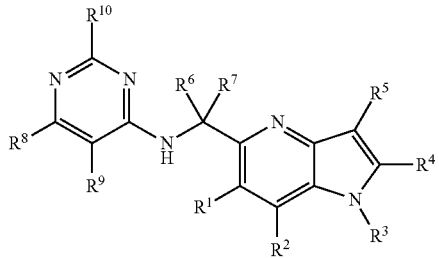

or a pharmaceutically acceptable salt thereof, wherein:
$R^1$ is selected from:
- (a) $C_{3-8}$ cycloalkyl, which is substituted with —$NH_2$ alone;
- (b) $C_{3-8}$ cycloalkenyl, which is substituted with —$NH_2$ alone;
- (c) $C_{2-6}$ heterocyclyl, which is bonded directly to an azaindole moiety shown in Formula 1 through a carbon atom, has one unsubstituted nitrogen heteroatom and no other heteroatoms, and is optionally substituted with $R^{18}$;
- (d) $C_{2-6}$ heterocyclyl, which is bonded directly to the azaindole moiety through a nitrogen heteroatom, is substituted with —$NHR^{16}$ or has at least one additional heteroatom that is unsubstituted nitrogen, and is optionally substituted with $R^{18}$; and
- (e) $C_{3-6}$ heterocyclyl-$N(R^{13})$— in which the heterocyclyl moiety has one unsubstituted nitrogen heteroatom and no other heteroatoms, and is optionally substituted with $R^{18}$;

$R^2$, $R^4$, and $R^5$ are each independently selected from hydrogen, halo, —OH, —CN, $C_{1-3}$ alkyl, and $C_{1-3}$ haloalkyl;
$R^3$ is selected from hydrogen, $C_{1-3}$ alkyl, and $C_{1-3}$ haloalkyl;
$R^6$ and $R^7$ are each independently selected from hydrogen, $C_{1-3}$ alkyl, and $C_{1-3}$ haloalkyl;
$R^8$ is selected from hydrogen, $C_{1-3}$ alkyl, and —$NH_2$;
$R^9$ is selected from hydrogen, halo, —CN, $C_{1-3}$ haloalkyl, —$OR^{16}$, —$C(O)R^{16}$, —$C(O)OR^{16}$, —$C(O)N(R^{16})R^{17}$, —$C(O)N(R^{16})OR^{17}$, —$C(O)N(R^{16})S(O)_2R^{18}$, —$SR^{16}$, —$S(O)R^{18}$, —$S(O)_2R^{18}$, and —$S(O)_2N(R^{16})R^{17}$;
$R^{10}$ is selected from halo, —OH, $C_{1-3}$ alkyl, —$NHR^{16}$, and —$NHC(O)R^{16}$;
each $R^{13}$ is selected from hydrogen, $C_{1-6}$ alkyl, and $C_{3-6}$ cycloalkyl;
each $R^{16}$ and $R^{17}$ is independently selected from hydrogen, $C_{1-6}$ alkyl, and $C_{3-6}$ cycloalkyl; and
each $R^{18}$ is independently selected from $C_{1-6}$ alkyl and $C_{3-6}$ cycloalkyl.

2. The compound or pharmaceutically acceptable salt according to claim 1, wherein $R^1$ is selected from:
- (a) $C_{3-6}$ cycloalkyl, which is substituted with —$NH_2$ alone;
- (b) $C_{3-6}$ cycloalkenyl, which is substituted with —$NH_2$ alone;
- (c) $C_{3-6}$ heterocyclyl, which is bonded directly to the azaindole moiety through a carbon atom, has one unsubstituted nitrogen heteroatom and no other heteroatoms, and is unsubstituted;
- (d) $C_{2-6}$ heterocyclyl, which is bonded directly to the azaindole moiety through a nitrogen heteroatom, is substituted with —$NH_2$ or has one additional nitrogen heteroatom which is unsubstituted and no other heteroatoms, and is optionally substituted with $R^{18}$; and
- (e) $C_{3-6}$ heterocyclyl-$N(R^{13})$— in which the heterocyclyl moiety has one unsubstituted nitrogen heteroatom and no other heteroatoms, and is unsubstituted.

3. The compound or pharmaceutically acceptable salt according to claim 1, wherein $R^1$ is $C_{3-8}$ cycloalkyl, which is substituted with —$NH_2$ alone.

4. The compound or pharmaceutically acceptable salt according to claim 3, wherein $R^1$ is $C_{3-6}$ cycloalkyl, which is substituted with —$NH_2$ alone.

5. The compound or pharmaceutically acceptable salt according to claim 1, wherein $R^1$ is $C_{3-8}$ cycloalkenyl, which is substituted with —$NH_2$ alone.

6. The compound or pharmaceutically acceptable salt according to claim 5, wherein $R^1$ is $C_{3-6}$ cycloalkenyl, which is substituted with —$NH_2$ alone.

7. The compound or pharmaceutically acceptable salt according to claim 1, wherein $R^1$ is $C_{3-6}$ heterocyclyl, which is bonded directly to the azaindole moiety through a carbon atom, has one unsubstituted nitrogen heteroatom and no other heteroatoms, and is optionally substituted with $R^{18}$.

8. The compound or pharmaceutically acceptable salt according to claim 7, wherein $R^1$ is $C_{3-6}$ heterocyclyl, which is bonded directly to the azaindole moiety through a carbon atom, has one unsubstituted nitrogen heteroatom and no other heteroatoms, and is unsubstituted.

9. The compound or pharmaceutically acceptable salt according to claim 1, wherein $R^1$ is $C_{2-6}$ heterocyclyl, which is bonded directly to the azaindole moiety through a nitrogen heteroatom, is substituted with —$NHR^6$ or has at least one additional heteroatom that is unsubstituted nitrogen, and is optionally substituted with $R^{18}$.

10. The compound or pharmaceutically acceptable salt according to claim 9, wherein $R^1$ is $C_{2-6}$ heterocyclyl, which is bonded directly to the azaindole moiety through a nitrogen heteroatom, is substituted with —$NH_2$ or has one additional nitrogen heteroatom which is unsubstituted and no other heteroatoms, and is optionally substituted with $R^{18}$.

11. The compound or pharmaceutically acceptable salt according to claim 1, wherein $R^1$ is $C_{3-6}$ heterocyclyl-$N(R^{13})$— in which the heterocyclyl moiety has one unsubstituted nitrogen heteroatom and no other heteroatoms, and is optionally substituted with $R^{18}$.

12. The compound or pharmaceutically acceptable salt according to claim 11, wherein $R^1$ is $C_{2-6}$ heterocyclyl-$N(R^{13})$— in which the heterocyclyl moiety has one unsubstituted nitrogen heteroatom and no other heteroatoms, and is unsubstituted.

13. The compound or pharmaceutically acceptable salt according to claim 1, wherein $R^1$ is selected from aminocyclohexyl, aminocyclohexenyl, azetidinyl, pyrrolidinyl, piperidinyl, piperazinyl, diazepanyl, diazabicyclo[2.2.1]heptanyl, azetidinylamino, and piperidinylamino, each optionally substituted as defined in claim 1.

14. The compound or pharmaceutically acceptable salt according to claim 1, wherein $R^1$ is selected from 4-aminocyclohexyl, 4-aminocyclohex-1-en-1-yl, pyrrolidin-3-yl, piperidin-4-yl, pyrrolidin-1-yl, piperidin-1-yl, piperazin-1-yl, 1,4-diazepan-1-yl, 2,5-diazabicyclo[2.2.1]heptan-2-yl, azetidin-3-ylamino, and piperidin-4-ylamino, each optionally substituted as defined in claim 1.

15. The compound or pharmaceutically acceptable salt according to claim 1, wherein $R^1$ is selected from 4-aminocyclohexyl, 4-aminocyclohex-1-en-1-yl, (R)-pyrrolidin-3-yl, (S)-pyrrolidin-3-yl, piperidin-4-yl, (R)-3-aminopyrrolidin-1- yl, (S)-3-aminopyrrolidin-1-yl, (R)-3-(methylamino)pyrrolidin-1-yl, (S)-3-(methylamino)pyrrolidin-1-yl, (R)-3-aminopiperidin-1-yl, (S)-3-aminopiperidin-1-yl, piperazin-1-yl, (R)-3-methylpiperazin-1-yl, (S)-3-methylpiperazin-1-yl, 1,4-diazepan-1-yl, (1S,4S)-2,5-diazabicyclo[2.2.1]heptan-2-yl, azetidin-3-yl(methyl)amino, and piperidin-4-ylamino.

16. The compound or pharmaceutically acceptable salt according to claim 1, wherein $R^2$, $R^4$, and $R^5$ are each independently selected from hydrogen and halo.

17. The compound or pharmaceutically acceptable salt according to claim 16, wherein at most one of $R^2$, $R^4$, and $R^5$ is halo.

18. The compound or pharmaceutically acceptable salt according to claim 1, wherein each of $R^2$ and $R^4$ is hydrogen.

19. The compound or pharmaceutically acceptable salt according to claim 1, wherein $R^3$ is $C_{1-3}$ alkyl or $C_{1-3}$ haloalkyl.

20. The compound or pharmaceutically acceptable salt according to claim 19, wherein $R^3$ is methyl.

21. The compound or pharmaceutically acceptable salt according to claim 1, wherein one of $R^6$ and $R^7$ is hydrogen.

22. The compound or pharmaceutically acceptable salt according to claim 21, wherein one of $R^6$ and $R^7$ is $C_{1-3}$ alkyl.

23. The compound or pharmaceutically acceptable salt according to claim 1, wherein $R^8$ is selected from methyl, ethyl, and —$NH_2$.

24. The compound or pharmaceutically acceptable salt according to claim 1, wherein $R^8$ is selected from methyl and —$NH_2$.

25. The compound or pharmaceutically acceptable salt according to claim 1, wherein $R^9$ is selected from halo, —CN, and $C_{1-3}$ haloalkyl.

26. The compound or pharmaceutically acceptable salt according to claim 25, wherein $R^9$ is —CN.

27. The compound or pharmaceutically acceptable salt according to claim 1, wherein $R^{10}$ is —$NH_2$.

28. The compound according to claim 1, which is selected from the following compounds:
(S)-2-Amino-4-methyl-6-(1-(1-methyl-6-(piperazin-1-yl)-1H-pyrrolo[3,2-b]pyridin-5-yl)ethylamino)pyrimidine-5-carbonitrile;
(S)-4-(1-(6-(1,4-Diazepan-1-yl)-1-methyl-1H-pyrrolo[3,2-b]pyridin-5-yl)ethylamino)-2-amino-6-methylpyrimidine-5-carbonitrile;
2-Amino-4-methyl-6-((S)-1-(1-methyl-6-((S)-3-(methylamino)pyrrolidin-1-yl)-1H-pyrrolo[3,2-b]pyridin-5-yl)ethylamino)pyrimidine-5-carbonitrile;
2-Amino-4-((S)-1-(6-((R)-3-aminopiperidin-1-yl)-1-methyl-1H-pyrrolo[3,2-b]pyridin-5-yl)ethylamino)-6-methylpyrimidine-5-carbonitrile;
2-Amino-4-((S)-1-(6-((S)-3-aminopiperidin-1-yl)-1-methyl-1H-pyrrolo[3,2-b]pyridin-5-yl)ethylamino)-6-methylpyrimidine-5-carbonitrile;
2-Amino-4-methyl-6-((S)-1-(1-methyl-6-((S)-3-methylpiperazin-1-yl)-1H-pyrrolo[3,2-b]pyridin-5-yl)ethylamino)pyrimidine-5-carbonitrile;
2-Amino-4-((S)-1-(6-((R)-3-aminopyrrolidin-1-yl)-1-methyl-1H-pyrrolo[3,2-b]pyridin-5-yl)ethylamino)-6-methylpyrimidine-5-carbonitrile;
2-Amino-4-((S)-1-(6-((S)-3-aminopyrrolidin-1-yl)-1-methyl-1H-pyrrolo[3,2-b]pyridin-5-yl)ethylamino)-6-methylpyrimidine-5-carbonitrile;
2-Amino-4-methyl-6-((S)-1-(1-methyl-6-((R)-3-methylpiperazin-1-yl)-1H-pyrrolo[3,2-b]pyridin-5-yl)ethylamino)pyrimidine-5-carbonitrile;
2-Amino-4-methyl-6-((S)-1-(1-methyl-6((S)-pyrrolidin-3-yl)-1H-pyrrolo[3,2-b]pyridin-5-yl)ethylamino)pyrimidine-5-carbonitrile;
2-Amino-4-methyl-6-((S)-1-(1-methyl-6-((R)-pyrrolidin-3-yl)-1H-pyrrolo[3,2-b]pyridin-5-yl)ethylamino)pyrimidine-5-carbonitrile;
(S)-2-Amino-4-methyl-6-(1-(1-methyl-6-(piperidin-4-yl)-1H-pyrrolo[3,2-b]pyridin-5-yl)ethylamino)pyrimidine-5-carbonitrile;
(S)-2,4-Diamino-6-(1-(1-methyl-6-(piperazin-1-yl)-1H-pyrrolo[3,2-b]pyridin-5-yl)ethylamino)pyrimidine-5-carbonitrile;
4-((S)-1-(6-((1S,4S)-2,5-Diazabicyclo[2.2.1]heptan-2-yl)-1-methyl-1H-pyrrolo[3,2-b]pyridin-5-yl)ethylamino)-2-amino-6-methylpyrimidine-5-carbonitrile;
(S)-2-Amino-4-methyl-6-((1-(1-methyl-6-(piperidin-4-ylamino)-1H-pyrrolo[3,2-b]pyridin-5-yl)ethyl)amino)pyrimidine-5-carbonitrile;
(S)-2-Amino-4-((1-(6-(azetidin-3-yl(methyl)amino)-1-methyl-1H-pyrrolo[3,2-b]pyridin-5-yl)ethyl)amino)-6-methylpyrimidine-5-carbonitrile;
2-Amino-4-(((1S)-1-(6-(4-aminocyclohex-1-en-1-yl)-1-methyl-1H-pyrrolo[3,2-b]pyridin-5-yl)ethyl)amino)-6-methylpyrimidine-5-carbonitrile;
(S)-2-Amino-4-((1-(6-(4-aminocyclohexyl)-1-methyl-1H-pyrrolo[3,2-b]pyridin-5-yl)ethyl)amino)-6-methylpyrimidine-5-carbonitrile;
2-amino-4-(((S)-1-(6-((1s,4R)-4-aminocyclohexyl)-1-methyl-1H-pyrrolo[3,2-b]pyridin-5-yl)ethyl)amino)-6-methylpyrimidine-5-carbonitrile;
2-amino-4-(((S)-1-(6-((1r,4S)-4-aminocyclohexyl)-1-methyl-1H-pyrrolo[3,2-b]pyridin-5-yl)ethyl)amino)-6-methylpyrimidine-5-carbonitrile;
(S)-2-Amino-4-methyl-6-((1-(1-methyl-6-(piperazin-1-yl)-1H-pyrrolo[3,2-b]pyridin-5-yl)propyl)amino)pyrimidine-5-carbonitrile;
(S)-2-Amino-4-ethyl-6-((1-(1-methyl-6-(piperazin-1-yl)-1H-pyrrolo[3,2-b]pyridin-5-yl)ethyl)amino)pyrimidine-5-carbonitrile;
a stereoisomer of any of the aforementioned compounds; and
a pharmaceutically acceptable salt of any of the aforementioned compounds or stereoisomers.

29. The compound according to claim 1, which is (S)-2-amino-4-methyl-6-(1-(1-methyl-6-(piperazin-1-yl)-1H-pyrrolo[3,2-b]pyridin-5-yl)ethylamino)pyrimidine-5-carbonitrile or a pharmaceutically acceptable salt thereof.

30. The compound according to claim 1, which is 2-amino-4-methyl-6-((S)-1-(1-methyl-6-((R)-pyrrolidin-3-yl)-1H-pyrrolo[3,2-b]pyridin-5-yl)ethylamino)pyrimidine-5-carbonitrile or a pharmaceutically acceptable salt thereof.

31. The compound according to claim 1, which is (S)-2-amino-4-methyl-6-(1-(1-methyl-6-(piperidin-4-yl)-1H-pyrrolo[3,2-b]pyridin-5-yl)ethylamino)pyrimidine-5-carbonitrile or a pharmaceutically acceptable salt thereof.

32. The compound according to claim 1, which is (S)-2,4-diamino-6-(1-(1-methyl-6-(piperazin-1-yl)-1H-pyrrolo[3,2-b]pyridin-5-yl)ethylamino)pyrimidine-5-carbonitrile or a pharmaceutically acceptable salt thereof.

33. The compound according to claim 1, which is 4-((S)-1-(6-((1S,4S)-2,5-diazabicyclo[2.2.1]heptan-2-yl)-1-methyl-1H-pyrrolo[3,2-b]pyridin-5-yl)ethylamino)-2-amino-6-methylpyrimidine-5-carbonitrile or a pharmaceutically acceptable salt thereof.

34. The compound according to claim 1, which is (S)-2-amino-4-methyl-6-((1-(1-methyl-6-(piperazin-1-yl)-1H- pyrrolo[3,2-b]pyridin-5-yl)propyl)amino)pyrimidine-5-carbonitrile or a pharmaceutically acceptable salt thereof.

35. A pharmaceutical composition comprising:
a compound or pharmaceutically acceptable salt as defined in claim 1; and
a pharmaceutically acceptable excipient.

36. A method of treating a disease, disorder or condition in a subject, the method comprising administering to the subject a compound or pharmaceutically acceptable salt as defined in claim 1, wherein the disease, disorder or condition is selected from asthma, rheumatoid arthritis, systemic lupus erythematosus, chronic obstructive pulmonary disease, atherosclerosis, myocardial infarction, and thrombosis.

37. A combination comprising an effective amount of a compound or pharmaceutically acceptable salt as defined in claim 1, and at least one additional pharmacologically active agent.

* * * * *